United States Patent [19]

Kramer et al.

[11] Patent Number: 5,462,933
[45] Date of Patent: Oct. 31, 1995

[54] MODIFIED BILE ACID CONJUGATES, AND THEIR USE AS PHARMACEUTICALS

[75] Inventors: Werner Kramer, Mainz; Günther Wess, Erlensee, both of Germany

[73] Assignee: Hoechst Aktiengesellschaft, Frankfurt am Main, Germany

[21] Appl. No.: 208,192

[22] Filed: Mar. 10, 1994

Related U.S. Application Data

[63] Continuation of Ser. No. 806,799, Dec. 12, 1991, abandoned, which is a continuation of Ser. No. 581,390, Sep. 12, 1990, abandoned.

[30] Foreign Application Priority Data

Sep. 14, 1989 [DE] Germany ............ 39 30 696.8

[51] Int. Cl.$^6$ ................. A61K 31/58; C07J 43/00
[52] U.S. Cl. ................. 514/176; 424/528; 540/5; 540/106; 540/107; 540/113
[58] Field of Search .................. 540/106, 107, 540/113, 5; 514/176; 424/528

[56] References Cited

U.S. PATENT DOCUMENTS

| | | | |
|---|---|---|---|
| 2,441,129 | 5/1948 | Berczeller | 552/550 |
| 3,937,815 | 2/1976 | Bruzzese et al. | 424/94.61 |
| 4,418,059 | 11/1983 | Lalezari | 424/180 |
| 4,499,020 | 2/1985 | Lalezari | 260/397.1 |
| 4,925,852 | 5/1990 | Kesseler et al. | 514/269 |
| 4,968,790 | 11/1990 | DeVries et al. | 536/117 |

FOREIGN PATENT DOCUMENTS

| | | |
|---|---|---|
| 58682/80 | 11/1980 | Australia . |
| 86941/82 | 2/1983 | Australia . |
| 13799/83 | 11/1983 | Australia . |
| 0105404A1 | 4/1984 | European Pat. Off. . |

OTHER PUBLICATIONS

Lehninger, *Principles of Biochemistry*, Worth Publishers, Inc., (1982), pp. 690–691.
Ho, N. F. H., "Utilizing Bile Acid Carrier mechanisms to Enhance Liver and Small Intestine Absorption," Annals new York Academy of Sciences 110:315–329 (1987).
Fieser, L. F. and Fieser, M., Steroids, pp. 3, 53–55, 64, 77, 79, 83 (Reinhold Pub. Corp., N.Y., 1959).

*Primary Examiner*—Philip I. Datlow
*Attorney, Agent, or Firm*—Finnegan, Henderson, Farabow, Garrett & Dunner

[57] ABSTRACT

Bile acid derivatives processes for their preparation and use as pharmaceuticals.

Bile acid derivatives of the formula I

W—X—G in which G is a bile acid radical, W is an active compound moiety of a medicament and X is a bonding member between a bile acid radical and active compound moiety, are outstandingly suitable for introducing active compounds into the enterohepatic circulation. The compounds I are absorbed and pass into the bloodstream. It is possible in this way, using the natural reabsorption of the bile acids, to achieve improved absorption of non-absorbable or poorly absorbable pharmaceuticals.

W may be, for example, a peptide, an antibiotic, an antiviral substance, an anticancer agent, a hepatoprotective agent, an antihyperlipidemic, a diuretic, a hypotensive, a renin inhibitor, a substance for the treatment of cirrhosis of the liver or a substance for the treatment of diabetes.

G is a bile acid radical in the form of the free natural or chemically modified acids, the esters and amides, the salt forms and forms derivatized on alcohol groups.

X is a large number of intermediate members or, alternatively, a bond.

5 Claims, No Drawings

MODIFIED BILE ACID CONJUGATES, AND THEIR USE AS PHARMACEUTICALS

This application is a continuation of application Ser. No. 07/806,799, filed Dec. 12, 1991, now abandoned; which is a continuation of application Ser. No. 07/581,390, filed Sep. 12, 1990, abandoned.

The oral administration of pharmaceuticals is the most common and most convenient type of pharmaceutical administration. However, in order for an active compound to pass into the bloodstream, an absorption process has to take place in the gastrointestinal tract. The pharmaceutical is then distributed in the body in accordance with its specific properties. However, numerous pharmaceuticals are only absorbed very poorly or virtually not at all, so that oral administration is not possible.

It is known that, by coupling of non-absorbable pharmaceuticals to vitamin B12, an enteral absorption of these pharmaceuticals can be achieved (Proceed. Symp. Control. Rel. Bioact. Mater. 15 (1988) Controlled Release Society Inc., see PCT/AU 86/0299).

Because of the very low capacity of this absorption route via vitamin B12, however, only very small amounts of the pharmacon can be introduced into the body.

Bile acid derivatives have now been found which are used for the purpose of making poorly absorbable or non-absorbable active compounds absorbable and thus making possible the oral administration of these substances even in high doses. Moreover, a liver-specific action of active compounds can be achieved using the the acid derivatives.

The invention relates to bile acid derivatives of the formula I

    I consisting of a bile acid radical G, an active compound moiety W and a connecting member X between the bile acid radical and active compound moiety.

In formula I
the bile acid radical G is bile acids in the form of the free natural or chemically modified acids, the esters and amides, the salt forms and the forms derivatized on the alcohol groups,
the connecting member X
is a direct bond or
an intermediate member,
in fact, in particular,
X may be

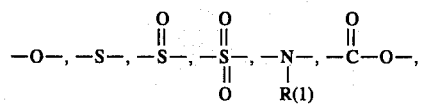

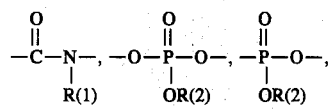

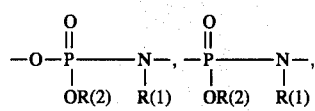

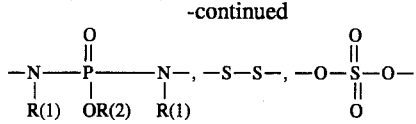

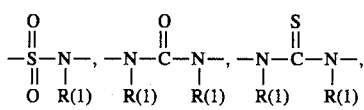

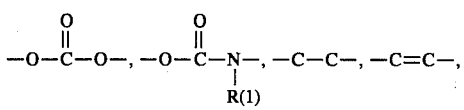

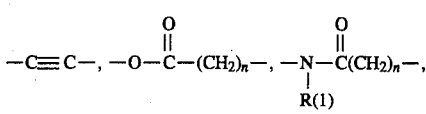

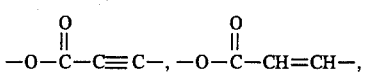

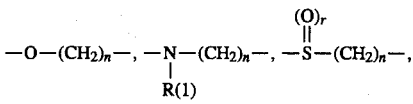

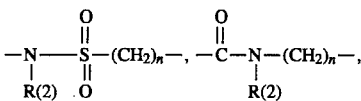

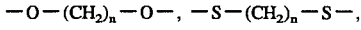

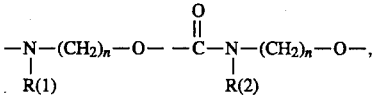

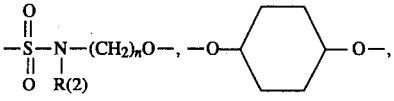

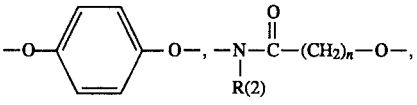

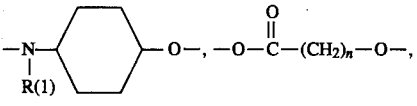

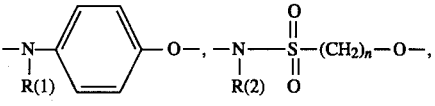

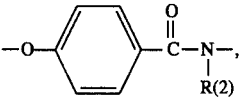

-continued

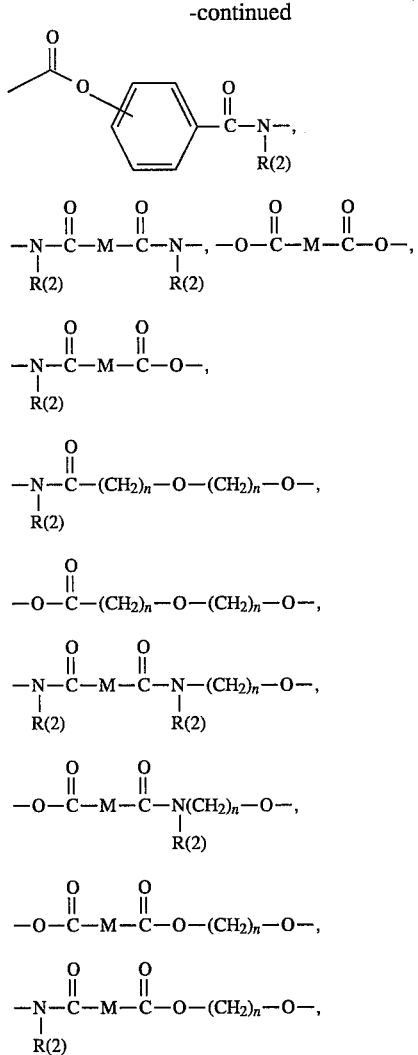

in which
R(1)=H, $(C_1-C_8)$-alkyl; the group

phenyl, benzyl, unsubstituted or monosubstituted to trisubstituted by F, Cl, Br, $(C_1-C_4)$-alkyl, or alkoxy having 1-4 carbon atoms, R(2)=H, $(C_1-C_8)$-alkyl, phenyl, benzyl, unsubstituted or monosubstituted to trisubstituted by F, Cl, Br, $(C_1-C_4)$-alkyl or alkoxy having 1-4 carbon atoms, m=0-6,
n=1-16,
p=1, 2 or 3,
r=0-2 and
M=—$(CH_2)_m$—, $(C=C)_p$, —C≡C—,

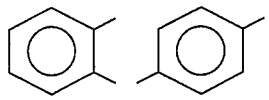

G and W may be bonded to either end of X. The active compound moiety W is a pharmacologically active radical, a pharmaceutical or a moiety of a pharmaceutical.

Preferred compounds of the formula I are those in which G is

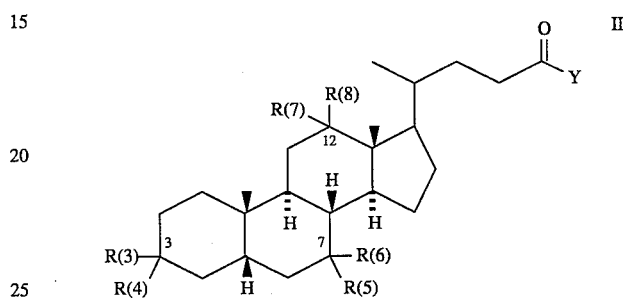

in all sterically possible arrangements in which R(3)-R(8) are identical or different and have the following meaning:

a bond to W—X—, where altogether up to two W—X— units may be bonded,

R(3) and R(4), R(5) and R(6), R(7) and R(8) are in each case Jointly the oxygen of a carbonyl group

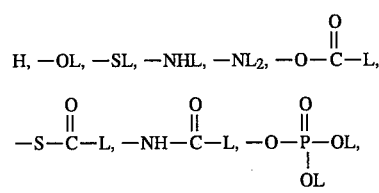

H, a saturated or unsaturated alkyl radical having 1-10 carbon atoms, which is branched or unbranched, cycloalkyl having 3-8 carbon atoms, a phenyl radical (which is unsubstituted or monosubstituted to trisubstituted by F, Cl, Br, $(C_1-C_4)$-alkyl or $(C_1-C_4)$-alkoxy), or a benzyl radical (which is unsubstituted or monosubstituted to trisubstituted by F, Cl, Br, $(C_1-C_4)$-alkyl or $(C_1-C_4)$-alkoxy);

and in which Y has the following meaning
—OL, —NHL, —$NL_2$, where L has the abovementioned meaning, an amino acid or aminosulfonic acid bonded via the amino group and its $(C_1-C_4)$-alkyl esters and alkali metal and alkaline earth metal salts,
—OKa, where Ka is a cation such as, for example, an alkali metal or alkaline earth metal ion or, alternatively, a quaternary ammonium ion, the connecting member X is

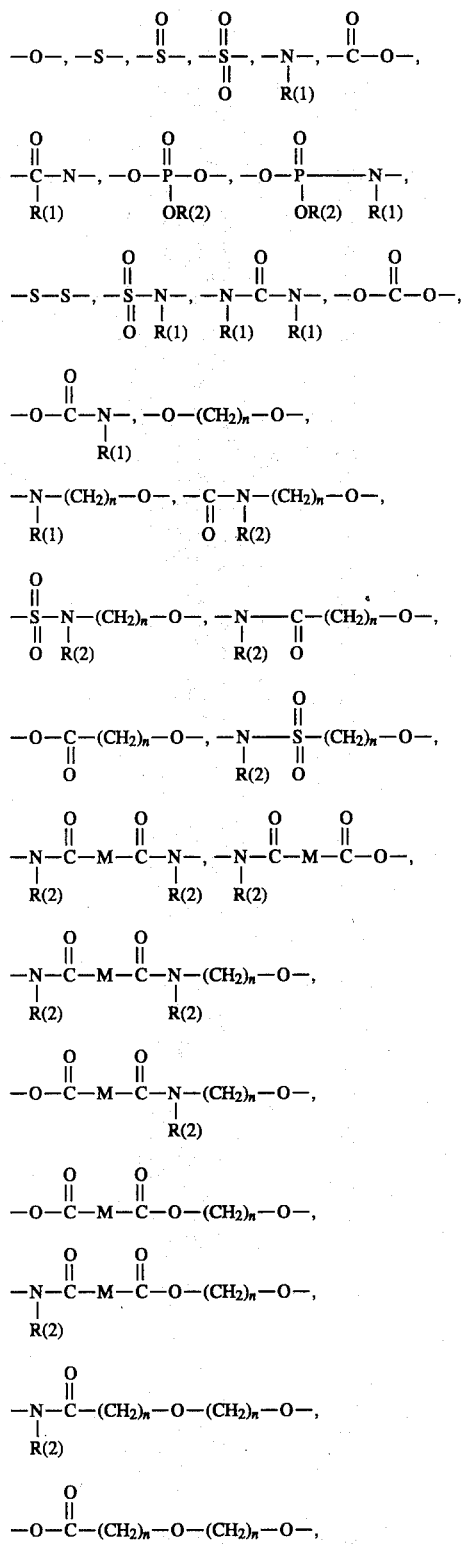

where
R(1)=H, (C₁–C₈)-alkyl, the group $$R(2)-\overset{O}{\underset{\|}{C}},$$

phenyl, benzyl, unsubstituted or monosubstituted to trisubstituted in the nucleus by F, Cl, Br, (C₁–C₄)-alkyl, or alkoxy having 1–4 carbon atoms;

R(2)=H, (C₁–C₈)-alkyl, phenyl, benzyl; in each case unsubstituted or monosubstituted to trisubstituted by F, Cl, Br, (C₁–C₄)-alkyl or alkoxy having 1–4 carbon atoms, n=1–16 and M=—(CH₂)ₘ—where m=2, where G and W may be bonded to either end of X.

The active compound W is any desired pharmaceutical for which a liver-selective medicament action is desired or a non-absorbable or poorly absorbable pharmaceutical for which it is intended to achieve an improved absorption.

For example,

W can be a peptide, an antibiotic, an antiviral substance, an anticancer agent such as, for example, chlorambucil, a hepatoprotective agent, an antihyperlipidemic, for example an HMG-CoA reductase inhibitor, a diuretic, a hypotensive, a renin inhibitor, a substance for the treatment of cirrhosis of the liver, for example a prolylhydroxylase inhibitor, or a substance for the treatment of diabetes.

Particularly preferred compounds of the formula I are those in which:

G is

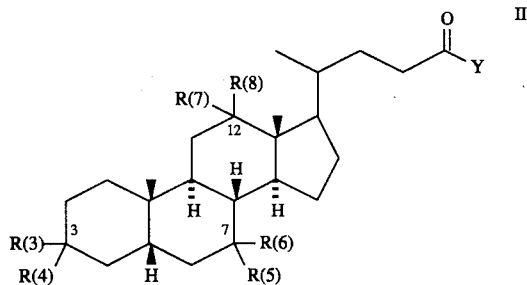

where R(3)–R(8) are identical or different and have the following meaning: a bond to W—X—, where up to two W—X— units may be bonded,

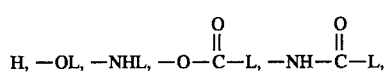

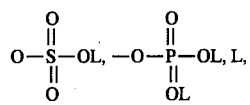

where L is:

H, a saturated alkyl radical having 1–6 carbon atoms, which may be branched or unbranched, or a phenyl radical which is unsubstituted or monosubstituted to trisubstituted by F, Cl, Br, $(C_1-C_4)$-alkyl or $(C_1-C_4)$-alkoxy, Y is: OL, —NHL, —NL$_2$, —OKa, where Ka is an alkali metal or alkaline earth metal cation or an ammonium ion

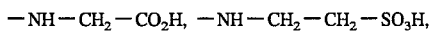

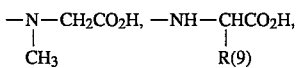

where R(9) is methyl, isopropyl, isobutyl, 2-butyl, benzyl, 4-hydroxybenzyl, hydroxymethyl, 1-hydroxyethyl, $H_3CSCH_2CH_2$—, $HO_2CCH_2$—, $HO_2CCH_2CH_2$—, the connecting member X, where G and W may be bonded to either end of X, is

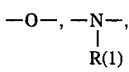

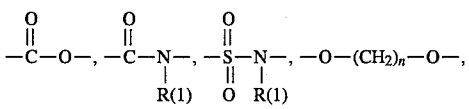

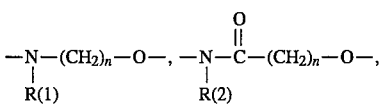

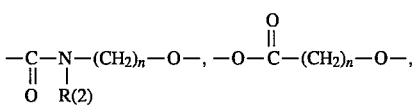

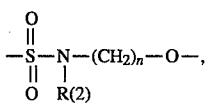

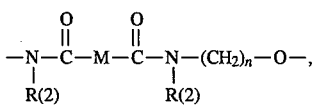

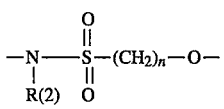

where
R(1)=H, $(C_1-C_8)$-alkyl,

phenyl, benzyl, where the aromatic rings are unsubstituted or monosubstituted to trisubstituted by F, Cl, Br, $(C_1-C_4)$-alkyl or $(C_1-C_4)$-alkoxy;

R(2)=H, $(C_1-C_8)$-alkyl, phenyl, benzyl; in each case unsubstituted or monosubstituted to trisubstituted by F, Cl, Br, $(C_1-C_1)$-alkyl or alkoxy having 1–4 carbon atoms, n=1–16 and
M=—$CH_2$—CH= CH—

The active compound W is any desired pharmaceutical for which a liver-selective medicament action is desired or a non-absorbable or poorly absorbable pharmaceutical for which it is intended to achieve an improved absorption.

For example, W can be a peptide, an antibiotic, an antiviral substance, an anticancer agent such as, for example, chlorambucil, a hepatoprotective agent, an antihyperlipidemic, for example an PIMG-CoA reductase inhibitor, a diuretic, a hypotensive, a renin inhibitor, a substance for the treatment of cirrhosis of the liver, for example a prolylhydroxylase inhibitor, or a substance for the treatment of diabetes.

The invention further relates to a process for the preparation of the compound I which comprises a) in the case of X=a direct bond, bringing suitable reactive forms of G and W to reaction with one another by processes known in principle or b) in the case of X=an intermediate member
α) bringing reactive forms of G—X and W or
β) reactive forms of W—X and G to reaction with one another by processes known in principle, c) preparing G—X and W—X by known processes, or if not known, by processes described in more detail below.

a) X=a direct bond

The bile acids are employed either in free form or in protected form. If necessary, the removal of the protective groups and the conversion of the C-24 carboxyl function to a derivative according to the invention is carried out after linking to W. Suitable protective groups for the alcohol groups are expediently acetyl, tetrahydropyranyl, t-butyldimethylsilyl or benzyl. Possible protective groups for the C-24 carboxyl group are various alkyl or benzyl esters, but also, for example, orthoesters.

For example, bile acid reacts preferably at position 3, but also at position 7, with activated forms of carboxylic acids, such as acid chlorides or mixed anhydrides with the addition of bases such as trialkylamine, pyridine, but also NaOH, at room temperature in suitable solvents such as tetrahydrofuran, methylene chloride or ethyl acetate, but also dimethylformamide (DMF) or dimethoxyethane (DME).

The various isomers may be separated, for example, by chromatography. By means of the use of suitable protective groups, the reaction can be carried out selectively. Analogously, appropriate amino bile acids can be converted into corresponding amides. Here also, the reaction can either be carried out with protected or free bile acids.

Analogously, other compounds according to the invention can be linked by known standard methods.

b) X=an intermediate member

The methods given under a) are also used to carry out the linking of W—X to G or W to X—G. Expediently, the bile acid moiety is also employed here either protected or unprotected.

A preferred preparation process consists in reacting reactive forms of W with reactive forms of X—G. If appropriate, the removal of protective groups and the conversion of C-24 carboxyl into the compounds according to the invention follows after the linking.

The preparation of reactive bile acid building blocks X—G is given in reaction schemes 1–4 item c) using cholic acid as an example.

c) Preparation of reactive bile acid building blocks X—G using cholic acid as an example, schemes 1–4 Scheme 1: X—G without protective group

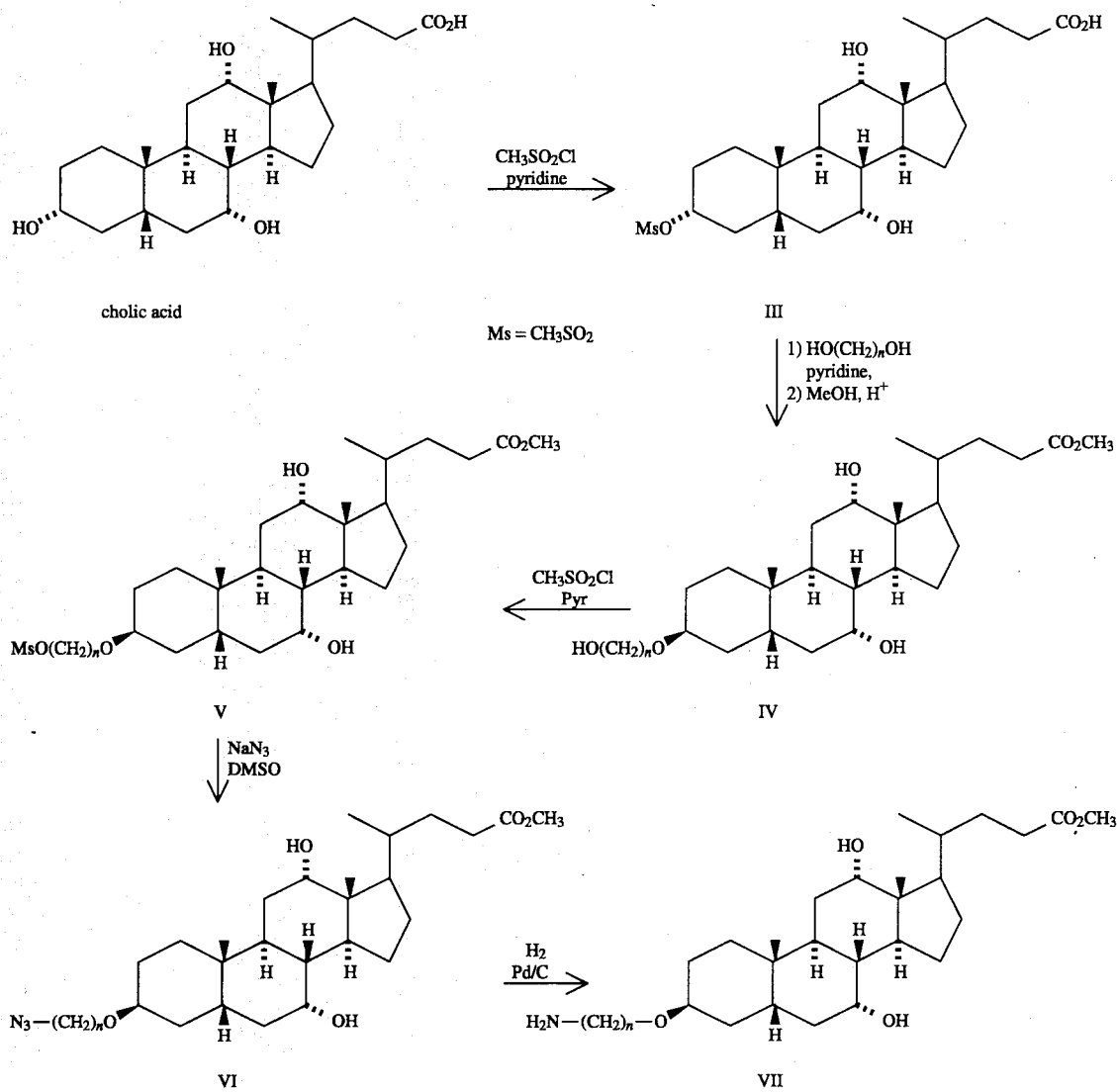
Scheme 1: X-G without protective group

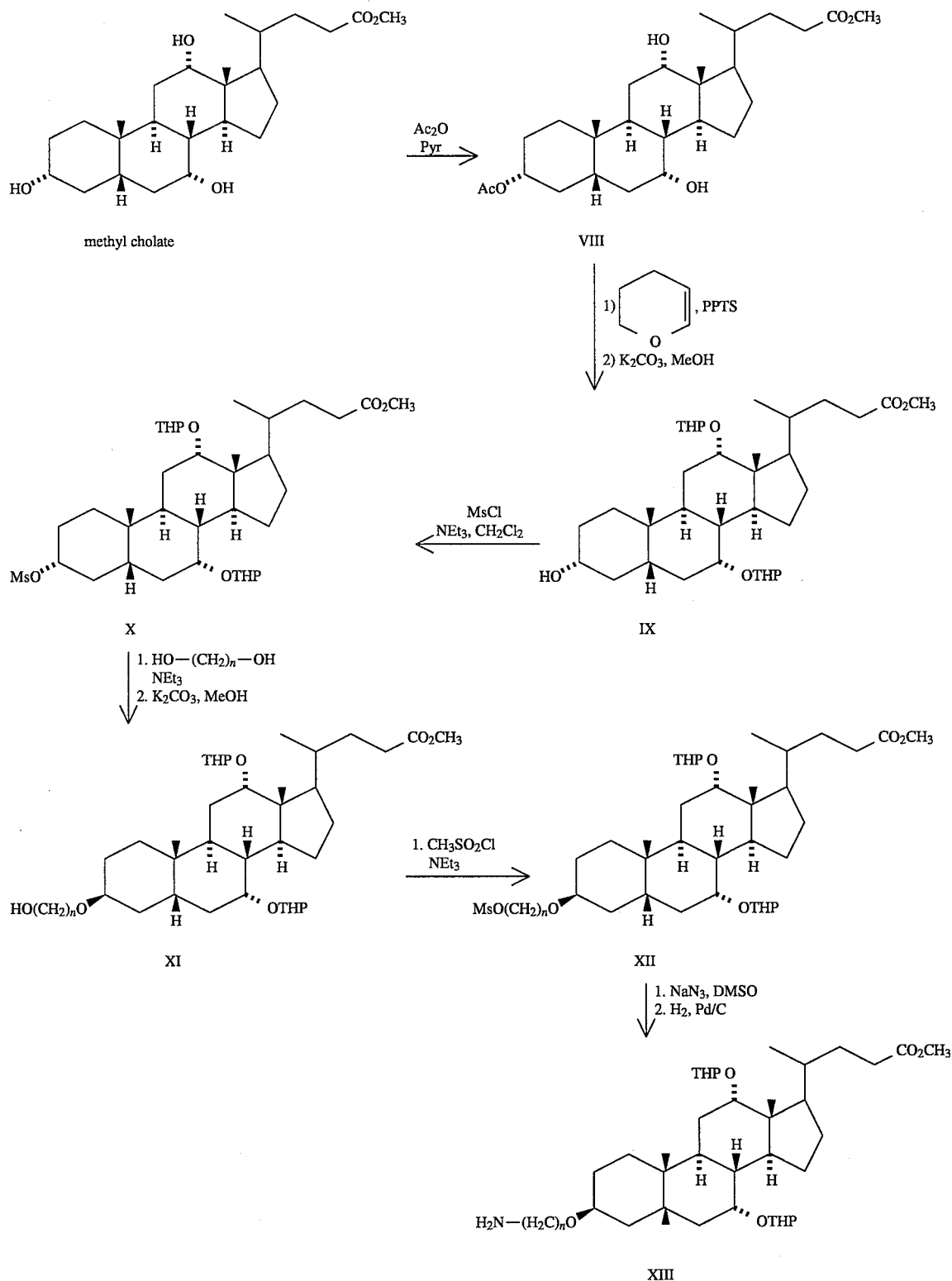
Scheme 2: X-G with THP protective group (THP = tetrahydropyranyl)

Scheme 3: X-G with t-BuMe₂Si protective group
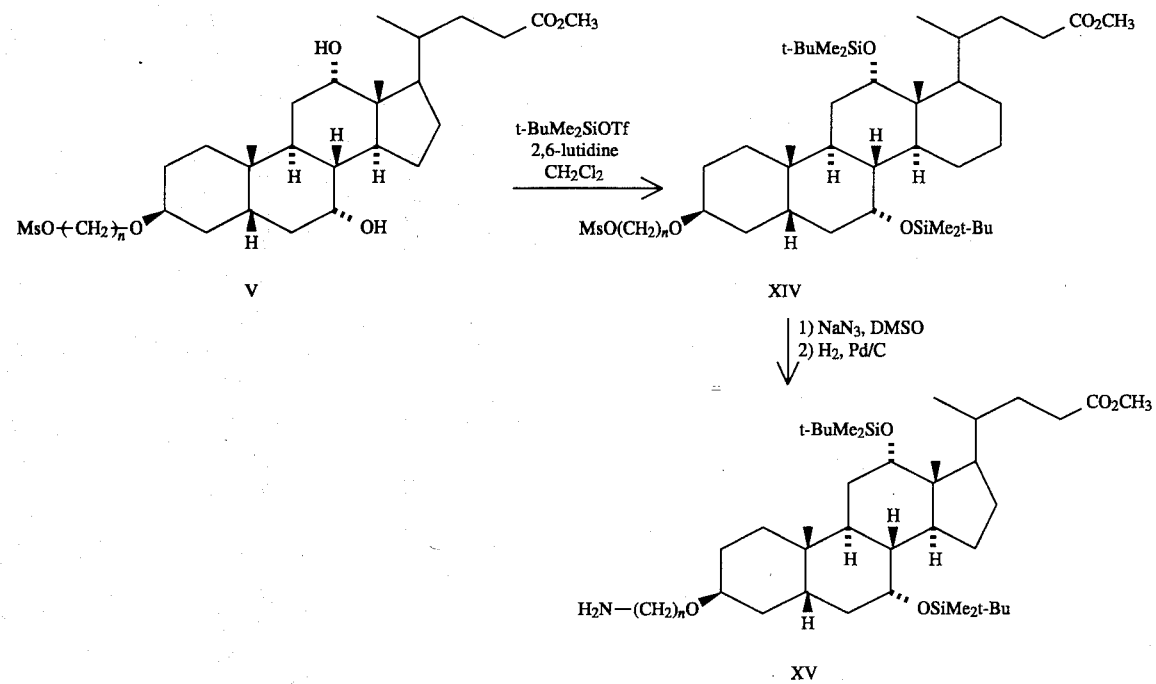
Scheme 4: X-G with α-configuration at 3-C
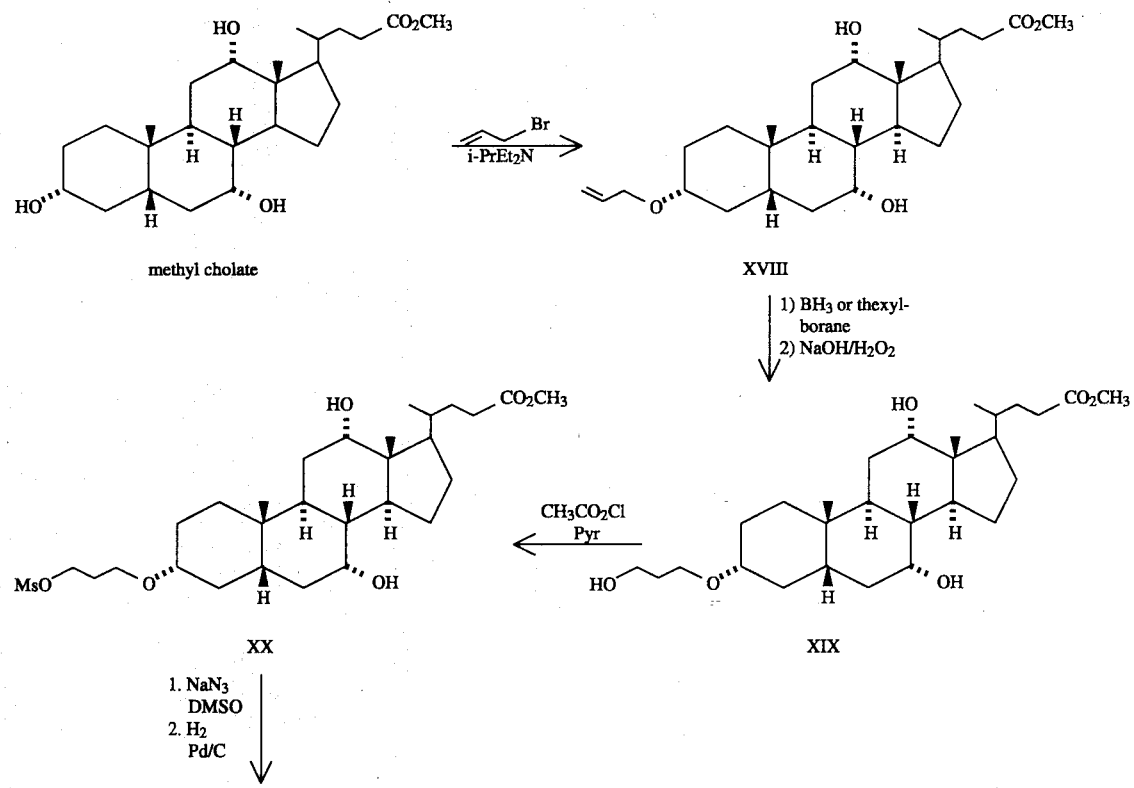

-continued
Scheme 4: X-G with α-configuration at 3-C

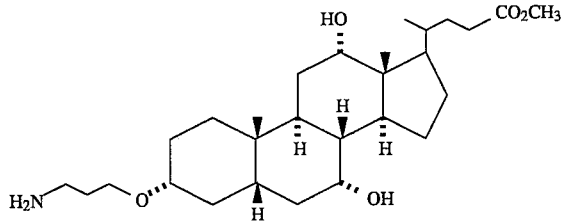

XXI

The replacement of the 3-OH groups by diols HO(CH$_2$)$_n$OH is carried out by reaction of the corresponding mesylates with the appropriate diols, which are preferably employed in excess, with the addition of bases such as pyridine, lutidine, but also triethylamine.

The primary OH groups of the compounds IV and XI can be reacted further by standard methods. Thus, for example, XI can be converted with oxidizing agents into the corresponding carboxylic acid XVI [where R(11) is equal to THP], preferably with chromium(VI) reagents or various potassium permanganate systems. Correspondingly, other protective groups are also suitable.

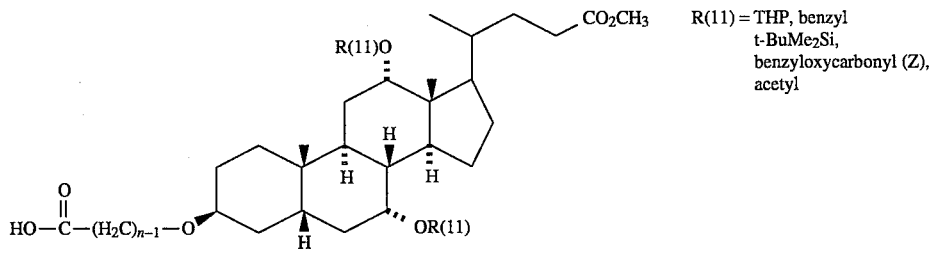

R(11) = THP, benzyl
t-BuMe$_2$Si,
benzyloxycarbonyl (Z),
acetyl

The amines VII, XIII and XV can be converted into carboxylic acids XVII using succinic anhydride in suitable solvents, preferably methylene chloride, toluene or, alternatively, pyridine.

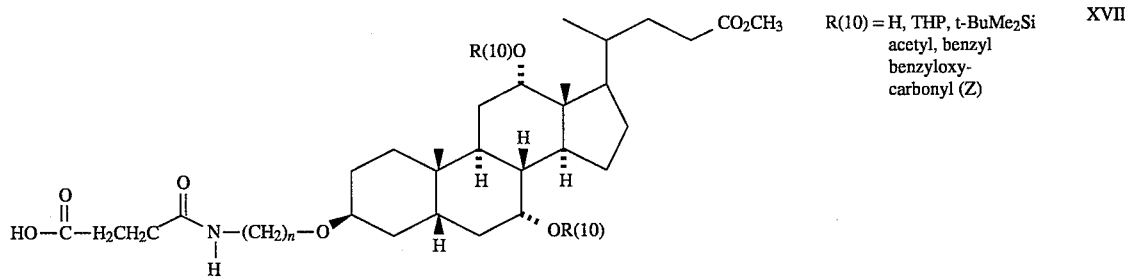

XVII
R(10) = H, THP, t-BuMe$_2$Si
acetyl, benzyl
benzyloxy-
carbonyl (Z)

Scheme 4 describes the preparation of bile acid building blocks having the 3α-configuration. Various boranes such as BH$_3$, thexylborane or 9-BBN are suitable for the hydroboration of XVIII. XVIII can be employed either protected on the alcohol groups as in Scheme 4 or, alternatively, protected with THP, acetyl, benzyl and the like.

Use as pharmaceuticals

Bile acids play an important physiological role in the digestion of lipids. They are supplied to the intestine from the liver via the gall bladder and there display their physiological action in the digestion of lipids. The largest part of the secreted bile acids is recovered again via the enterohepatic circulation. They reach the liver again via the mesenteric veins of the small intestine and the portal vein system. In the reabsorption in the intestine, both active and passive transport processes play a role. In the enterohepatic circulation, the bile acids manifest themselves both as free acids, but also in the form of glycine and taurine conjugates.

It has been found that the compounds I according to the invention are absorbed and pass into the bloodstream. In this way it is possible, using the natural reabsorption mechanisms of bile acids, to achieve an improved absorption of non-absorbable or poorly absorbable pharmaceuticals.

Moreover, this system possesses another important property: it allows pharmaceuticals, in particular nonabsorbable or absorbable pharmaceuticals, to achieve an organ-selective action namely with respect to those organs which possess transport mechanisms for bile acids, such as is the case, for example, in the tissues of the enterohepatic circulation (for example hepatotropic action). As a result, the systemic side effects of a number of pharmaceuticals can be specifically reduced or even prevented.

Improved absorption or an organ-selective action is desirable for a number of pharmaceuticals such as, for example, peptides, antibiotics, antiviral substances, anticancer agents, hepatoprotective agents, antihyperlipidemics, diuretics, hypotensives, renin inhibitors, prolylhydroxylase inhibitors and antidiabetics.

The pharmacologically active molecules can display their activity in various ways:

in the linked form W—X—G according to the invention after removal of the bile acid radical having a connecting member X in a free form W without X and G simultaneously in the three cases mentioned The compounds of the formula I are administered in various dosage forms, preferably orally in the form of tablets, capsules or liquids. The daily dose varies, depending on the body weight and constitution of the patient, in the range from 3 mg to 5000 mg, but preferably in the dose range 10–500 mg. The compounds according to the invention can be used dissolved or suspended in pharmacologically acceptable organic solvents, such as monohydric or polyhydric alcohols, such as, for example, ethanol or glycerol, in triacetin, oils such as, for example, sunflower oil, cod liver oil, ethers, such as, for example, diethylene glycol dimethyl ether or, alternatively, polyethers such as, for example, polyethylene glycol, or, alternatively, in the presence of other pharmacologically acceptable polymer carriers, such as, for example, polyvinylpyrrolidone, or other pharmaceutically acceptable additives such as starch, cyclodextrin or polysaccharides. The compounds according to the invention can further be administered in combination with other pharmaceutical substances.

The invention further relates to intermediates XXII

SG—X—G          XXII in which SG is equal to H, or a customary protective group, for example tetrohydropyranyl, benzyl, t-BuMe$_2$Si, benzyloxycarbonyl (Z) or acetyl, and G and X have the following meanings:

G is

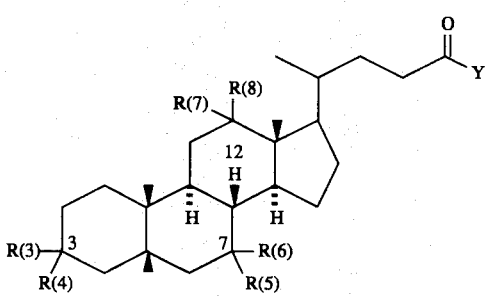

II in which R(3)–R(8) are identical or different and have the following meaning:

R(3) and R(4), R(5) and R(6), R(7) and R(8) in each case are jointly the oxygen of a carbonyl group, H, —OL, —SL, —NHL, —NL$_2$,

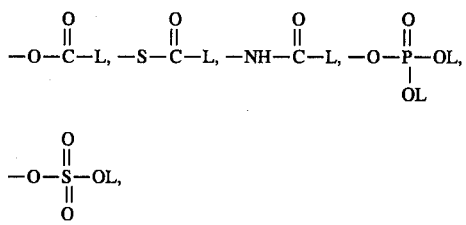

H, a saturated or unsaturated alkyl radical having 1–10 carbon atoms, which is branched or unbranched, cycloalkyl having 3–8 carbon atoms, a phenyl radical (which is unsubstituted or monosubstituted to trisubstituted by F, Cl, Br, (C$_1$–C$_4$)-alkyl or (C$_1$–C$_4$)-alkoxy), a benzyl radical (which is unsubstituted or monosubstituted to trisubstituted by F, Cl, Br, (C$_1$–C$_1$)-alkyl or (C$_1$–C$_8$)-alkoxy), —SiA(1)A(2)A(3) where A(1) to A(3) are identical or different, or equal to (C$_1$–C$_6$)-alkyl or phenyl, and in which Y has the following meaning —OL, —NHL, —NL$_2$, where L has the abovementioned meaning, an amino acid or aminosulfonic acid bonded via the amino group and its (C$_1$–C$_4$)-alkyl esters and alkali metal and alkaline earth metal salts, —OKa, where Ka is a cation such as, for example, an alkali metal or alkaline earth metal ion or, alternatively, a quaternary ammonium ion, the connecting member X is

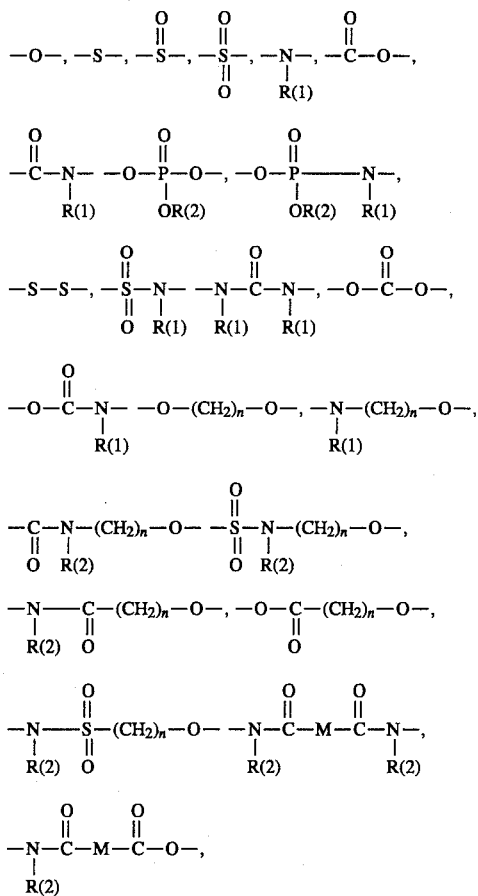

-continued

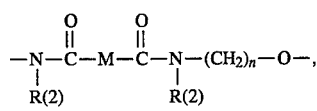

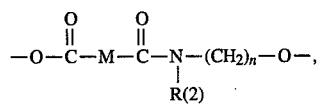

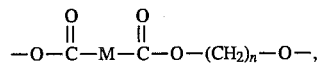

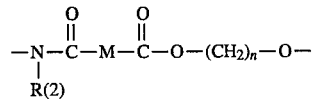

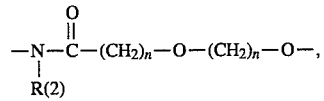

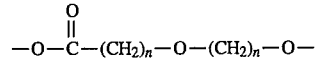

where
R(1)=H, $(C_1-C_8)$-alkyl, the group

phenyl, benzyl, unsubstituted or monosubstituted to trisubstituted in the nucleus by F, Cl, Br, $(C_1-C_4)$-alkyl, or alkoxy having 1–4 carbon atoms;
R(2)=H, $(C_1-C_8)$-alkyl, phenyl, benzyl; in each case unsubstituted or monosubstituted to trisubstituted by F, Cl, Br, $(C_1-C_4)$-alkyl or alkoxy having 1–4 carbon atoms,
n=1–16 and
M=$—(CH_2)_m—$ where m=2.

These intermediates are usually employed for the invention as compounds XXII having a free $NH_2$ or $^-OH$ group SG if it is intended to react them to give compounds I W—X—G.

The protective group SG is mainly present during the synthesis of the compounds I and XXII, but is usually converted into its form SG equal to hydrogen before the reaction of XXII to give I.

The intermediates SG—X—G are of great importance both for the preparation of the compounds I and for the synthesis of other final products, for example polymers with vinyl acetate which contain the group —X—G.

Preferred intermediates XXII are those with
G as defined above
SG equal to H and
X equal to
—$O(CH_2)_{2-10}$—O—,
—HN—$(CH_2)_{2-10}$—O—
—$O(CH_2)_{2-4}$—$O(CH_2)_{2-4}$—O—
—HN—$(CH_2)_{2-4}$—$O(CH_2)_{2-4}$—O—

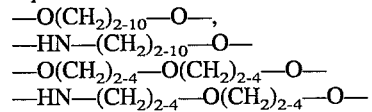

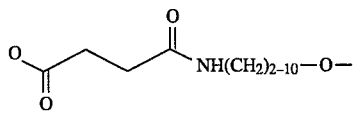

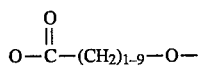

Particularly preferred compounds XXII are those with
G as defined above,
SG equal to H and
X equal to
—$O(CH_2)_{2-4}$—O— and
—HN—$(CH_2)_{2-10}$—O—.

EXAMPLES

1. W—X—G, X=a direct bond

Example 1

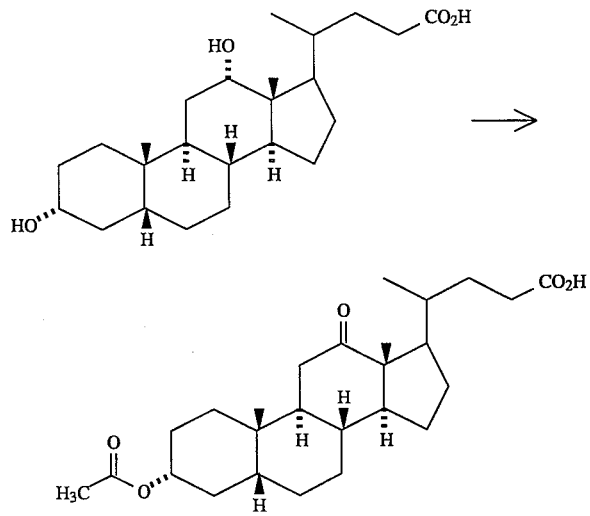

20 g (51 mmol) of deoxycholic acid were initially introduced in 50 ml of dioxane and 20 ml of pyridine and 30 ml of acetic anhydride were added at room temperature. After 3 days, the mixture was evaporated and the residue was dissolved in 300 ml of acetic acid. For oxidation, 14 g of potassium chromate in 60 ml of water were added. The mixture was allowed to stand at room temperature for 3 days. For working up, 4 l of water were added and the mixture was extracted using ether (3×). The combined organic phases were dried using sodium sulfate and evaporated. The residue was dissolved in 200 ml of 1N aqueous KOH. After 24 h, the product was precipitated using 1N HCl. Chromatography on silica gel (cyclohexane/ethyl acetate/acetic acid=40:100:1) gave 14.0 g (35.9 mmol, 70%) of "Example 1".

Example 2

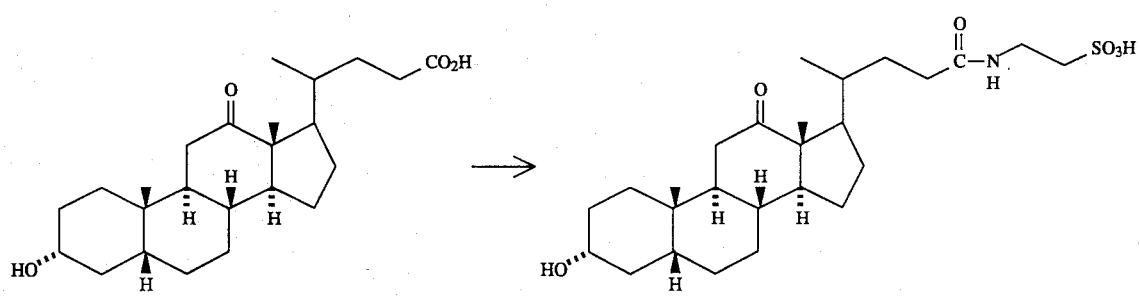

14.0 g (35.9 mmol) of "Example 1" were dissolved in 100 ml of dioxane and 8.3 ml of tri-n-butylamine were added. 3.75 ml of ethyl chloroformate were then added dropwise. After 30 min at room temperature, 4.75 g of taurine, dissolved in 38 ml of 1N NaOH, were added. After stirring for 24 h at room temperature, the mixture was evaporated and the residue was partitioned between 400 ml of 1N HCl and ether. The aqueous phase was extracted three times using ether. The combined organic phases were evaporated, the residue was taken up using hot ethanol, and the solution was filtered and concentrated, whereupon the product crystallized. Yield: 9.5 g of "Example 2"

Example 3

500 mg of chlorambucil in 25 ml of dioxane were converted into the acid chloride in the course of 24 h using 1.5 ml of oxalyl chloride at room temperature in the presence of 2 g of molecular sieve (4 Å). The mixture was evaporated and the residue was taken up using 15 ml of dry dioxane. This solution was added dropwise under $N_2$ in the course of 30 min to a boiling solution of 900 mg of "Example 2" in 60 ml of dioxane. After refluxing for 5 h, the mixture was evaporated and the residue was chromatographed on silica gel ($CHCl_3$/MeOH/HOAc=12:1:2) Yield: 250 mg of "Example 3"

Example 4

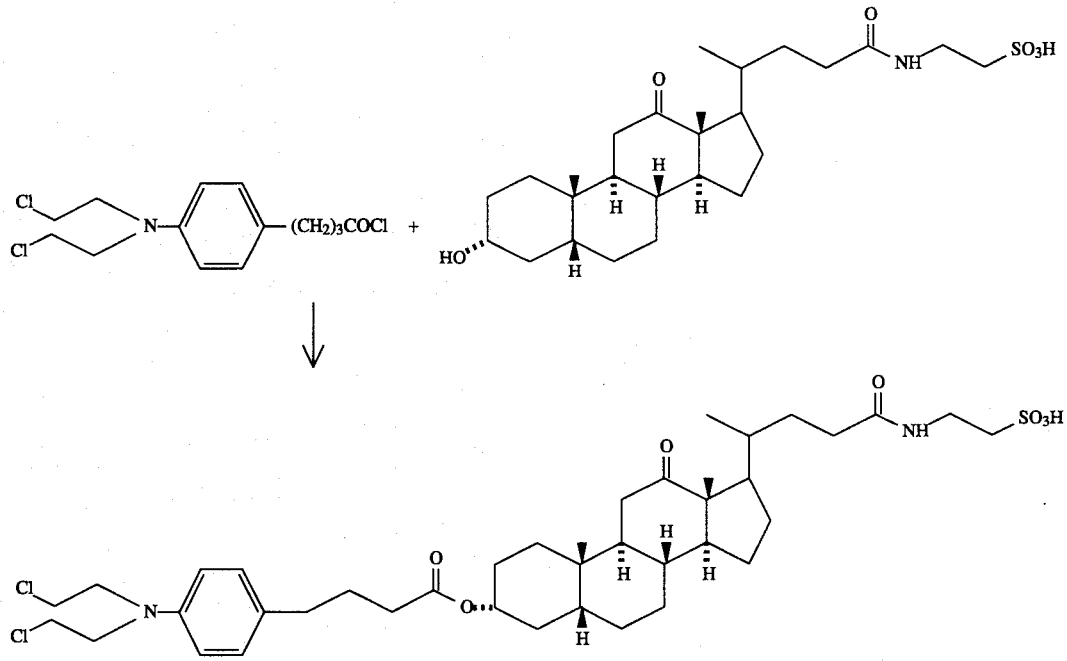

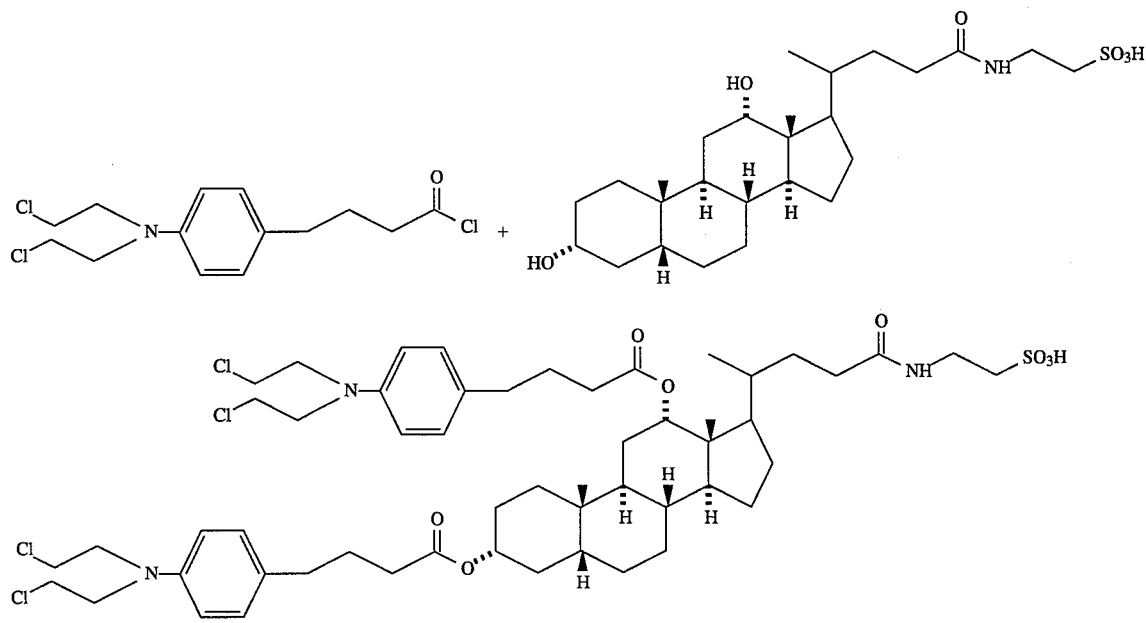

As described in Example 3, a solution of the acid chloride of chlorambucil was prepared from 500 mg of chlorambucil and reacted with 400 mg of deoxytaurocholic acid in the same way. Chromatography on silica gel (ethyl acetate/cyclohexane/HOAc=100:90:1; then CHCl₃/MeOH=5:1) gave 350 mg of "Example 4".

dioxane/15 µl (100 mmol) of pH 7.4 sodium phosphate buffer and added to 100 mCi of Na[³H]BH₄ (11.8 Ci/mmol). After 2 h at room temperature, 20 µl of 5N HCl were added. Preparative TLC (HPTLC TLC plate, 0.5 nun, butanol/HOAc/H₂O= 91:2) gave 2 mCi of "Example 5".

Example 5

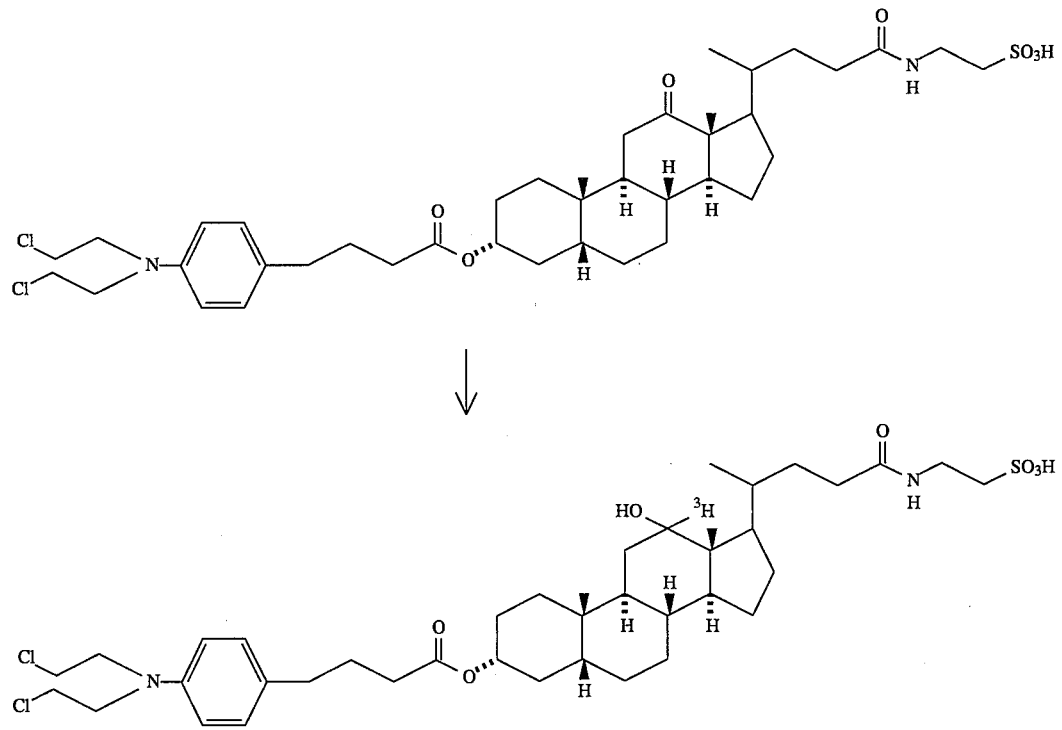

5 mg of "Example 3" were dissolved in 150 µl of

Example 6

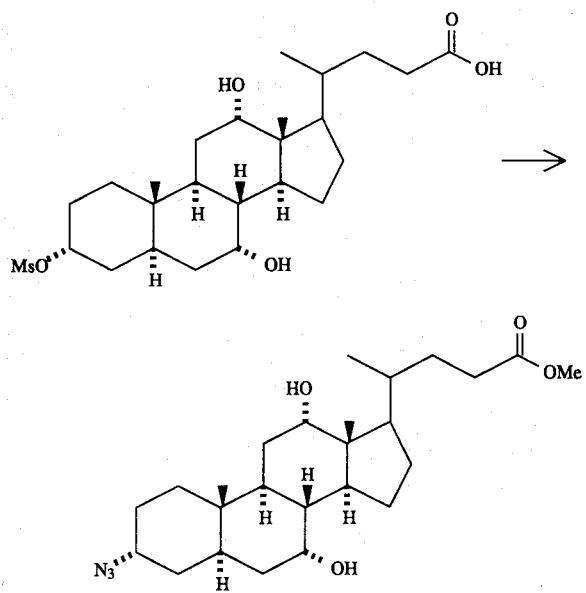

a) 6.2 g (95.4 mmol) of sodium azide were added to a solution of 43.6 g (89.6 mmol) of "Example 10" in 1 l of dry DMF and the mixture was stirred at 130° C. for 45 min. After cooling, the mixture was poured into water and extracted using diethyl ether (3×). The combined organic phases were dried using MgSO$_4$ and evaporated.

b) The esterification was carried out analogously to "Example 11b". Chromatography on silica gel (cyclohexane/ethyl acetate 1:1) gave 18.9 g (42.2 mmol, 47%) of azide "Example 6".

$C_{25}H_{41}N_3O_4$ (447) MS (FAB, 3-NBA/LiCl): 454 (M+Li$^+$)

Example 7

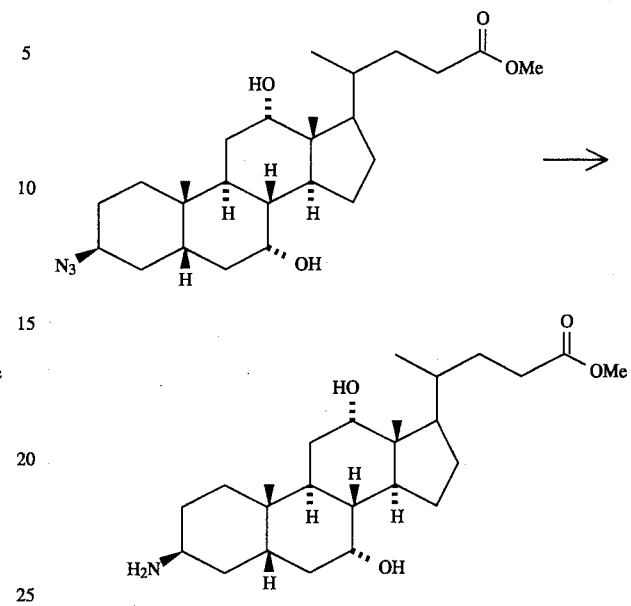

3.0 g (6.7 mmol) of "Example 6" were dissolved in 100 ml of MeOH and hydrogenated at room temperature and normal pressure using 2 g of Pd/C. The catalyst was filtered off and the filtrate was evaporated. Chromatography on silica gel (MeOH/NEt$_3$ 95:5) gave 1.6 g (3.8 mmol, 57%) of amine "Example 7".

$C_{25}H_{63}NO_4$ (421)MS (FAB): 422 (M+H$^+$).

Example 8

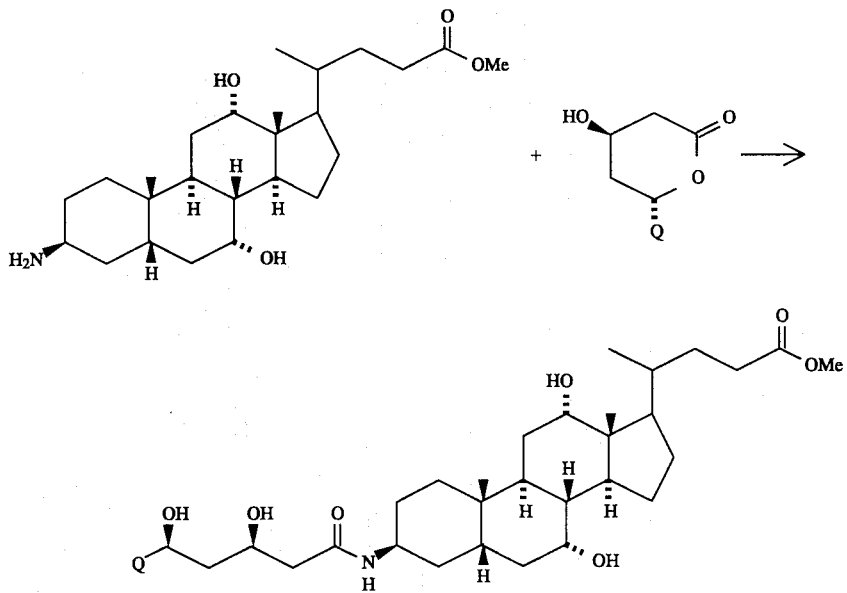

Q = 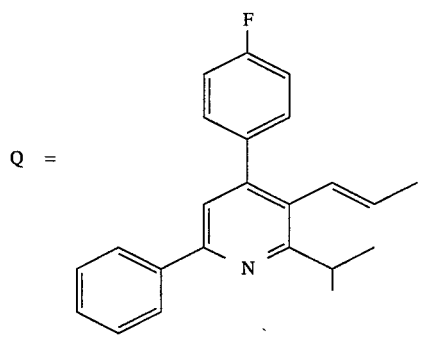

A mixture of 500 mg (1.19 mmol) of "Example 7", 10 ml of triethylamine, 200 mg (1.61 mmol) of 4-dimethylaminopyridine and 520 mg (1.20 mmol ) of lactone "Example 125" (preparation see DE 3,823,045-A, U.S. Pat. No. 4,925, 852) in 25 ml of dry THF was heated under reflux for 48 h. The solvent was evaporated and the residue was chromatographed on silica gel (chloroform/methanol 9:1). Yield 520 mg (0.61 mmol, 51%) of "Example 8".

$C_{22}H_{69}FN_2O_7$ (825), MS (FAB, 3-NBA/LiCl): 859 (M+Li$^+$).

Example 9

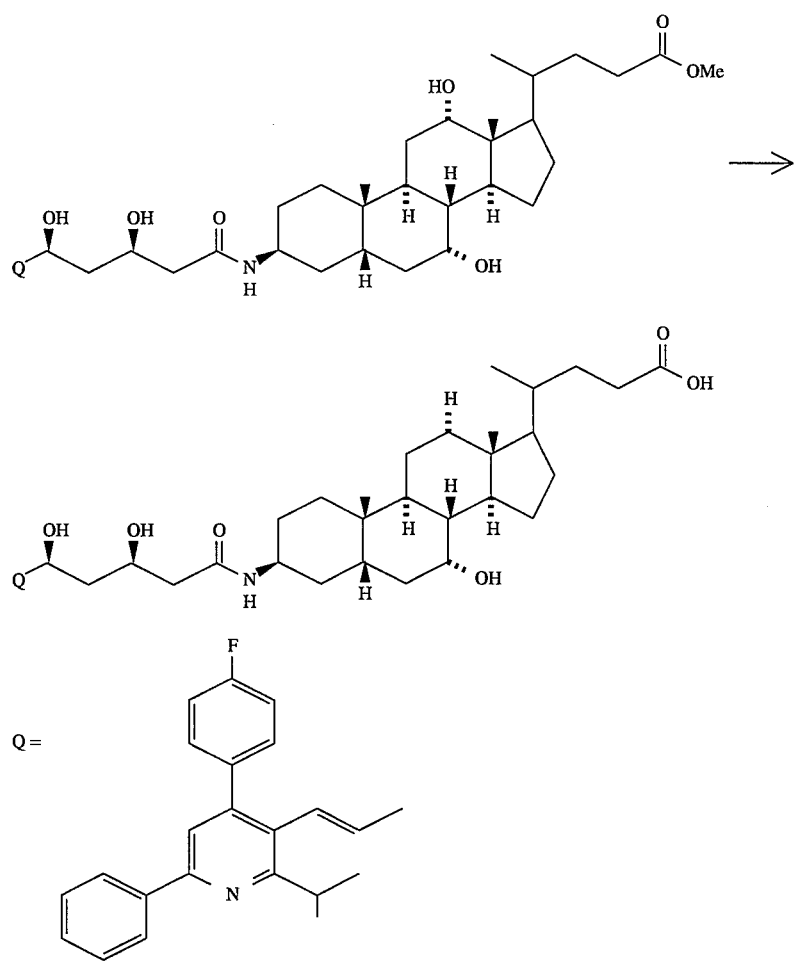

"Example 9" was obtained analogously to Examples 79–88.

$C_{51}H_{67}FN_2O_7$ (840), MS (FAB, 3-NBA/LiCl): 847 (M+Li$^+$).

2. X—G, X=an intermediate member

Example 10

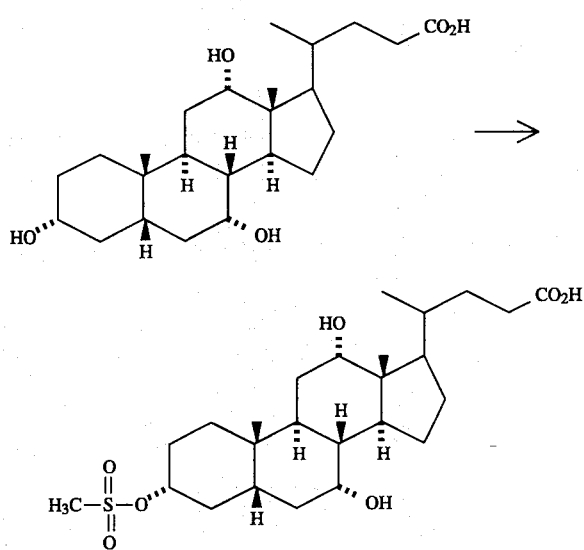

23.1 ml (0.294 mol) of methanesulfonyl chloride were added dropwise at 0° C. to 100 g (0.245 mol) of cholic acid in 500 ml of pyridine. The mixture was stirred at 0° C. for 30 min and at room temperature for 2 h. The mixture has poured into 3000 ml of water/400 ml of conc. $H_2SO_4$ and extracted using ethyl acetate (3×). The combined organic phases were dried using $MgSO_4$ and evaporated. Chromatography on silica gel (ethyl acetate/cyclohexane/HOAc= 55:1) gave "Example 10" quantitatively. For preparative purposes, a further purification was not necessary.

Example 11

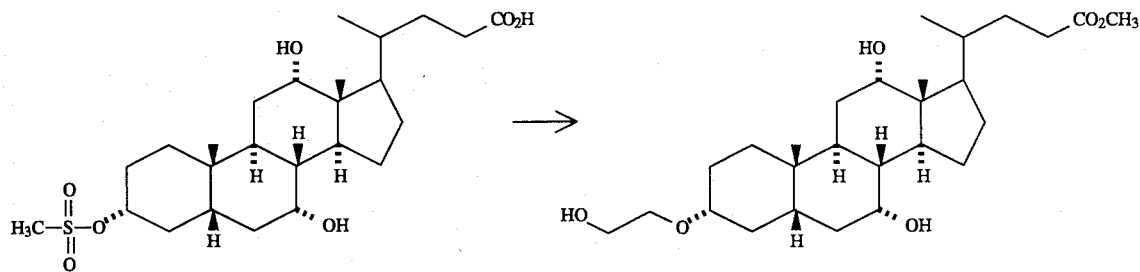

a) 119 g (0.245 mol) of "Example 10" were heated at 100° C. for 2 h in 500 ml of ethylene glycol/100 ml of pyridine. The mixture was poured into 1500 ml of water/100 ml of conc. $H_2SO_4$ and extracted using ethyl acetate (3×). The combined organic phases were dried ($MgSO_4$) and evaporated.

b) For esterification, the residue was dissolved in 1100 ml of methanolic HCl (prepared by dropwise addition of 100 ml of acetyl chloride to 1000 ml of methanol) and stirred overnight at room temperature. The solution was poured into 2000 ml of water and extracted using ether (3×). The combined organic phases were washed using saturated aqueous $NaHCO_3$ solution and dried ($MgSO_4$). Evaporation of the solvent and flash chromatography on silica gel (ethyl acetate then ethyl acetate/MeOH=10:1) gave 37.1 g (0.08 mol, 33%) of "Example 11".

$C_{27}H_{46}O_6$ (466), MS (FAB, 3-NBA/LiI): 473 (M+Li$^+$)

The product contains up to 10% of the 3α-isomer, which can optionally be removed after appropriate derivatization.

The compounds of Table 1 were prepared analogously to Example 11.

(The β-isomers were obtained predominantly in addition to relatively small proportions of the e-isomers).

TABLE 1

[Structure shown: steroid nucleus with HO at 12-position (α), H stereochemistry, R(3)/R(4) at 3-position, OH at 7-position (α), and methyl ester side chain at 17-position]

| Ex. | β-R(3) | α-R(4) | MS (FAB, 3-NBA/LiI or LiCl) |
|---|---|---|---|
| 12 | HO—(CH$_2$)$_3$—O— | H | C$_{28}$H$_{48}$O$_6$(480); 487 (M + Li$^+$) |
| 13 | HO—(CH$_2$)$_4$—O— | H | C$_{29}$H$_{50}$O$_6$(494); 501 (M + Li$^+$) |
| 14 | HO—(CH$_2$)$_5$—O— | H | C$_{30}$H$_{52}$O$_6$(508); 515 (M + Li$^+$) |
| 15 | HO—(CH$_2$)$_6$—O— | H | C$_{31}$H$_{54}$O$_6$(522); 529 (M + Li$^+$) |
| 16 | HO—(CH$_2$)$_{10}$—O— | H | C$_{35}$H$_{62}$O$_6$(578); 585 (M + Li$^+$) 601 (M + Na$^+$) |
| 17 | HO—(CH$_2$)$_2$—O—(CH$_2$)$_2$—O— | H | C$_{29}$H$_{50}$O$_7$(510); 517 (M + Li$^+$) |
| 18 | H$_3$C—CH(OH)—CH$_2$)—O— | H | C$_{28}$H$_{48}$O$_6$(480); 487 (M + Li$^+$) |

Example 19

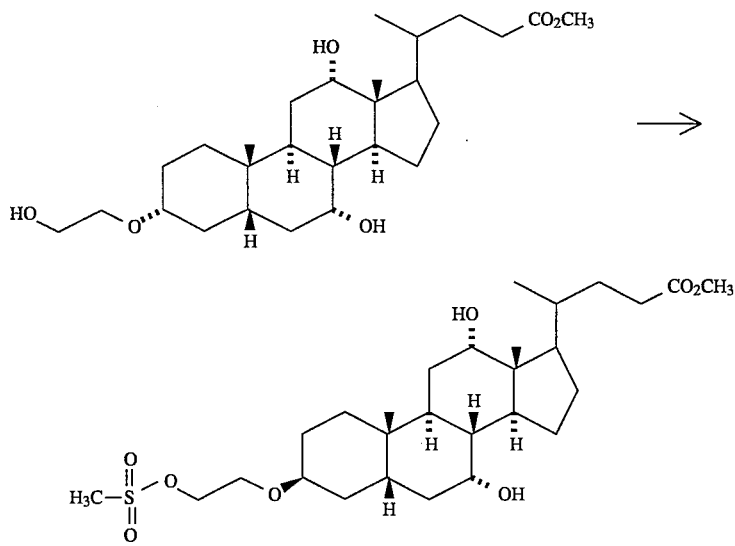

6.6 mol (0.084 mol) of methanesulfonyl chloride were added dropwise at 0° C. to 37.1 g (0.08 mol) of "Example 11" in 150 ml of pyridine. The mixture was stirred at 0° C. for 15 min and at room temperature for 1 h. The reaction mixture was poured into 500 ml of water and extracted using ethyl acetate (3×). Drying of the combined organic phases (MgSO$_4$), removal of the solvent and chromatography on silica gel (ethyl acetate/cyclohexane=3:1) gave 37.7 g (0.07 mol, 87%) of mesylate "Example 19".

C$_{26}$H$_{48}$O$_8$S (544), MS (FAB, 3-NBA/LiI): 551 (M+Li$^+$).

Example 20

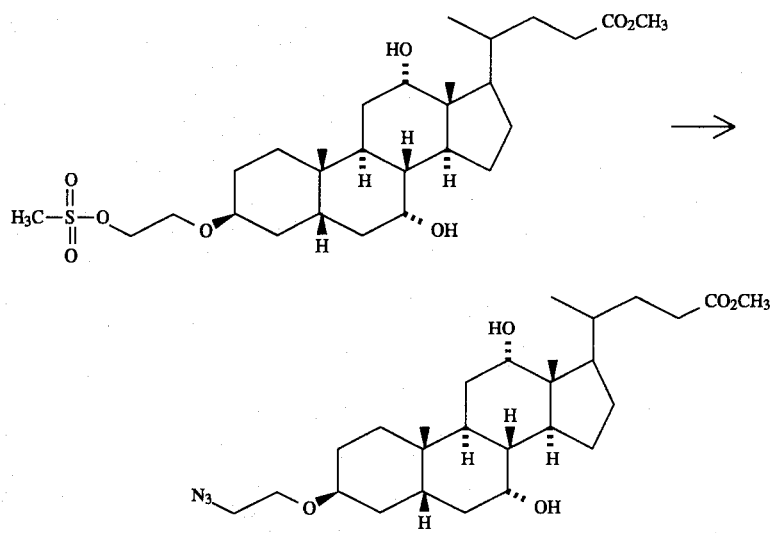

37.7 g (0.07 mol) of mesylate "Example 19" were stirred at 70° C. for 2 h with 4.95 g (0.076 mol) of sodium azide in 150 ml of dry DMSO. The reaction mixture was poured into water and extracted using ethyl acetate (3×). The combined organic phases were dried (MgSO$_4$) and evaporated. The residue was taken up using toluene and the toluene was removed again in a rotary evaporator (2×). Yield 34.5 g of "Example 20" (quantitative). The azide was reacted immediately to the next stage without further purification.

Example 21

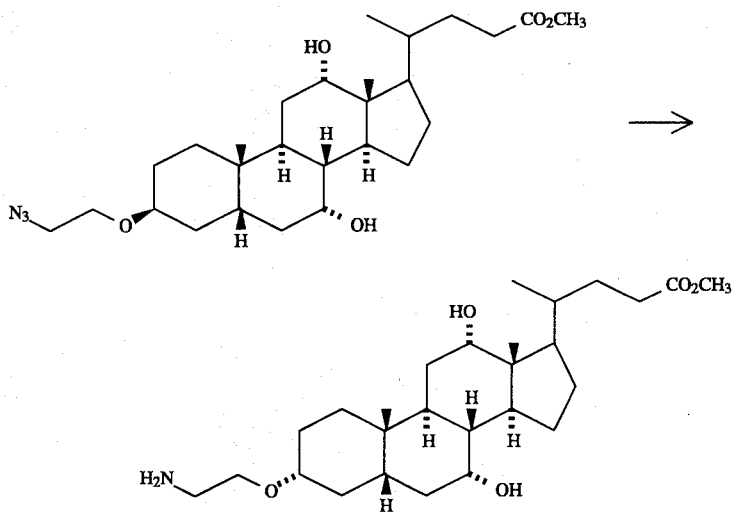

31.1 g (0.063 mol) of "Example 20" were hydrogenated at room temperature and normal pressure in 500 ml of ethyl acetate containing 20 g of Pd/C (10%). The catalyst was filtered off and the filtrate was evaporated. Chromatography on silica gel (ethyl acetate/methanol/NEt$_3$=5:1:1) gave 21.0 g (0.045 mol, 71%) of amine "Example 21".

$C_{27}H_{47}NO_5$ (465), MS (FAB, 3-NBA/LiI): 472 (M+Li$^+$).

The compounds of Table 2 were prepared analogously to Examples 19–21.

TABLE 2

[Structure: steroid nucleus with 12-OH, 7-OH (α), CO₂CH₃ side chain, and R(3)/R(4) at position 3]

| Ex. | β-R(3) | α-R(4) | MS (FAB, 3-NBA/LiI) |
|---|---|---|---|
| 22 | H₂N—(CH₂)₃—O— | H | $C_{28}H_{49}NO_5$(479); 486 (M + Li⁺) |
| 23 | H₂N—(CH₂)₄—O— | H | $C_{29}H_{51}NO_5$(493); 500 (M + Li⁺) |
| 24 | H₂N—(CH₂)₅—O— | H | $C_{30}H_{53}NO_5$(507); 514 (M + Li⁺) |
| 25 | H₂N—(CH₂)₆—O— | H | $C_{31}H_{55}NO_5$(521); 528 (M + Li⁺) |
| 26 | H₂N—(CH₂)₁₀—O— | H | $C_{35}H_{63}NO_5$(577); 584 (M + Li⁺) |
| 27 | H₂N—(CH₂)₂—O—(CH₂)₂—O— | H | $C_{29}H_{51}NO_6$(509); 516 (M + Li⁺) |
| 28 | H₃C—CH₂—CH₂—O—<br>        \|<br>      NH₂ | H | $C_{26}H_{49}NO_5$(479); 486 (M + Li⁺) |

In analogy to cholic acid, other bile acids were reacted according to Examples 10–28 and compounds according to Table 3 were obtained.

a) starting from deoxycholic acid:

TABLE 3

[Structure: steroid nucleus with 12-OH, CO₂CH₃ side chain, and R(3)/R(4) at position 3]

| Ex. | β-R(3) | α-R(4) | MS (FAB, 3-NBA/LiI) |
|---|---|---|---|
| 29 | HO—(CH₂)₂—O— | H | $C_{27}H_{46}O_5$(450); 457 (M + Li⁺) |
| 30 | HO—(CH₂)₃—O— | H | $C_{28}H_{48}O_5$(464); 471 (M + Li⁺) |
| 31 | HO—(CH₂)₅—O— | H | $C_{30}H_{52}O_5$(492); 499 (M + Li⁺) |
| 32 | HO—(CH₂)₁₀—O— | H | $C_{35}H_{62}O_5$(562); 569 (M + Li⁺) |
| 33 | H₂N—(CH₂)₂—O— | H | $C_{27}H_{47}NO_4$(449); 456 (M + Li⁺) |
| 34 | H₂N—(CH₂)₅—O— | H | $C_{30}H_{53}NO_4$(491); 498 (M + Li⁺) |

TABLE 4

| Ex. | β-R(3) | α-R(4) | MS (FAB, 3-NBA/LiI) |
|---|---|---|---|
| 35 | HO—(CH$_2$)$_2$—O— | H | C$_{27}$H$_{46}$O$_5$(450); 457 (M + Li$^+$) |
| 36 | HO—(CH$_2$)$_3$—O— | H | C$_{28}$H$_{48}$O$_5$(464); 471 (M + Li$^+$) |
| 37 | HO—(CH$_2$)$_5$—O— | H | C$_{30}$H$_{52}$O$_5$(492); 499 (M + Li$^+$) |
| 38 | HO—(CH$_2$)$_{10}$—O— | H | C$_{35}$H$_{62}$O$_5$(562); 569 (M + Li$^+$) |
| 39 | H$_2$N—(CH$_2$)$_2$—O— | H | C$_{27}$H$_{47}$NO$_4$(449); 456 (M + Li$^+$) |
| 40 | H$_2$N—(CH$_2$)$_5$—O— | H | C$_{30}$H$_{53}$NO$_4$(491); 498 (M + Li$^+$) |

TABLE 5

| Ex. | β-R(3) | α-R(4) | MS (FAB, 3-NBA/LiI) |
|---|---|---|---|
| 41 | HO—(CH$_2$)$_2$—O— | H | C$_{27}$H$_{46}$O$_4$(434); 441 (M + Li$^+$) |
| 42 | HO—(CH$_2$)$_3$—O— | H | C$_{28}$H$_{48}$O$_4$(448); 455 (M + Li$^+$) |
| 43 | HO—(CH$_2$)$_5$—O— | H | C$_{30}$H$_{52}$O$_4$(476); 483 (M + Li$^+$) |
| 44 | HO—(CH$_2$)$_{10}$—O— | H | C$_{35}$H$_{62}$O$_4$(546); 653 (M + Li$^+$) |
| 45 | H$_2$N—(CH$_2$)$_2$—O— | H | C$_{27}$H$_{47}$NO$_3$(433); 440 (M + Li$^+$) |
| 46 | H$_2$N—(CH$_2$)$_5$—O— | H | C$_{30}$H$_{53}$NO$_3$(475); 482 (M + Li$^+$) |

Example 47

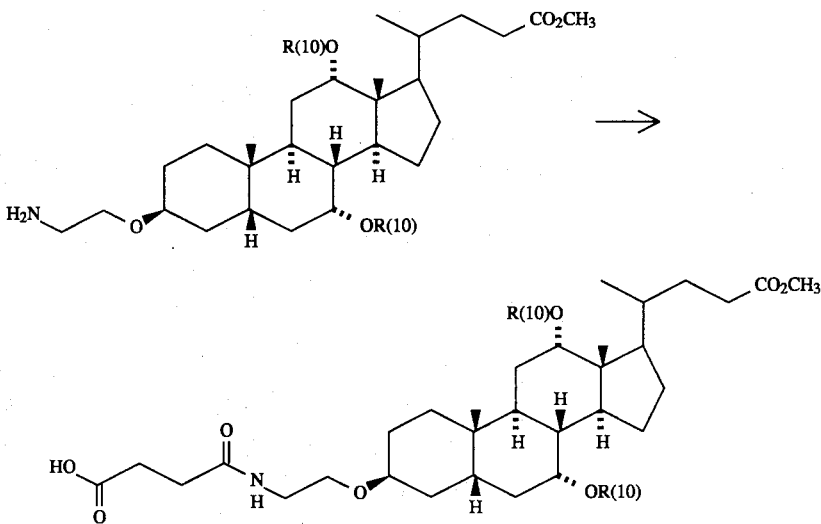

Example 47 a) (R(10)=H)

2.0 g (4.3 mol) of "Example 21" were stirred for 30 min at room temperature with 430 mg (4.3 mmol) of succinic anhydride in 25 ml of THF/5 ml of triethylamine. The reaction mixture was poured into 2N HCl and extracted using ethyl acetate (3×). Drying of the combined organic phases (MgSO₄) and removal of the solvent gave 2.4 g (4.2 mol, 98%) of "Example 47a" (R(10)=H)

$C_{31}H_{51}NO_8$ (565): MS (FAB, 3-NBA/LiI): 578 (M+2Li⁺—H)

Example 47 b) (R(10)=t-BuMe₂Si)

"Example 47 b)" was obtained from "Example 58" completely analogously to 47 a).

Example 47 c) (R(10)=tetrahydropyranyl=THP)

"Example 47 c)" was obtained from "Example 55" completely analogously to 47 a).

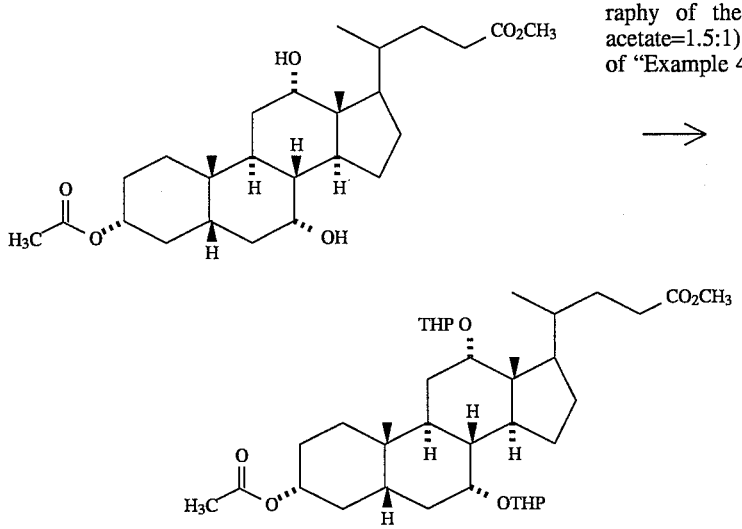

Example 48

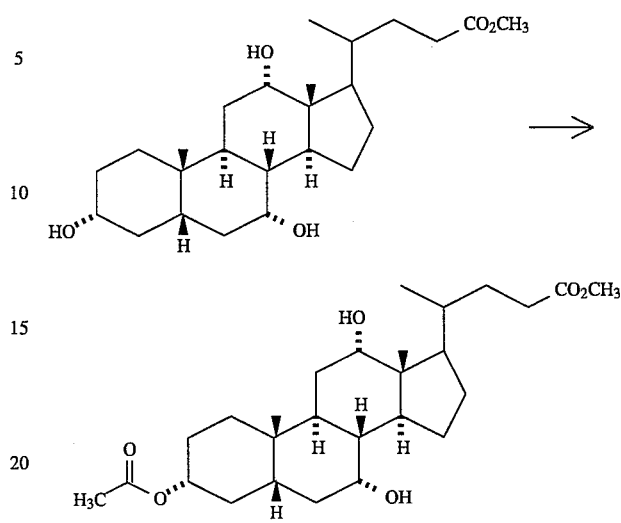

20.3 ml (0.284 mol) of acetyl chloride were added dropwise at 0° C. to 100 g (0.237 mol) of methyl cholate in 750 ml of pyridine. After stirring at room temperature for 2 h, 3.4 ml (0.047 mol) of acetyl chloride were added again at 0° C. and the mixture was stirred at room temperature for a further 1 h. The reaction mixture was poured into ice water and extracted using ethyl acetate (3×). The combined organic phases were dried (MgSO₄⁻) and evaporated. Chromatography of the residue on silica gel (cyclohexane/ethyl acetate=1.5:1) gave 95.8 g (0.206 mol, 87%) of monoacetate of "Example 48".

Example 49

50.0 g (0.108 mol) of monoacetate of "Example 48" were dissolved in 250 ml of dichloromethane/250 ml of dihydropyran and 10.0 g of pyridinium toluene-4-sulfonate were added at room temperature and the mixture was stirred for two days at room temperature. The reaction solution was diluted using 1500 ml of diethyl ether, the organic phase was washed twice with half-saturated aqueous sodium chloride solution and dried using MgSO₄. Removal of the solvent gave 75 g (quant.) of bis-THP ether "Example 49", which was used for the next step without further purification.

Example 50

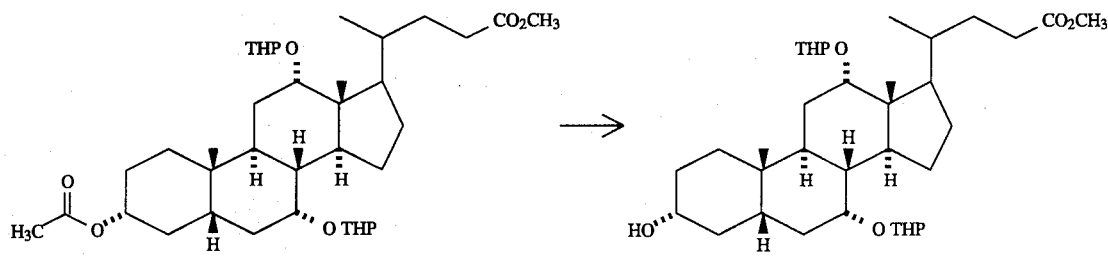

37.8 g (0.275 mol) of potassium carbonate were added at room temperature to 46.6 g (about 0.055 mol) of "Example 49" in 300 ml of dry methanol and the mixture was stirred for 3 h. The solvent was largely removed and the residue was poured into 2N hydrochloric acid/toluene. The aqueous phase was extracted twice using toluene and the combined organic phases were washed once with water and twice with saturated aqueous NaHCO$_3$ solution. Drying with MgSO$_4$, removal of the solvent and chromatography on silica gel (cyclohexane/ethyl acetate=3:2) gave 28.8 g (0.049 mmol, 89%) of "Example 50".

$C_{35}H_{58}O_7$ (590), MS (FAB, 3-NBA/LiI): 597 (M+Li$^+$)

Example 51

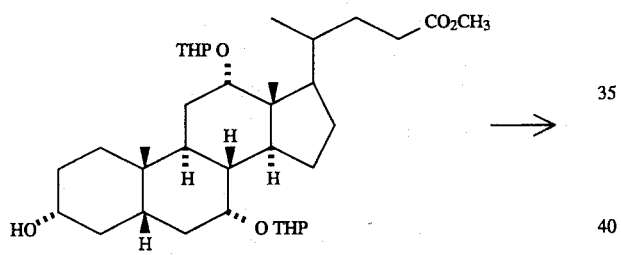

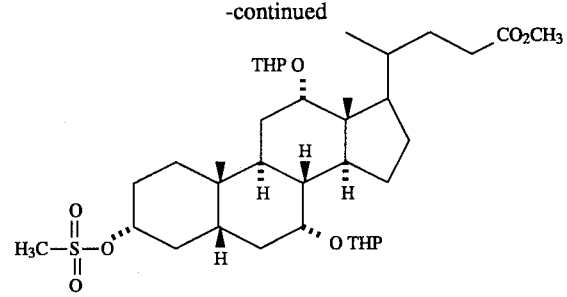

30.3 g (0.045 mol, 94%) of mesylate "Example 51" were obtained from 28.8 g (0.048 mol) of "Example 50" in analogy to Example 10.

Example 52

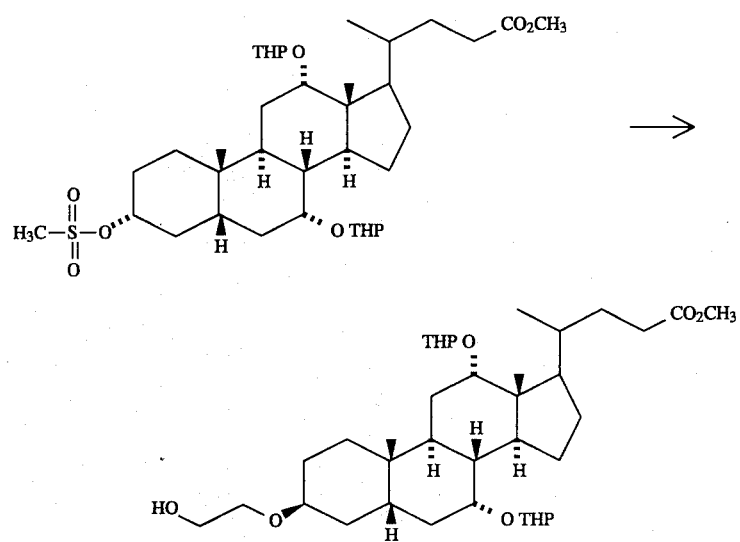

a) 46.0 g (0.068 mol) of mesylate "Example 51" were heated under reflux for 2.5 h with 300 ml of ethylene glycol/75 ml of triethylamine. The reaction mixture was poured into 1N hydrochloric acid and extracted using diethyl ether (2×). The combined organic phases were washed once with water, twice with saturated aqueous sodium hydrogen carbonate solution, dried (MgSO$_4$) and freed from solvent. The residue was taken up using toluene and the solution was evaporated (2×).

b) The residue was dissolved in 500 ml of dry methanol, 40.0 g of potassium carbonate were added and the mixture was stirred at room temperature for 1.5 h. The reaction mixture was largely freed from methanol in vacuo and the residue was poured into 2N hydrochloric acid/toluene. The aqueous phase was extracted twice using toluene, and the combined organic phases were washed once with saturated aqueous sodium hydrogen carbonate solution, dried (MgSO$_4$) and evaporated. Flash chromatography on silica gel (cyclohexane/ethyl acetate=2:1) gave 25.6 g (0.040 mol, 60%) of "Example 52".

$C_{37}H_{62}O_8$ (634), MS (FAB, 3-NBA, 3-NEA/LiI): 641 (M+Li$^+$).

Example 53

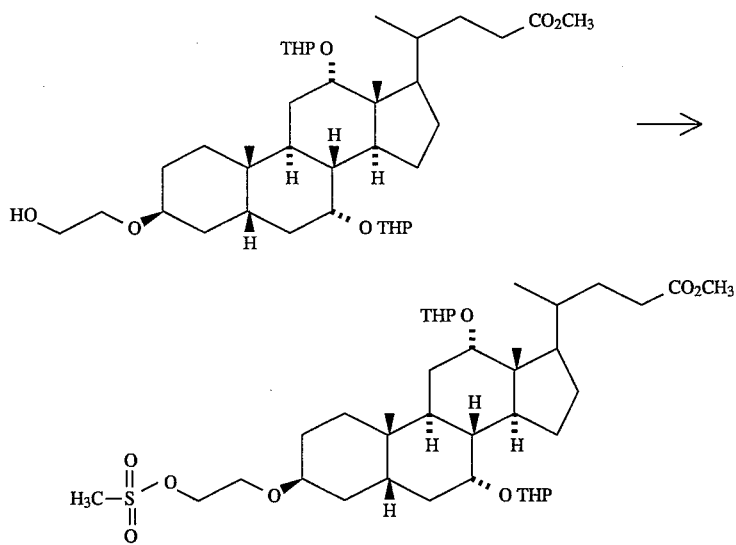

"Example 53" was obtained in analogy to Example 19.

Example 54

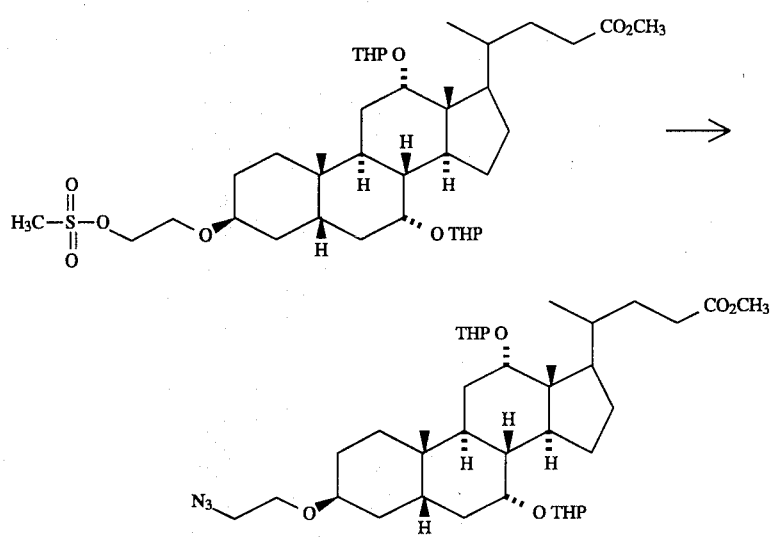
"Example 54" was obtained in analogy to Example 20.
Example 55
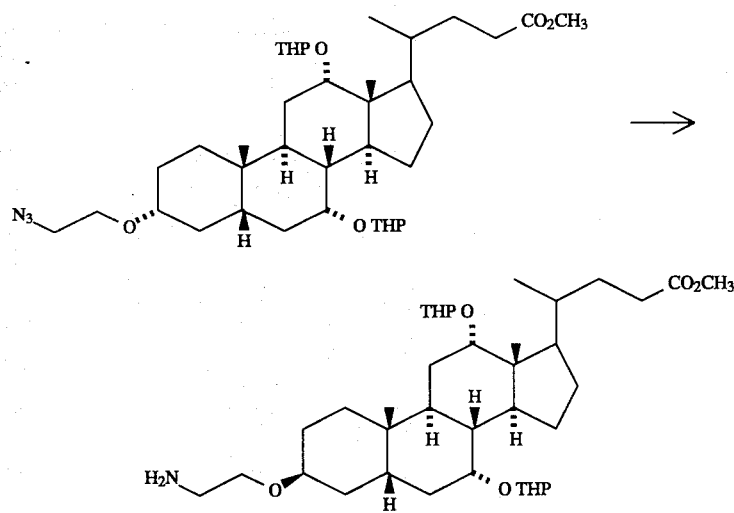
"Example 55" was obtained in analogy to Example 21.
$C_{37}H_{63}NO_7$ (633), MS (FAB, 3-NBA/LiI): 640 (M+Li$^+$).
Example 56

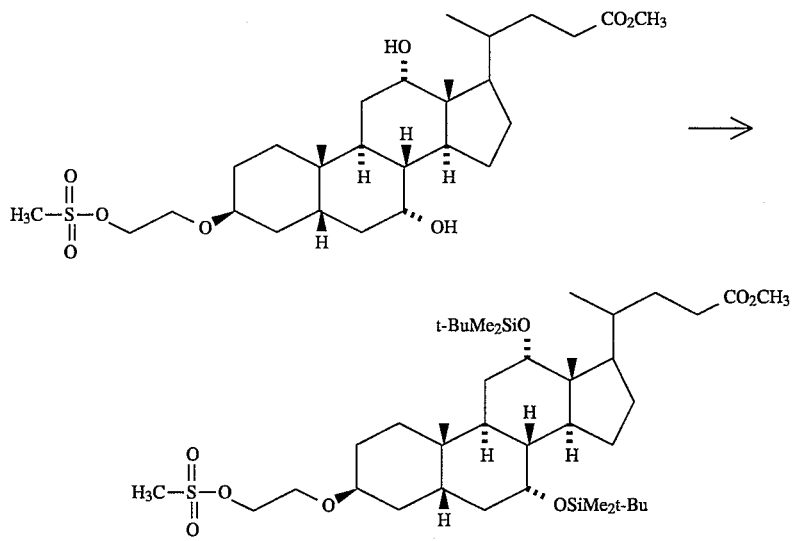

31.2 ml (0.136 mol) of tert-butyldimethylsilyl triflate were added dropwise at 0° C. to a solution of 24.5 g (0.045 mol) of "Example 19" and 26.4 ml (0.227 mol) of 2,6-dimethylpyridine in 150 ml of dichloromethane. The mixture was stirred at 0° C. for 15 min and at room temperature for 2 h. The reaction mixture was poured into saturated aqueous $NaHCO_3$ solution and extracted using dichloromethane (3×). The combined organic phases were dried using magnesium sulfate and evaporated. Flash chromatography on silica gel (ethyl acetate/cyclohexane=1:3) gave 23.5 g (0.03 mol, 67%) of "Example 56".

$C_{40}H_{76}O_8Si_2S$ (772), MS (FAB, 3-NBA/LiI): 779 (M+Li$^+$)

Example 20.

Example 58

Example 57

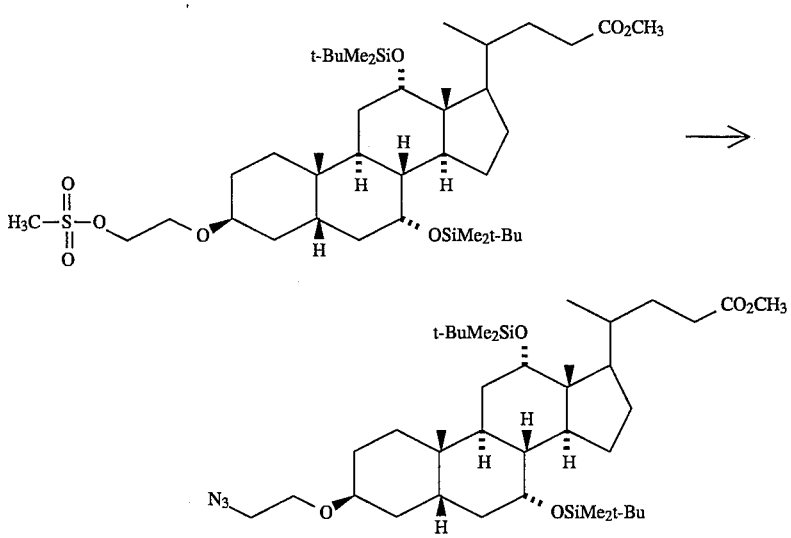

23.4 g (0.03 mol) of "Example 56" were converted quantitatively into the azide "Example 57" analogously to

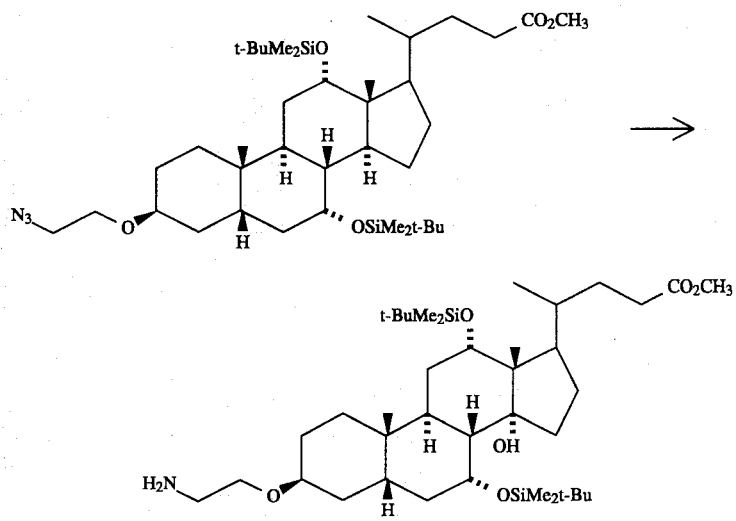

The azide "Example 57" was hydrogenated in analogy to Example 21. Yield after chromatography on silica gel (ethyl acetate/MeOH/NEt$_3$=18:1:1) 10.0 g (0.014 mmol, 48% relative to 0.03 mol of "Example 56".

C$_{39}$H$_{75}$NO$_5$Si$_2$ (693), MS (FAB, 3-BNA/LiI): 700 (M+Li$^+$)

benzyl ester "Example 59".

C$_{33}$H$_{51}$NO$_5$ (541), MS (FAB): 542 (M+H$^+$).

Example 59

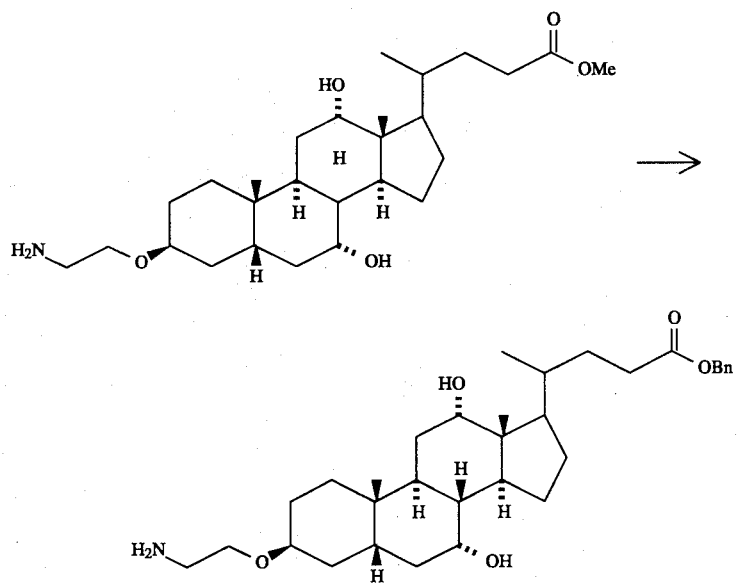

Bn = benzyl

A solution of 500 mg (1.07 mmol) of "Example 21" and 76 mg (0.33 mmol) of tetraethyl orthotitanate in 10 ml of dry benzyl alcohol was stirred at 100° C. for 8 h. After cooling, 100 ml of ethyl acetate were added. The mixture was extracted by shaking with 1N HCl (1×) and 8% NaHCO$_3$ solution (1×). The organic phase was dried using MgSO$_4$ and evaporated. Chromatography on silica gel (ethyl acetate/methanol/NEt$_3$5:1:1) gave 360 mg (6.64 mmol, 62%) of

Example 60

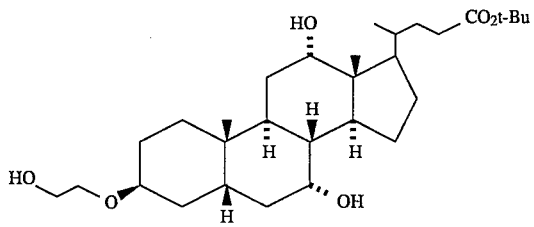

Example 60a

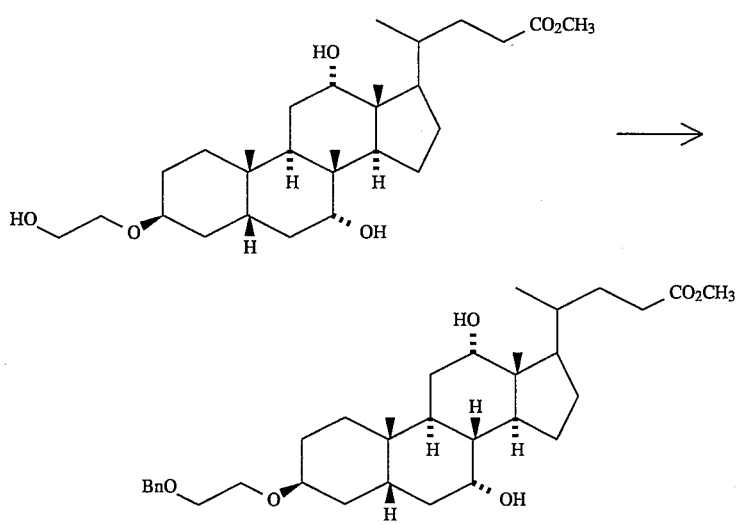

Bn = benzyl

Example 60b propylamine at 100° C. (bath temperature) for 3 h. The reaction product was then poured into a mixture of 1.8 liters of water and 180 ml of concentrated sulfuric acid and extracted using ethyl acetate (2×). The combined organic phases were washed once each with 1N hydrochloric acid, water and saturated aqueous NaHCO₃ solution, dried over MgSO₄ and evaporated.

Chromatography of the residue on silica gel using ethyl acetate/cyclohexane=1:1 gave 14.54 g (0.026 mol, 29.0%) of "Example 60a".

$C_{34}H_{52}O_6$ (556), MS (FAB, 3-NBA/LiCl): 563/M+Li⁺)

42 g (0.09 mol) of "Example 11" were stirred with 61.5 g (0.36 mol) of benzyl bromide in 270 ml of N-ethyldiiso-

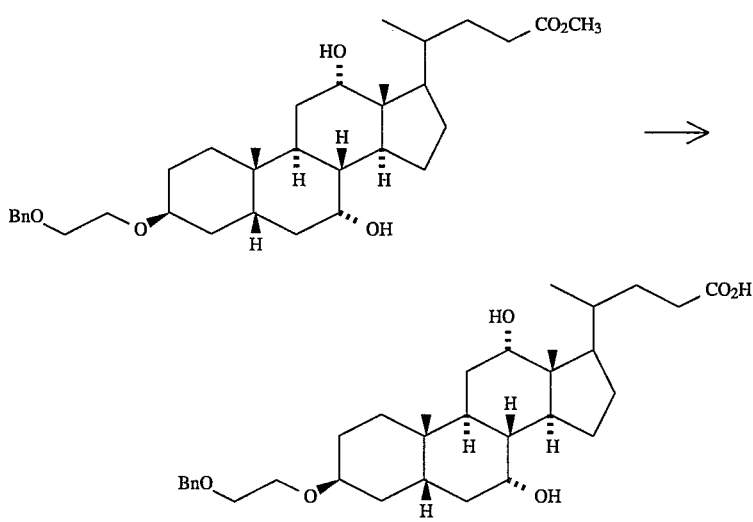

16.14 g (0.029 mol ) of Example 60a were dissolved in 450 ml of methanol, 37 ml (0.037 mol) of 1N aqueous sodium hydroxide solution were added and the mixture was heated under reflux for 8 h. The methanol was then removed on a rotaryevaporator, the residue was dissolved in 320 ml of water and 37 ml (0.037 mol) of 1N aqueous hydrochloric acid were added. The acid formed was extracted using ethyl acetate (2×). The combined organic phases were washed twice with water, dried over MsGO₄ and evaporated. The crystalline residue was triturated with ml of diisopropyl ether, filtered off with suction and dried in vacuo. 13.85 g (0.025 mol, 88.0%) of "Example 60b" of melting point 144°–146° C. were obtained.

$C_{33}H_{50}O_6$ (542), MS (FAB, 3-NBA/TFA): 565 (M+Na⁺)

Example 60c

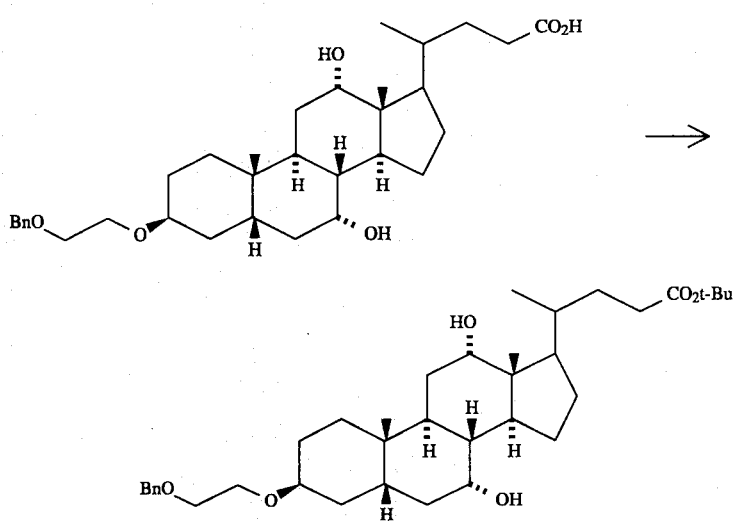

a) Anhydride formation 13.8 g (0.0254 mol) of "Example 60b" were dissolved in 250 ml of abs. tetrahydrofuran and 7.69 g (0.0762 mol) of triethylamine. 6.28 g (0.03 mol) of 2,6-dichlorobenzoyl chloride were added dropwise at room temperature and the mixture was then stirred under reflux for 3 h.

b) Ester formation

The anhydride solution obtained under a) was cooled to +10° C. and 28.12 g (0.38 mol) of tert.butanol and 3.1 g (0.0254 mol) of 4-dimethylaminopyridine were added successively, and the mixture was then heated to boiling in the course of 1 h and stirred under reflux for 4 h. The reaction mixture was then largely freed from tetrahydrofuran in vacuo. The residue was taken up in ethyl acetate, and the solution was thoroughly washed 3 times with water, dried using MgSO₄ and evaporated. Chromatography of the residue on silica gel using ethyl acetate/cyclohexane=1:1 gave 6.85 g of "Example 60c". (0.0114 mol, 45.0%) melting point: 79°–80° C.;

Example 60d

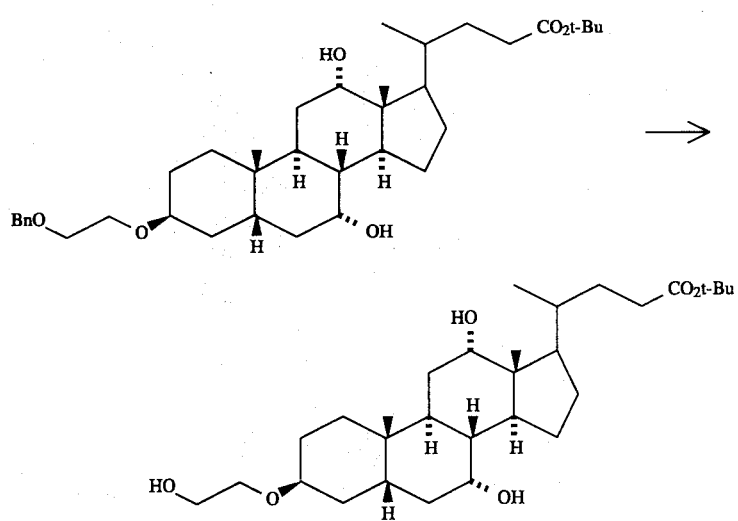

7.14 g (0.0119 mol) of "Example 60c" in 250 ml of ethyl acetate were hydrogenated over 1.5 g of Pd/C catalyst (10%) at room temperature and normal pressure. After completion of hydrogen absorption, the catalyst was filtered off and the filtrate was evaporated. 6.0 g of "Example 60d" were obtained (0.0117 mol, 98.9%)

$C_{30}H_{52}O_6$ (508), MS (FAB, 3-NBA/LiCl): 515 (M+Li)

Example 60e

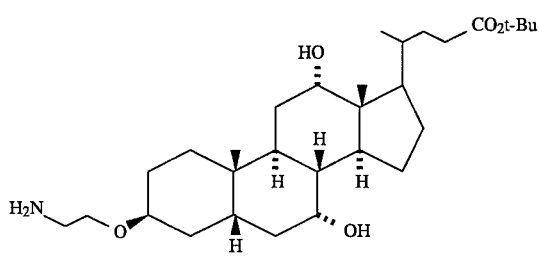

"Example 60e" was prepared from "Example 60d" in analogy to Examples 19–28.

$C_{30}H_{53}N\ O_5$ (507); MS (FAB, 3-NBA/LiCl): 514 (M+Li$^+$)

Example 61

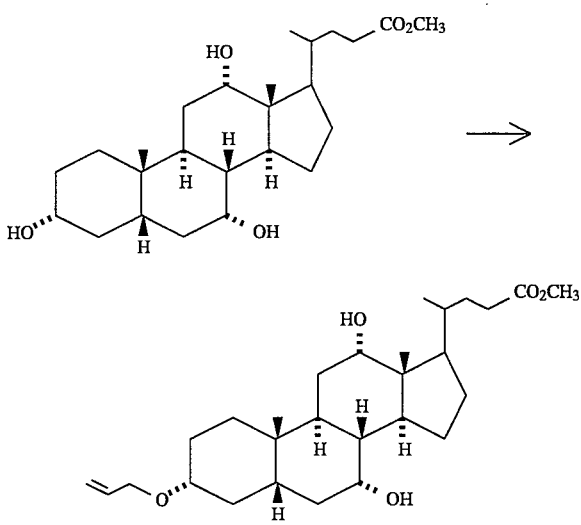

42.2 g (0.1 mol) of methyl cholate, 300 ml (1.8 mol) of N-ethyldiisopropylamine and 10 ml (0.12 mol) of allyl bromide were heated under reflux for 8 h. After each hour's reaction time, 5 ml of allyl bromide were added again in each case (TLC checking, cyclohexane/ethyl acetate=1:1). The reaction mixture was poured into 400 ml of conc. $H_2SO_4$/2000 ml of water and extracted using ethyl acetate (3×). The combined organic phases were washed once in each case with 1N HCl, water and saturated $NaHCO_3$ solution. Drying ($MgSO_4$), removal of the solvent and chromatography of the residue on silica gel (n-heptane/ethyl acetate=4:1→3:1→2:1) gave 2 1.91 g (0.047 mol, 47%) of "Example 61".

$C_{28}H_{46}O_5$ (462), MS (FAB, 3-NBA/LiCl): 469 (M+Li$^+$)

Example 62

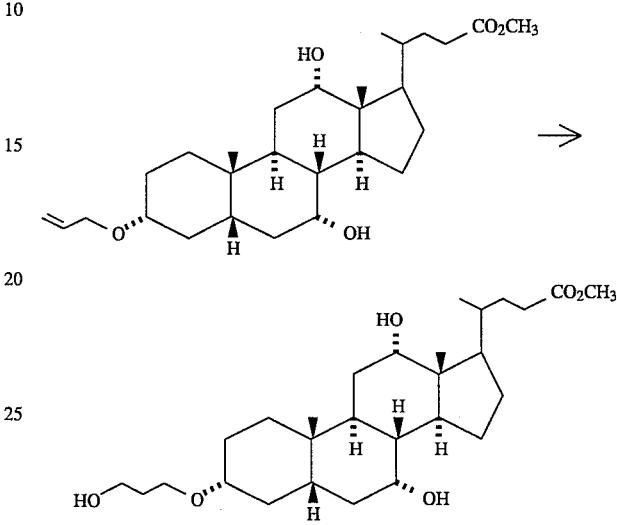

(1) Preparation of thexylborane: 85 ml of 1 molar 2,3-dimethylbutene solution (THF) were added dropwise at 0° C. under an argon atmosphere to 85 ml of 1 molar $BH_3$.THF solution (THF). The mixture was stirred at 0° C.

(2) Hydroboration: 8.6 g (18.59 mmol) of olefin "Example 61" in 25 ml of THF were added dropwise at 0° C. to the solution prepared according to (1). After 3 h at 0° C., the mixture was allowed to come to room temperature (TLC checking). After 16 h at room temperature, freshly prepared thexylborane solution (THF) was added dropwise. The mixture was again stirred at room temperature. When starting material was no longer detectable, the reaction mixture was carefully transferred into aqueous sodium hydroxide solution with intensive stirring under an argon atmosphere (1 equivalent of NaOH per equivalent of borane). 30 percent hydrogen peroxide solution was then added dropwise with ice-cooling. (2 equivalents per 1 equivalent of borane). After 20 min at 0° C., the mixture was warmed to 50° C. for 30 min. Saturated sodium chloride solution was added for better phase separation. The aqueous phase was extracted using ethyl acetate (2×) and the combined organic phases were washed with saturated sodium bisulfite solution (2×) and then with sodium chloride solution (1×). Drying with $MgSO_4$, removal of the solvent and chromatography on silica gel (ethyl acetate→ethyl acetate/ MeOH=20:1) gave 5.0 g (10.4 mmol, 56%) of "Example 62"

Rf (ethyl acetate): 0.18

$C_{28}H_{48}O_6$ (480); MS (FAB, 3-NBA/LiCl): 487 (M+Li$^+$).

In addition 1.0 g of the secondary alcohol was obtained.

Rf (ethyl acetate): 0.27.
Example 63
"Example 63" was obtained from "Example 62" in analogy to Examples 19–28.
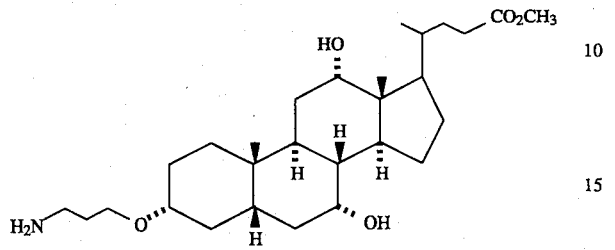
(X—G with the α-configuration on 3-C)
$C_{28}H_{49}NO_5$ (479); MS (FAB, 3-NBA/LiCl): 486 (M+Li$^+$)
Example 64
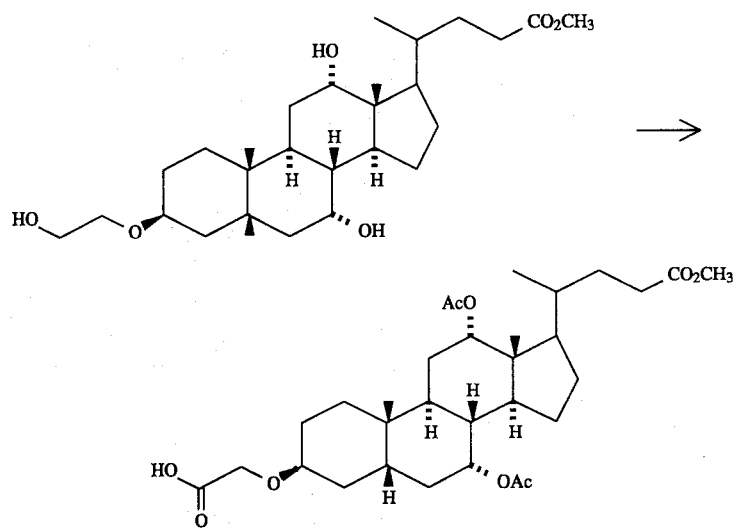
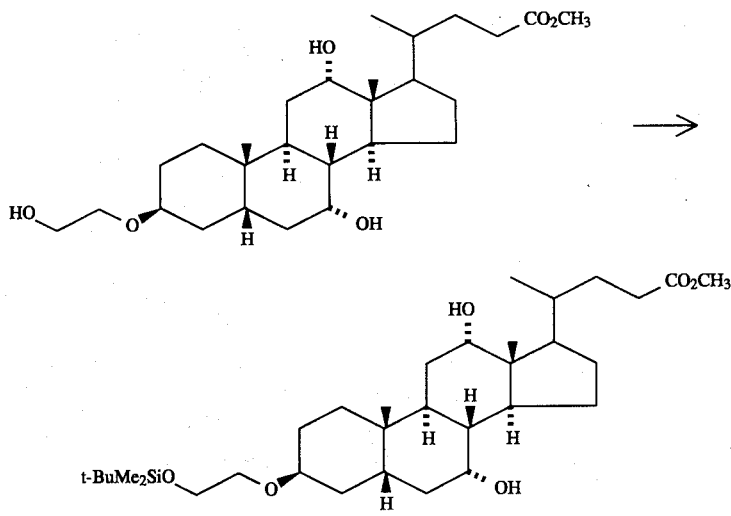
75 g (0.161 mol) of "Example 11" were stirred at room temperature for 4 h with 21.6 g (0.177 mol) of 4-dimethylaminopyridine and 26.7 g (0.177 mol) of tert.butyldimethylsilyl chloride in 500 ml of dry dichloromethane. The reaction mixture was poured into water and extracted using ethyl acetate (3×). The combined organic phases were dried (MgSO$_4$) and evaporated. Yield 93.6 g (quantitative) of silyl ether. A further purification was not necessary for preparative purposes.

$C_{33}H_{60}O_6Si$ (580); MS (FAB, 3-NBA/LiCl): 587 M+Li$^+$).
Step b)

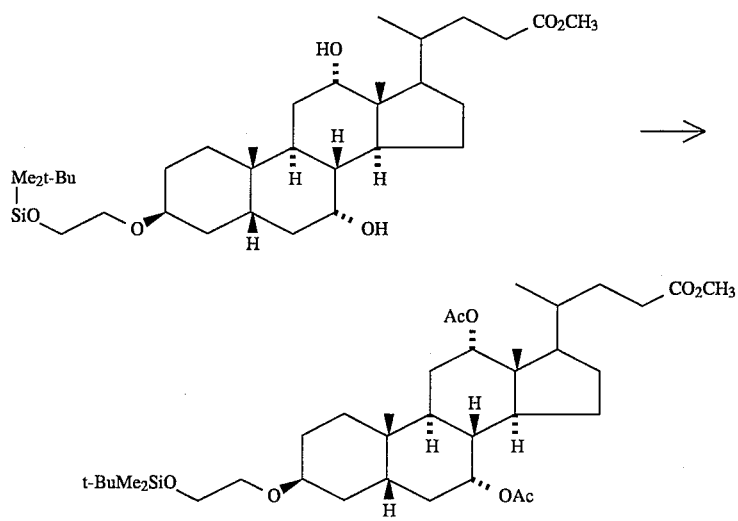

4.1 ml (0.043 mol) of acetic anhydride were added dropwise at 0° C. to 10 g (0.0172 mol) of the silyl ether obtained according to step a) and 5.3 g (0.043 mol) of 4-dimethylaminopyridine in 100 ml of dry pyridine. The mixture was stirred at room temperature for 4 h. The reaction mixture was poured into water and extracted using ethyl acetate (3×). The combined organic phases were washed with saturated aqueous NaHCO$_3$ solution and dried (MgSO$_4$). Evaporation of the solvent and chromatography on silica gel (ethyl acetate/cyclohexane=1:3) gave 10 g (0.015 mol, 87.7%) of diacetate.

$C_{37}H_{64}O_8Si$ (664); MS (FAB, 3-NBA/LiCl): 671 (M+Li$^+$).

Step c)

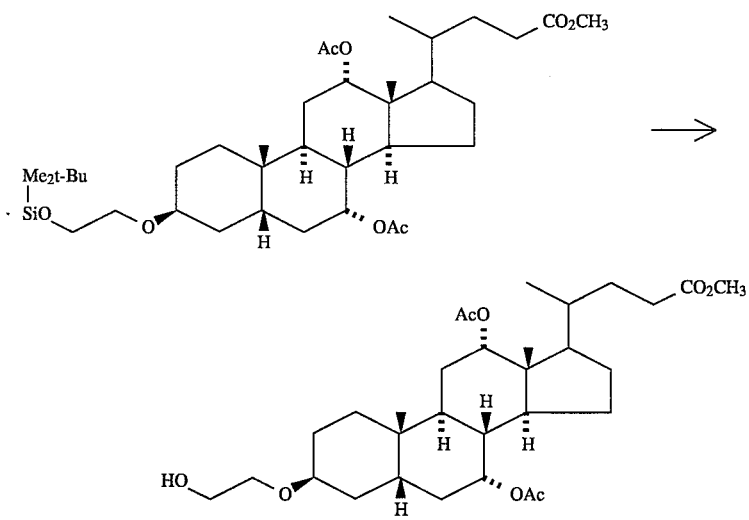

10 g (0.015 mol) of the diacetate obtained according to step b) were stirred at room temperature for 1 h with 5.2 g (0.0165 mol) of tetrabutylammonium fluoride trihydrate in 100 ml of tetrahydrofuran. The reaction mixture was poured into water and extracted using ethyl acetate (3×). The combined organic phases were dried (MgSO$_4$) and evaporated. Yield of alcohol quantitative. A further purification was not necessary for preparative purposes.

$C_{31}H_{50}O_8$ (550); MS (FAB, 3-NBA/LiCl): 557 (M+Li$^+$).
Step d)

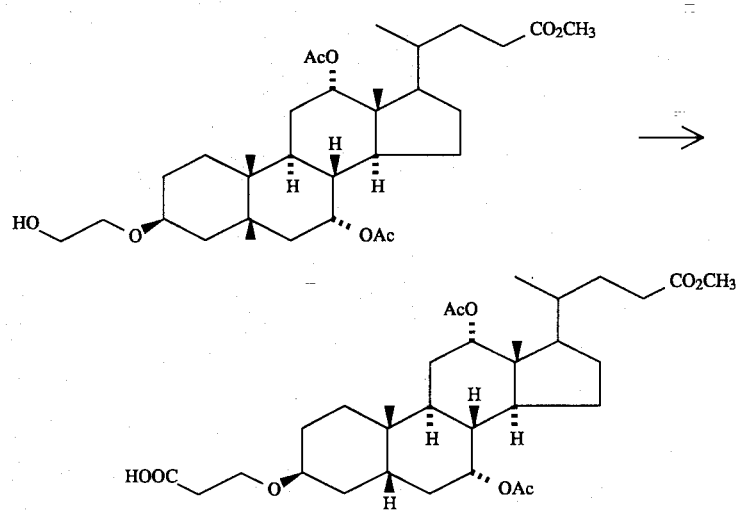

7.35 g (0.0133 mol) of the alcohol obtained according to step c) were stirred at room temperature for 24 h with 50 g (0.0133 mol) of pyridinium dichromate in 150 ml of dry dimethylformamide. The reaction mixture was poured into water and extracted using diethyl ether (3×). The combined organic phases were dried (MgSO$_4$) and evaporated. Chromatography on silica gel (ethyl acetate/cyclohexane=9:1) gave 5.1 g (0.009 mol, 58%) of "Example 64".

$C_{31}H_{48}O_9$ (564); MS (FAB, 3-NBA/LiCl): 571 (M+Li$^+$).

3. W—X—G, X=an intermediate member

Example 65 dropwise at 0° C. to 1.96 g (6.44 mmol) of chlorambucil (Sigma) in 100 ml of THF/20 ml of triethylamine and the mixture was stirred for 15 min. 3.0 g (6.44 mmol) of "Example 21", dissolved in THF, were added dropwise at 0° C. and the mixture was then stirred at room temperature for 30 min. The reaction mixture was poured into water and extracted three times using ethyl acetate. The combined organic phases were dried (MgSO$_4$) and evaporated. Chromatography on silica gel (ethyl acetate/methanol=9:1) gave 3.9 g (5.2 mmol, 81%) of "Example 65".

M.p.: 45°–50° C.

$C_{41}H_{64}Cl_2N_2O_8$ (750), MS (FAB, 3-NBA/LiI): 751

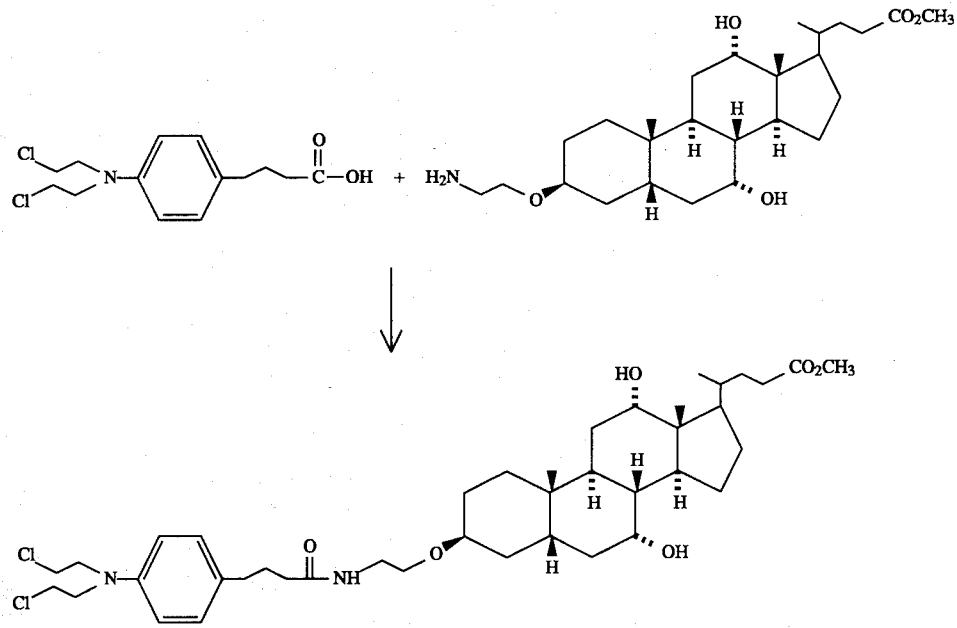

0.62 ml (6.44 mmol) of ethyl chloroformate were added (M+Li$^+$) Example 66

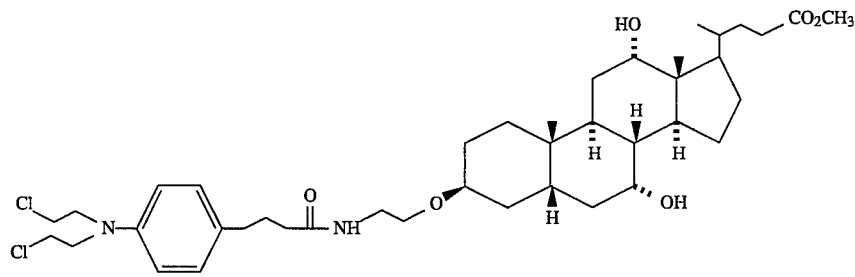

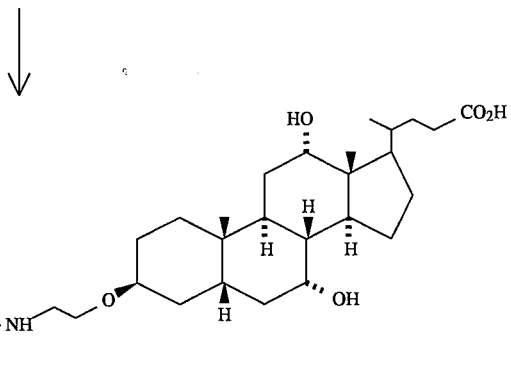

5 ml of 1N aqueous sodium hydroxide solution were added dropwise to a solution of 1.96 g (2.6 mmol) of "Example 65" in 20 ml of ethanol. After 3 h at room temperature, a further 5 ml of 1N aqueous sodium hydroxide solution were added and the mixture was stirred again for 3 h. The reaction mixture was poured into 200 ml of water, neutralized using 1N aqueous hydrochloric acid and extracted three times using ethyl acetate. The combined organic phases were dried (MgSO$_4$) and evaporated.

Yield: 1.91 g (2.6 mmol, quant.) of "Example 66"

M.p.: 60°–70° C.

$C_{40}H_{62}Cl_2N_2O_6$ (736), MS (FAB, 3-NBA/LiI): 743 (M+Li$^+$)

Example 67

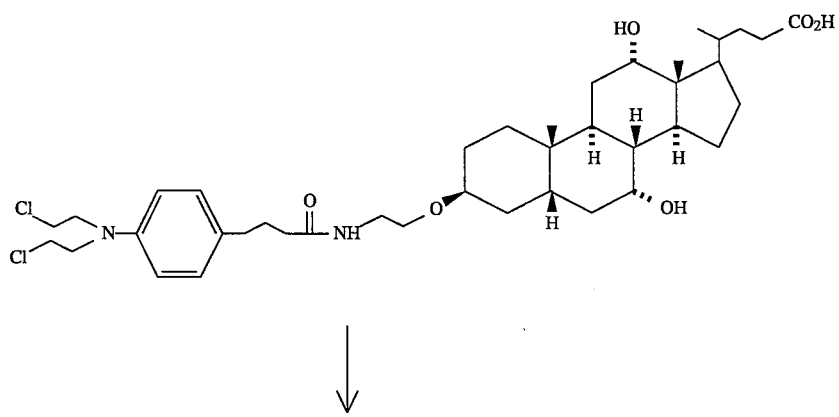

-continued

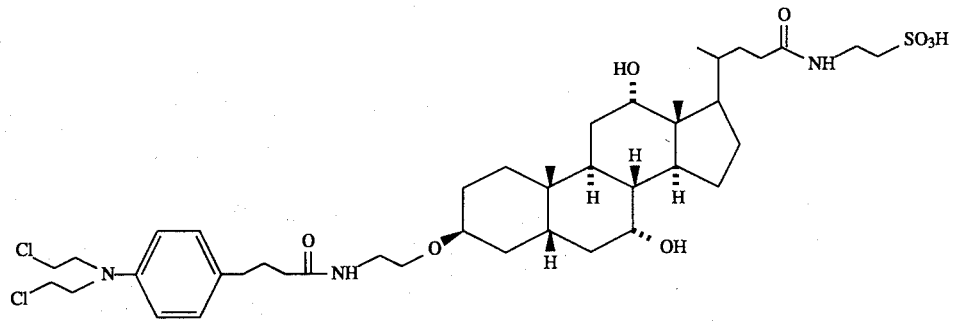

0.2 ml (2.03 mmol) of ethyl chloroformate were added dropwise at 0° C. to a solution of 1.5 g (2.03 mmol) of "Example 66" and 0.97 ml (4.06 mmol) of tri-n-butylamine in 10 ml of dioxane and the mixture was stirred at 0° C. for 15 min. A solution of 0.508 g (4.06 mmol) of taurine in 4 ml of 1N aqueous sodium hydroxide solution was then added dropwise at 0° C. The mixture was stirred at room temperature for 1 h, poured into 200 ml of water and neutralized using 1N aqueous hydrochloric acid. It was extracted using ethyl acetate with the addition of a little methanol (3×) and the combined organic phases were dried (MgSO$_4$). Removal of the solvent and flash chromatography on silica gel (ethyl acetate/methanol=4:1, then 2:1) gave 1.59 g (1.89 mmol, 93%) of "Example 67".

M.p.: 130°–140° C.

$C_{42}H_{67}Cl_2N_3O_8S$ (843), MS (FAB, 3-NBA/LiI): 856 (M+Li$^+$—H)

dropwise at 0° C. to a solution of 1.5 g (2.03 mmol) of "Example 66" and 0.97 ml (4.06 mmol) of tri-n-butylamine in 10 ml of dioxane and the mixture was stirred at 0° C. for 15 min. A solution of 0.305 g (4.06 mmol) of glycine in 4.0 ml of 1N aqueous sodium hydroxide solution was then added and the mixture was stirred at room temperature for 4 h. The reaction mixture was then poured into 200 ml of water, neutralized using 1N aqueous hydrochloric acid and extracted using ethyl acetate. The combined organic phases were dried (MgSO$_4$), evaporated and flash chromatographed on silica gel (ethyl acetate/methanol= 2:1).

Yield 1.15 g (1.45 mmol, 71%) of "Example 68".

M.p.: 75°–85° C.

$C_{42}H_{65}Cl_2N_3O_7$ (793), MS (F/LB, 3-NBA/LiI): 806 (M+2 Li$^+$—H)

Example 68

Examples 69–78

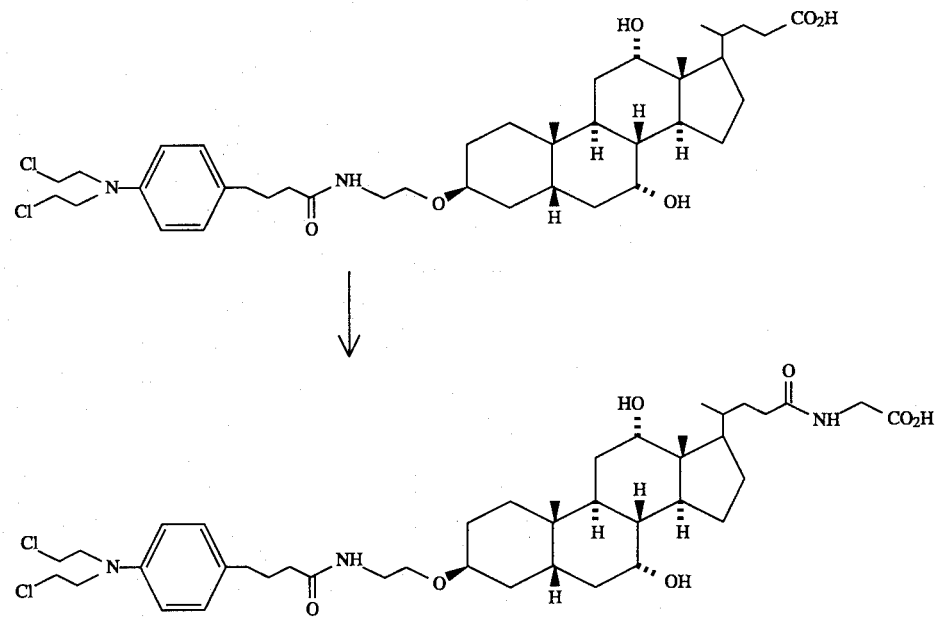

0.2 ml (2.03 mmol) of ethyl chloroformate were added

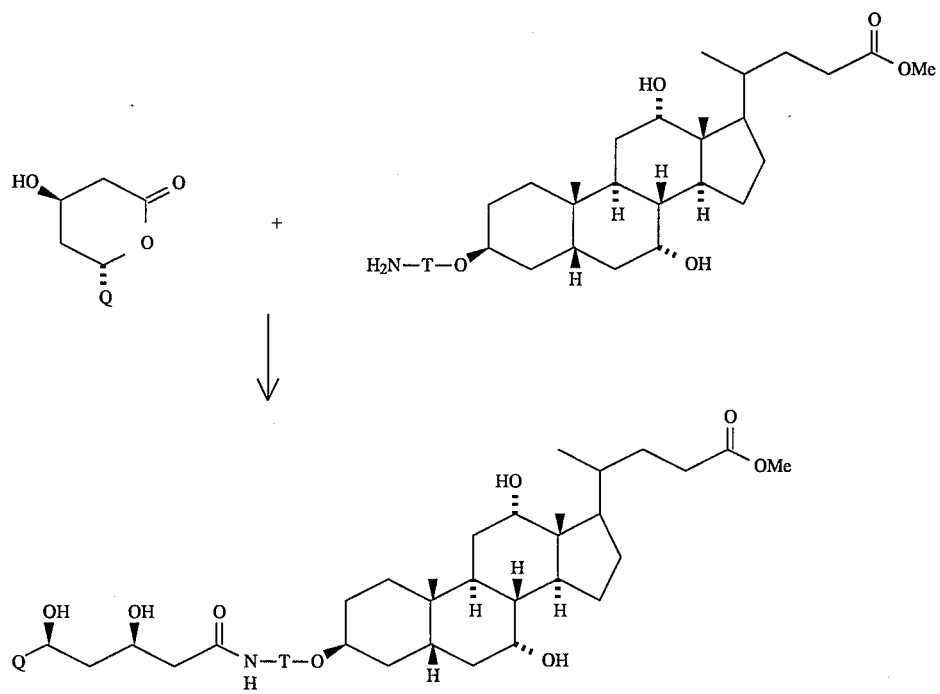

Example 69

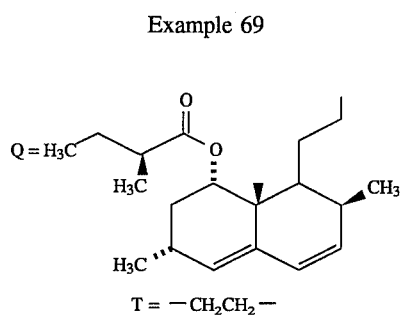

T = —CH₂CH₂—

A mixture of 750 mg (1.61 mmol) of "Example 21", 5 ml of triethylamine, 200 mg (1.61 mmol) of dimethylaminopyridine (DMAP) and 651 mg (1.61 mmol) of mevinolin in 25 ml of dry THF was heated under reflux for 48 h. The solvent was removed and the residue was chromatographed on silica gel (ethyl acetate/MeOH=19:1).

Yield: 900 mg (1.03 mmol), 64%) of "Example 69"

M.p.: 78°–80° C.

$C_{51}H_{83}NO_{10}$ (869), MS (FAB, 3-NBA/LiI): 876 (M+Li⁺)

Example 70

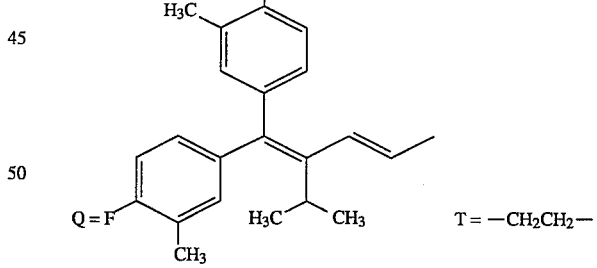

"Example 70" was obtained analogously to Example 69 using "Example 21".

M.p.: 70°–75° C.

$C_{53}H_{75}F_2NO_8$ (891), MS (FAB, 3-NBA/LiI): 898 (M+Li⁺)

(For the preparation of the lactone component, see DE 3,722,807-A); see also Tetrahedron Letters 29, 929–930 [1988], where compounds without the methyl groups adjacent to the F are described).

Example 71

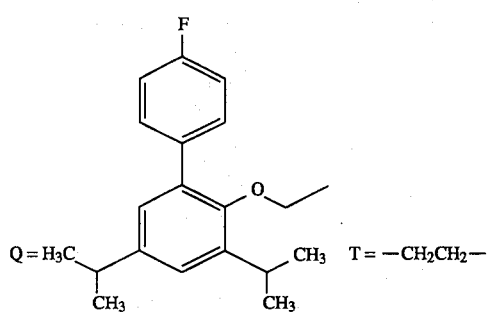

"Example 71" was obtained analogously to 69 using "Example 21".
M.p.: 65°–70° C.
$C_{51}H_{76}FNO_9$ (865), MS (FAB, 3-NBA/LiI): 872 (M+Li$^+$)
(For preparation of the lactone component see DE 3,819,999-A, Example 1; see also the description before the pharmacological part of the present application).

Example 72

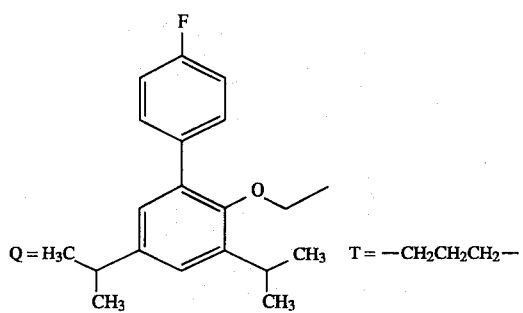

"Example 72" was obtained analogously to 69 using "Example 22".
$C_{52}H_{78}FNO_8$ (879), MS (FAB, 3-NBA/LiCl): 886 (M+Li$^+$).

Example 73

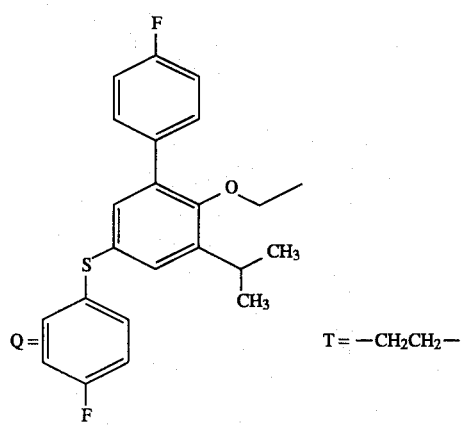

"Example 73" was obtained analogously to 69 using Example 21.
$C_{54}H_{73}F_2NO_9S$ (949), MS (FAB, 3-NBA/LiCl)=956 (M+Li$^+$).
(For the preparation of the lactone component see DE P 3,929,913).

Example 74

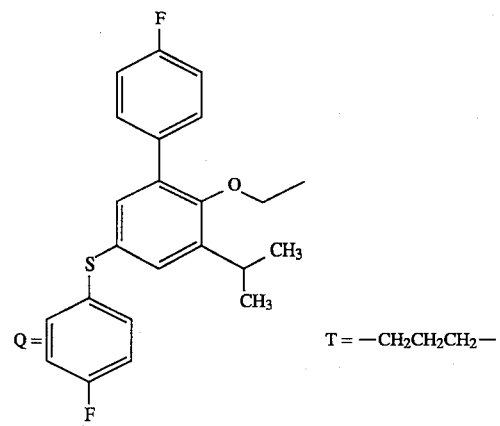

"Example 74" was obtained analogously to 69 using "Example 22".
$C_{55}H_{75}F_2NO_9S$ (963), MS (FAB, 3-NBA/LiCl): 970 (M+Li$^+$).

Example 75

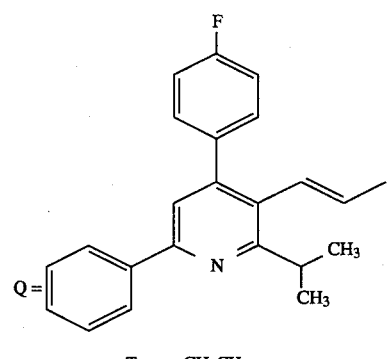

"Example 75" was obtained analogously to 69 using "Example 21".
M.p.: 74°–76° C.
$C_{54}H_{73}FN_2O_8$ (896), MS (FAB, 3-NBA/LiI): 903 (M+Li$^+$)

71
Example 76
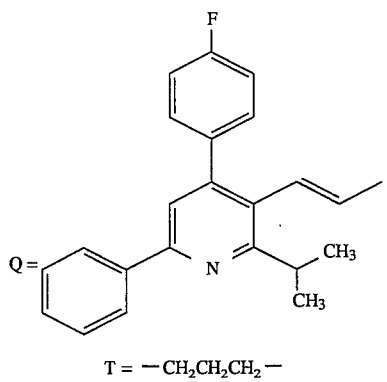
"Example 7 6" was obtained analogously to 69 using Example 22".
$C_{55}H_{75}FN_2O_8$ (910), MS (FAB, 3-NBA/LiCl): 917 (M+Li$^+$).
Example 77
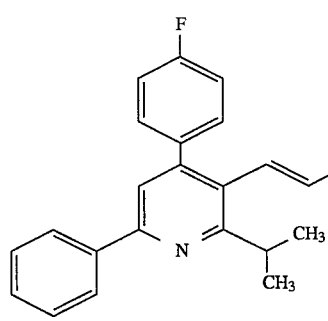
"Example 77" was obtained analogously to 69 using "Example 63".
$C_{55}H_{75}FN_2O_8$ (910), MS (FAB, 3-NBA/LiCl): 917 (M+Li$^+$).
72
Example 78
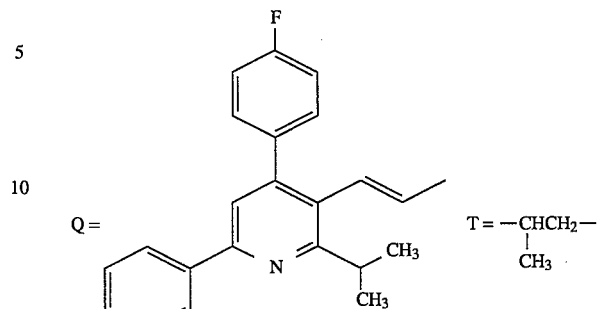
"Example 78" was obtained analogously to 69 using "Example 28".
$C_{55}H_{75}FN_2O_8$ (910), MS (FAB, 3-NBA/LiCl): 917 (M+Li$^+$).
Examples 79–88
Variant A
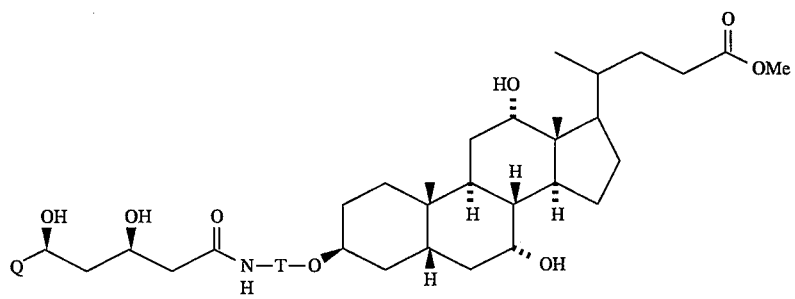

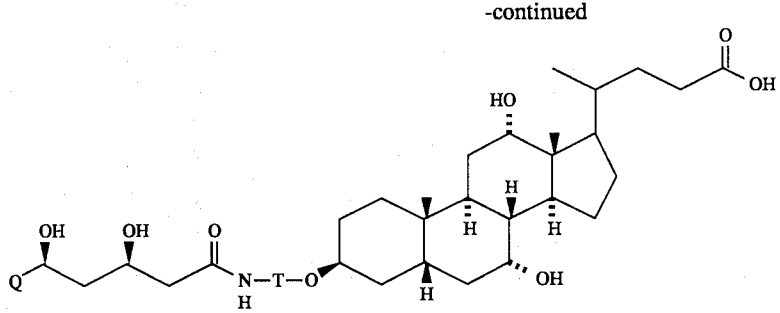

Example 79

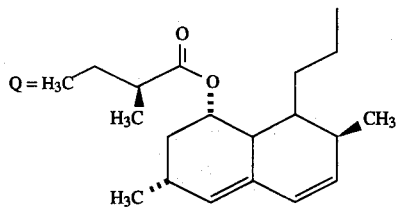

T = —CH₂CH₂—

250 mg (0.29 mmol) of "Example 69" were dissolved in 5 ml of ethanol and 2.0 ml of 1N aqueous sodium hydroxide solution were added. After stirring at room temperature for 6 h, the mixture was neutralized using 1N hydrochloric acid and extracted using ethyl acetate (3×). The combined organic phases were dried with MgSO₄ and evaporated.

Yield 230 mg (0.27 mmol, 94%) of "Example 79".

M.p. 70=20 –80° C.

$C_{50}H_{81}NO_{10}$ (855), MS (FAB, 3-NBA/LiI): 862 (M+Li⁺)

Variant B

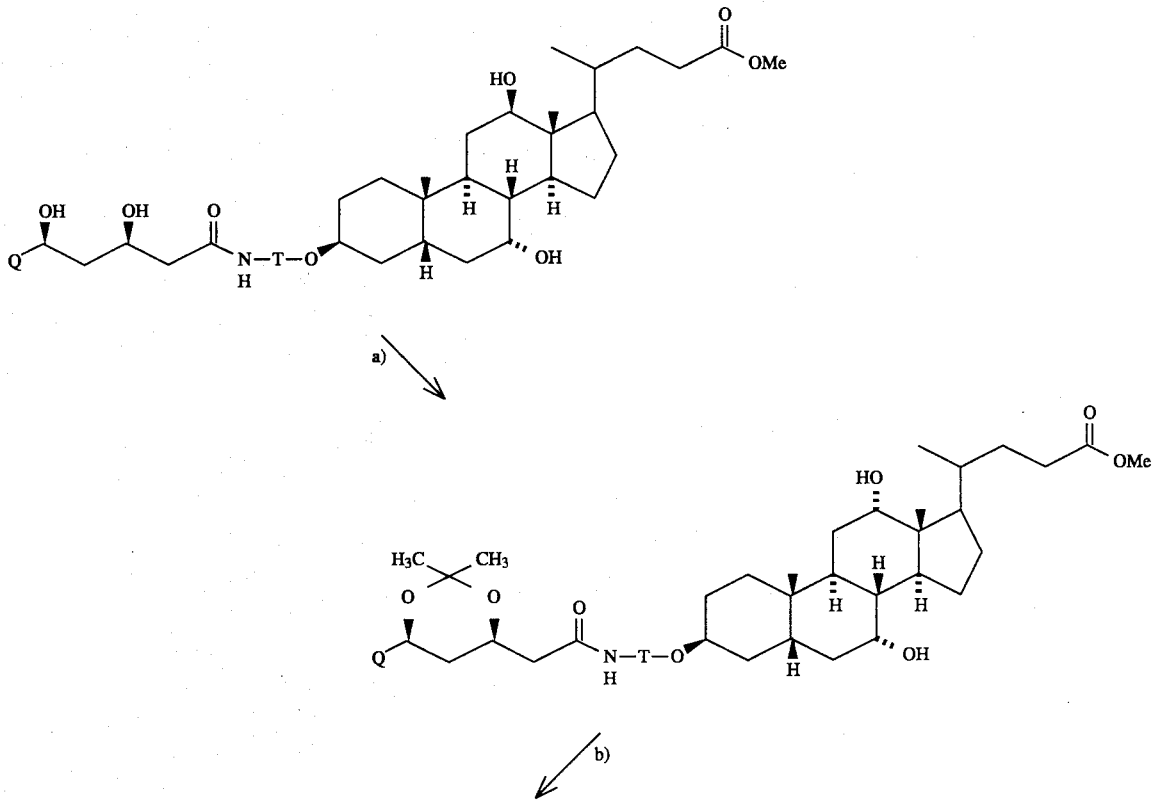

-continued

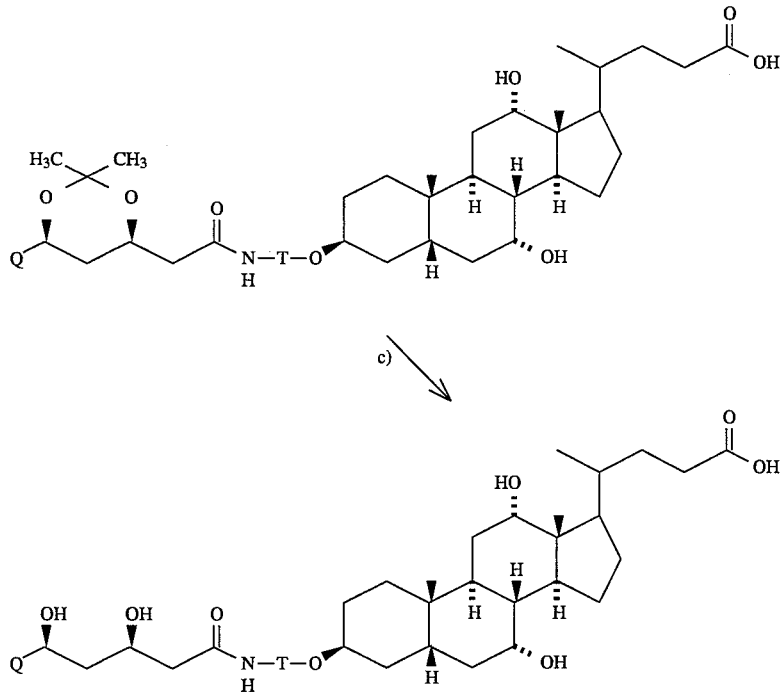

Example 80

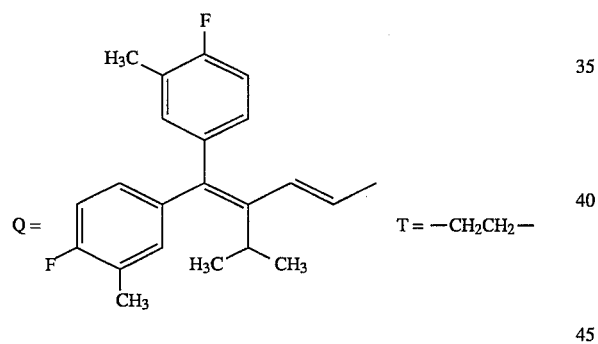

a) 400 mg (0.45 mmol) of "Example 70" and a crystal of p-toluenesulfonic acid were dissolved in 20 ml of acetone/ dimethoxypropane 1:1 and the solution was stirred at room temperature. After 15 min, the solvent was evaporated and the residue was chromatographed on silica gel (chloroform/ methanol 19:1).

Yield 390 mg (0.42 mol, 93%) of acetonide.

$C_{56}H_{79}F_2NO_8$ (931), MS (FAB, 3-NBA/LiCl)=938 (M+Li$^+$).

b) 390 mg (0.42 mmol) of acetonide were dissolved in 20 ml of ethanol and 5 ml of 1N aqueous sodium hydroxide solution were added. After stirring at room temperature for 5 h, the mixture was neutralized using 2N hydrochloric acid and extracted using ethyl acetate (3×). The combined organic phases were dried with MgSO$_4$ and evaporated. The crude product was reacted without further purification.

c) The crude product from b) was dissolved in 20 ml of THF and 5 ml of 2N hydrochloric acid were added. After stirring for 2 h, 100 ml of water were added and the mixture was extracted using ethyl acetate (3×). The combined organic phases were dried using MgSO$_4$ and evaporated. Flash chromatography on silica gel (dichloromethane/ methanol 9:1) gave 250 mg (0.29 mmol, 68%) of "Example 80c".

$C_{52}H_{73}F_2NO_8$ (877), MS (FAB, 3-NBA/LiCl): 884 (M+Li$^+$).

Examples 81–88

"Examples 81–88" were obtained from 71–78 analogously to or 80.

TABLE 6
| Ex. | Q | T | Starting material | MS(FAB, 3-NBA/ LiI or LiCl) |
|---|---|---|---|---|
| 81 | 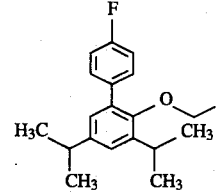 | —CH$_2$CH$_2$— | 71 | C$_{50}$H$_{74}$FNO$_9$ (851) 858 (M + Li$^+$) |
| 82 | 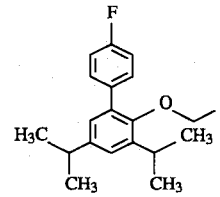 | —CH$_2$CH$_2$CH$_2$— | 72 | C$_{51}$H$_{76}$FNO$_9$ (865) 872 (M + Li$^+$) |
| 83 | 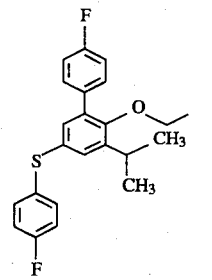 | —CH$_2$CH$_2$— | 73 | C$_{53}$H$_{71}$F$_2$NO$_9$S (935) 936 (M + H$^+$) |
| 84 | 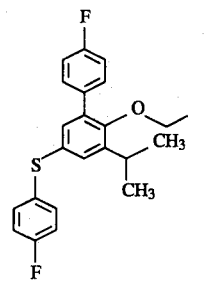 | —CH$_2$CH$_2$CH$_2$— | 74 | C$_{54}$H$_{73}$F$_2$NO$_9$S (949) 956 (M + Li$^+$) |
| 85 | 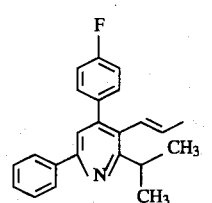 | —CH$_2$CH$_2$— | 75 | C$_{53}$H$_{71}$FN$_2$O$_3$ (882) 889 (M + Li$^+$) |
| 86 | 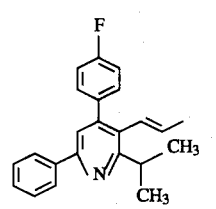 | —CH$_2$CH$_2$CH$_2$— | 76 | C$_{54}$H$_{73}$FN$_2$O$_8$ (896) 903 (M + Li$^+$) |

TABLE 6-continued

| Ex. | Q | T | Starting material | MS(FAB, 3-NBA/ LiI or LiCl) |
|---|---|---|---|---|
| 87 | | | | $C_{54}H_{73}FN_2O_8$ (896) 903 (M + Li$^+$) |
| 88 | | —CH—CH$_2$— <br> \|<br> CH$_3$ | 78 | $C_{54}H_{73}FN_2O_8$ (896) 903 (M + Li$^+$) |

Examples 89–98

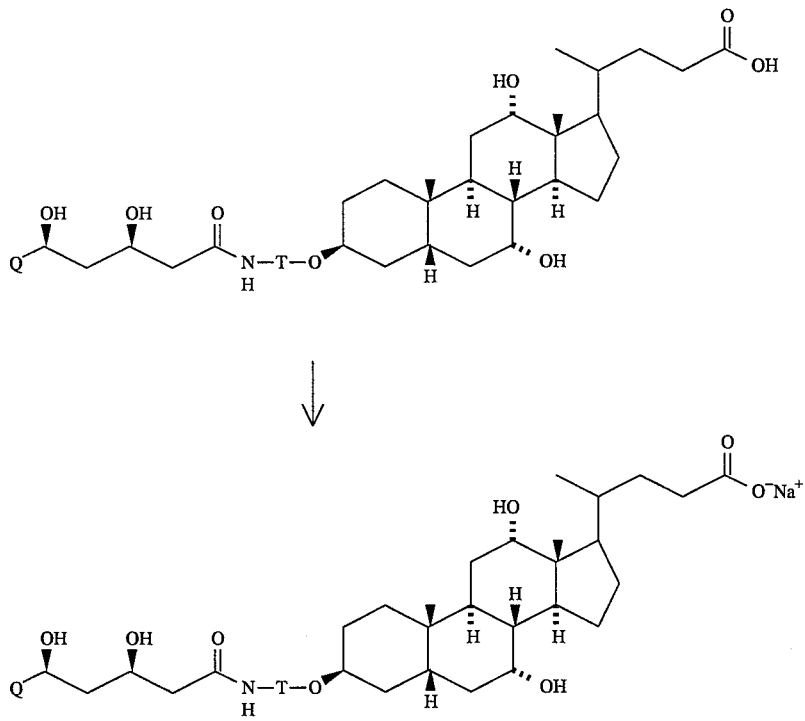

Example 89

$T = -CH_2CH_2-$

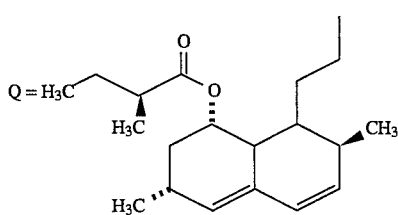

150 mg (0.175 mmol) of "Example 79" were dissolved in 10 ml of ethanol and 1.75 ml of 0.1N aqueous sodium hydroxide solution were added. After stirring at room temperature for 10 min, the solvent is evaporated. Yield 150 mg (quant.) of sodium salt "Example 89".

Examples 90–98

"Examples 90–98" were obtained analogously to 89.

TABLE 7

| Ex. | Q | T | Starting material |
|---|---|---|---|
| 90 | (structure: 4-fluoro-3-methylphenyl and 4-fluoro-3-methylphenyl groups on C=C with isopropyl and propenyl substituents) | —CH₂CH₂— | 80 |
| 91 | (structure: 4'-fluorobiphenyl with 2-ethoxy, 3,5-diisopropyl substituents) | —CH₂CH₂— | 81 |
| 92 | (structure: 4'-fluorobiphenyl with 2-ethoxy, 3,5-diisopropyl substituents) | —CH₂CH₂CH₂— | 82 |
| 93 | (structure: 4'-fluorobiphenyl with 2-ethoxy, 3-isopropyl, 5-(4-fluorophenylthio) substituents) | —CH₂CH₂— | 83 |
| 94 | (structure: 2',4'-difluorobiphenyl with 2-ethoxy, 3-isopropyl, 5-(phenylthio) substituents) | —CH₂CH₂CH₂— | 84 |
| 95 | (structure: pyridine with 4-fluorophenyl, phenyl, isopropyl and propenyl substituents) | —CH₂CH₂— | 85 |
| 96 | (structure: pyridine with 4-fluorophenyl, phenyl, isopropyl and propenyl substituents) | —CH₂CH₂CH₂— | 86 |

TABLE 7-continued

| Ex. | Q | T | Starting material |
|---|---|---|---|
| 97 | (structure with fluorophenyl pyridine and steroid with O⁻Na⁺) | | 87 |
| 98 | (structure with fluorophenyl pyridine and propenyl) | —CHCH₂— <br> \|<br>CH₃ | 88 |

Examples 99–108

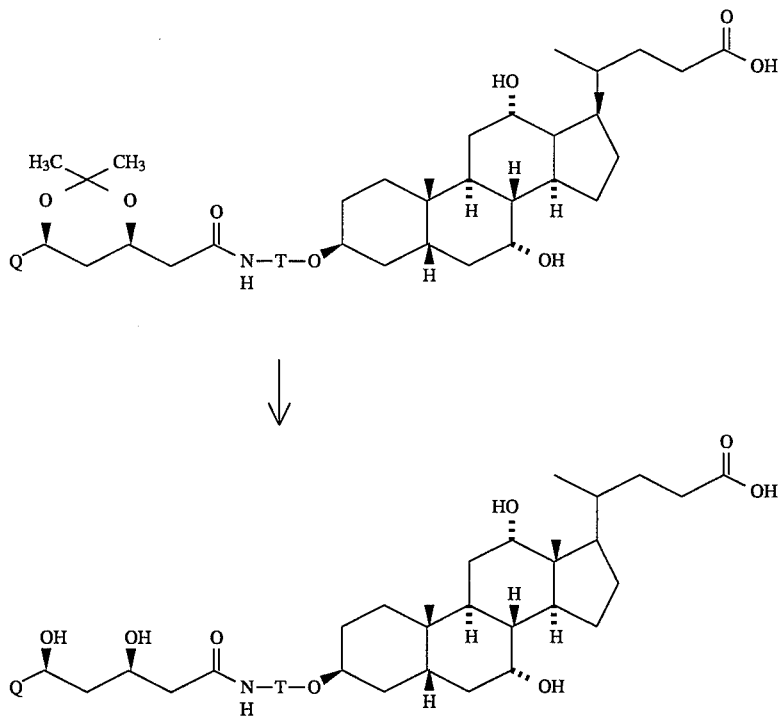

Example 99

T = —CH₂CH₂—

-continued 400 mg (0.45 mmol) of acetonide from 69 (see Examples 79–88, variant B) were dissolved in 40 ml of absolute THF, 0.12 ml (0.90 mmol) of triethylamine was added and the mixture was cooled to 0° C. 0.07 ml (0.68 mmol) of ethyl chloroformate was added and the mixture was stirred for 15 min. A solution of 100 mg (1.3 mmol) of glycine in 12 ml of 0.1N aqueous sodium hydroxide solution was then added dropwise. The mixture was warmed to room temperature and stirred for 1 more hour. The mixture was poured into water, acidified using 2N hydrochloric acid and extracted using ethyl acetate (3×). The combined organic phases were dried using $MgSO_4$ and evaporated. The residue was dissolved in 50 ml of THF, 10 ml of 1N hydrochloric acid were added and the mixture was stirred at room temperature for 4 h. It was poured into water, extracted using ethyl acetate (3×), and the combined organic phases were dried using $MgSO_4$ and evaporated.

Flash chromatography on silica gel (chloroform/methanol 7:3) gave 230 mg (0.25 mmol, 56%) of "Example 99" $C_{52}H_{84}N_2O_{11}$ (912), MS (FAB, 3-NBA/LiCl): 919 (M+Li$^+$).

Examples 100–108

"Examples 100–108" were obtained analogously to 99.

TABLE 8

| Ex. | Q | T | Starting Material: acetonide from (see Examples 79–88, variant B) | MS (FAB, 3-NBA/ LiCl or LiI) |
|---|---|---|---|---|
| 100 | (structure) | $-CH_2CH_2-$ | 70 | $C_{54}H_{76}F_2N_2O_9$ (934) 941 (M + Li$^+$) |
| 101 | (structure) | $-CH_2CH_2-$ | 71 | $C_{52}H_{77}FN_2O_{10}$ (908) 935 (M + Na$^+$) |
| 102 | (structure) | $-CH_2CH_2CH_2-$ | 72 | $C_{53}H_{79}FN_2O_{10}$ (922) 929 (M + Li$^+$) |
| 103 | (structure) | $-CH_2CH_2-$ | 73 | $C_{55}H_{74}F_2N_2O_{10}S$ (992) 1015 (M + Na$^+$) |
| 104 | (structure) | $-CH_2CH_2CH_2-$ | 74 | $C_{56}H_{76}F_2N_2O_{10}S$ (1006) 1029 (M + Na$^+$) |

TABLE 8-continued

| Ex. | Q | T | Starting Material: acetonide from (see Examples 79–88, variant B) | MS (FAB, 3-NBA/ LiCl or LiI) |
|---|---|---|---|---|
| 105 | ![Q structure: 4-(4-fluorophenyl)-3-propenyl-2-isopropyl-6-phenylpyridine] | —CH$_2$CH$_2$— | 75 | C$_{55}$H$_{74}$FN$_3$O$_9$ (939) 946 (M + Li$^+$) |
| 106 | ![same Q structure] | —CH$_2$CH$_2$CH$_2$— | 76 | C$_{56}$H$_{76}$FN$_3$O$_9$ (953) 960 (M + Li$^+$) |
| 107 | ![full structure shown] | | 77 | C$_{56}$H$_{76}$FN$_3$O$_9$ (953) 960 (M + Li$^+$) |
| 108 | ![same Q structure] | —CHCH$_2$— \| CH$_3$ | 78 | C$_{56}$H$_{76}$FN$_2$O$_9$ (953) 960 (M + Li$^+$) |

The corresponding Na salts were prepared from "Examples 100–108" analogously to Examples 89–98.

Examples 109–118

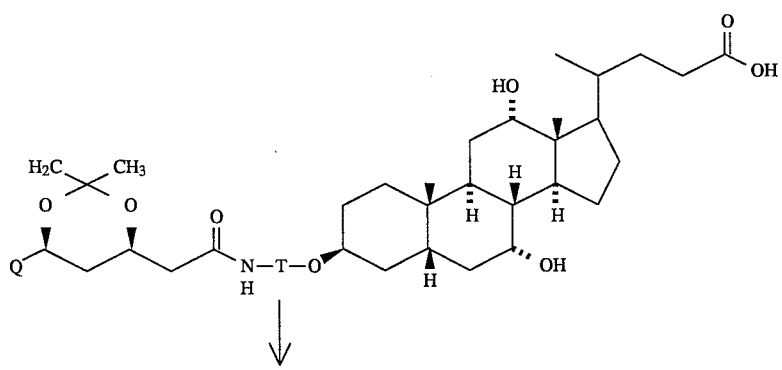

-continued

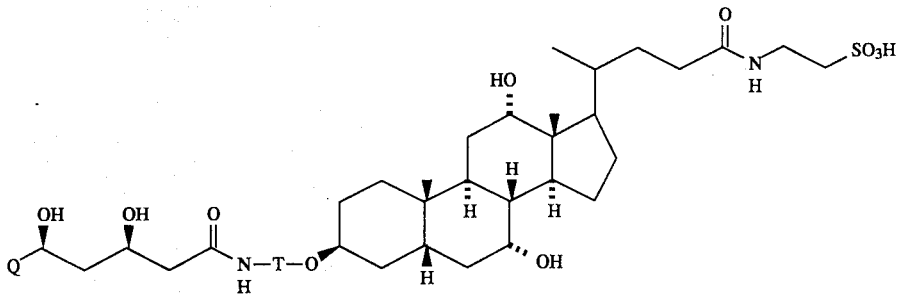

Example 109

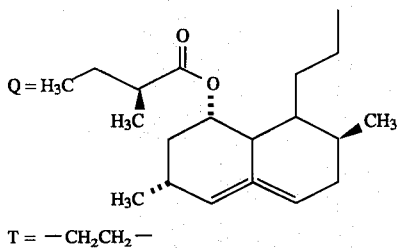

T = —CH₂CH₂—

400 mg (0.45 mmol) of acetonide from 69 (see Examples 79–88, variant B) were dissolved in 40 ml of absolute THF, 0.12 ml (0.90 mmol) of triethylamine was added and the mixture was cooled to 0° C. 0.07 ml (0.68 mmol) of ethyl chloroformate was added and the mixture was stirred for 15 min. A solution of 160 mg (1.3 mmol) of taurine in 12 ml of 0.1N aqueous sodium hydroxide solution was then added dropwise. The mixture was warmed to room temperature and stirred for 1 more hour. The mixture was poured into water, acidified using 2N hydrochloric acid and extracted using ethyl acetate (3×). The combined organic phases were dried using MgSO₄ and evaporated. The residue was dissolved in 50 ml of THF, 10 ml of 1N hydrochloric acid were added and the mixture was stirred at room temperature for 4 h. It was poured into water, extracted using ethyl acetate (3×), and the combined organic phases were dried using MgSO₄ and evaporated. Flash chromatography on silica gel (dichloromethane/methanol 7:3) gave 270 mg (0.28 mmol, 62%) of "Example 109".

$C_{52}H_{86}N_2O_{12}S$ (962 ), MS (FAB, 3-NBA/LiCl): 969 (M+Li⁺) .

Examples 110–118

"Examples 110–118" were obtained analogously to 109.

TABLE 9

| Ex. | Q | T | Starting Material: acetonide from (see Examples 79–88, variant B) | MS (FAB, 3-NBA/ LiCl or LiI) |
|---|---|---|---|---|
| 110 | ![structure with F, H₃C, F, H₃C, CH₃, CH₃] | —CH₂CH₂— | 70 | $C_{54}H_{78}F_2N_2O_{10}S$ (984) 991 (M + Li⁺) |
| 111 | ![structure with F, H₃C, O, CH₃, CH₃, CH₃] | —CH₂CH₂— | 71 | $C_{52}H_{79}FN_2O_{11}S$ (958) 981 (M + Na⁺) |

TABLE 9-continued

| Ex. | Q | T | Starting Material: acetonide from (see Examples 79–88, variant B) | MS (FAB, 3-NBA/ LiCl or LiI) |
|---|---|---|---|---|
| 112 | (4-fluorophenyl)-ethoxy-diisopropyl-phenyl | —CH₂CH₂CH₂— | 72 | $C_{53}H_{81}FN_2O_{11}S$ (972) 995 (M + Na⁺) |
| 113 | (4-fluorophenyl)-ethoxy-isopropyl-(4-fluorophenylthio)-phenyl | —CH₂CH₂— | 73 | $C_{55}H_{76}F_2N_2O_{11}S_2$ (1042) 1065 (M + Na⁺) |
| 114 | (4-fluorophenyl)-ethoxy-isopropyl-(4-fluorophenylthio)-phenyl | —CH₂CH₂CH₂— | 74 | $C_{56}H_{78}F_2N_2O_{11}S_2$ (1056) 1079 (M + Na⁺) |
| 115 | 4-(4-fluorophenyl)-3-propenyl-2-isopropyl-6-phenyl-pyridyl | —CH₂CH₂— | 75 | $C_{55}H_{76}FN_3O_{10}S$ (989) 996 (M + Li⁺) |
| 116 | 4-(4-fluorophenyl)-3-propenyl-2-isopropyl-6-phenyl-pyridyl | —CH₂CH₂CH₂— | 76 | $C_{56}H_{78}FN_3O_{10}S$ (1003) 1010 (M + Li⁺) |
| 117 | (full structure shown) | | 77 | $C_{55}H_{76}FN_3O_{10}S$ (1003) 1010 (M + Li⁺) |

TABLE 9-continued

| Ex. | Q | T | Starting Material: acetonide from (see Examples 79–88, variant B) | MS (FAB, 3-NBA/ LiCl or LiI) |
|---|---|---|---|---|
| 118 | 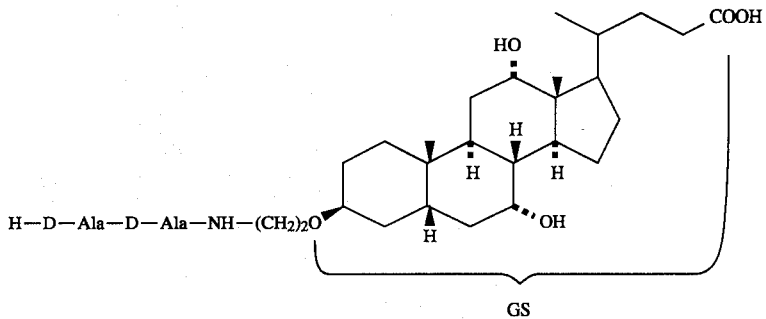 | —CHCH$_2$—<br>\|<br>CH$_3$ | 78 | C$_{56}$H$_{78}$FN$_3$O$_{10}$S<br>(1003)<br>1010 (M + Li$^+$) |

The corresponding Na salts were prepared from

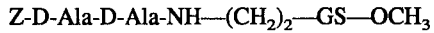

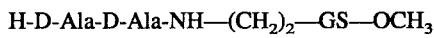

GS

"Examples 109–118" analogously to Examples 89–98.
W—X—G, W=model peptide (D-alanyl peptides).

Preparation of model peptides for coupling to bile acids
The N-terminally protected D-alanyl peptides (protective group, for example, benzyloxycarbonyl or Boc: tertbutyloxycarbonyl) or their active esters employed for coupling to Example 21 are prepared and characterized by methods which are generally customary in peptide chemistry (see, for example, Houben-Weyl, volumes 15/1 and 15/2).

The N-terminally protected oligo-D-alanyl peptides are linked to the amino function of the bile acid derivative either in the form of their active esters, for example as the N-hydroxysuccinimide (OSu) or 1-hydroxybenzotriazole (OBt) ester, or with the aid of condensing reagents (for example dicyclohexylcarbodiimide) with the addition of a racemization-inhibiting reagent, for example N-hydroxysuccinimide (HOSu) or 1-hydroxybenzotriazole (HOBt).

The peptide protective group and the methyl ester group of the bile acid derivative are subsequently removed, and owing to the orthogonal protective group strategy used here—the N-terminal protective group can be removed, for example, by hydrogenation (Z) or by acidolysis (Boc), while the methyl ester group of the bile acid derivative is hydrolyzed—the synthesis of partly protected bile acid-peptide conjugates is also possible.

The respective intermediates and the final product are in general purified by column chromatography and are characterized by thin-layer chromatography and by means of $^1$H-NMR spectroscopy.

Examples 119–121

H-D-Ala-D-Ala-NH—(CH$_2$)$_2$ 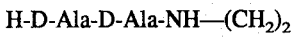

Example 119

Z-D-Ala-D-Ala-NH—(CH$_2$)$_2$—GS—OCH$_3$ 485 mg (1.04 mmol) of "Example 21" and 467 mg (1.14 mmol) of Z-D-Ala-D-Ala-OSu are dissolved in 10 ml of dichloromethane and the mixture is stirred at room temperature for 1.5 h. After removing the solvent in vacuo, 930 mg of solid residue are obtained which is chromatographed through a silica gel column (50×2 cm, Matrex silica gel 70–200 µm). Eluent: dichloromethane/methanol/acetic acid 85:10:5.

Fractions 3 and 4 contain the desired product; fraction 4 additionally still contains N-hydroxysuccinimide, which can be removed by triturating the residue with water or highly dilute hydrochloric acid after removing the solvent.

After combining both fractions, 450 mg (57%) of "Example 119" are obtained as a white solid.

R$_f$ (dichloromethane/methanol/acetic acid 85:10:5): 0.76

R$_f$ (n-butanol/acetic acid/water 40:40:10): 0.89.

Example 120

H-D-Ala-D-Ala-NH—(CH$_2$)$_2$—GS—OCH$_3$ 280 mg (0.37 mmol) of Z-D-Ala-D-Ala-NH—(CH$_2$)$_2$—GS—OCH$_3$ are dissolved in 5 ml of methanol. The reaction vessel is flushed several times with inert gas, 28 mg of hydrogenation catalyst (palladium/active carbon, 10%) are added and the mixture is hydrogenated at room temperature for 3 h. After the stated time, starting material is no longer present according to thin-layer chromatography (dichloromethane/methanol/acetic acid 85:10:5). The reaction mixture is membrane-filtered (Schleicher and Schuell, RC 58, 0.2 µm), the filtrate is evaporated in a rotary evaporator, diethyl ether is twice added to the residue and the mixture is again evaporated in a rotary evaporator. 225 mg (98%) of a pale yellow pulverulent solid are obtained, which is taken up in methanol and stirred at room temperature for 10 min with the addition of active carbon. After filtration, evaporation of the solvent in vacuo and drying, 190 mg (83%) of "Example 120" are obtained as a white powder.

$R_f$ (n-butanol/acetic acid/water 40:40:10): 0.55.

Example 121

H-D-Ala-D-Ala-NH—(CH$_2$)$_2$—GS—OH 120 mg (0.19 mmol) of H-D-Ala-D-Ala-NH—(CH$_2$)$_2$—GS—OCH$_3$ are dissolved in 2 ml of methanol, 2 ml of 0.1N aqueous sodium hydroxide solution are added dropwise at room temperature and the mixture is stirred at the same temperature for 4 h. The reaction solution is then adjusted to pH 3 using 2N aqueous hydrochloric acid and evaporated to dryness in a rotary evaporator.

The residue is triturated in a little ethanol and insoluble material is filtered off. The filtrate is reduced to dryness, triturated once in each case with ether and pentane, filtered and dried. 107 mg of "Example 121" are obtained as a white solid (still contains about 10% of sodium chloride).

Yield: 85%

$R_f$ (n-butanol/acetic acid/water 40:40:10): 0.54.
Example 122 was obtained in analogy to Example 121.

Example 122

Z-D-Ala-D-Ala-NH—(CH$_2$)$_2$—GS—OH
Z=benzyloxycarbonyl

Example 123 to 500 mg (2.23 mmol) of acid chloride (prepared from the corresponding carboxylic acid by reaction with thionyl chloride/a catalytic amount of DMF, 2 h reflux), in 25 ml of methylene chloride. The mixture was then stirred at room temperature for 2 h. The reaction mixture was poured into water and the aqueous phase was extracted using methylene chloride (3×). The combined organic phases were washed with saturated NaHCO$_3$ solution (1×) and dried (MgSO$_4$). Removal of the solvent and chromatography on silica gel (ethyl acetate/methanol=15:1) gave 314 mg.

b) 100 mg (1.49 mmol) of the product obtained according to a) were dissolved in 20 ml of ethanol and stirred overnight with 4 ml of 1N NaOH. For neutralization, 4 ml of hydrochloric acid were added and the mixture was extracted using ethyl acetate. The combined organic phases were washed with saturated sodium chloride solution and dried (MgSO$_4$). Removal of the solvent gave 89.1 mg of "Example 123".

$C_{36}H_{55}N_3O_8$ (657); MS (FAB, 3-NBA/LiI)=664 (M+Li$^+$).

Example 124

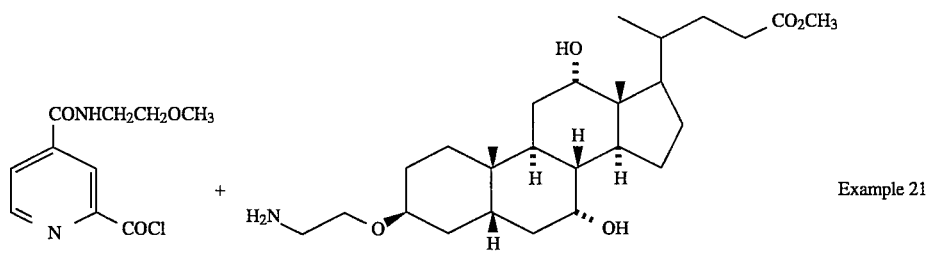

Example 21

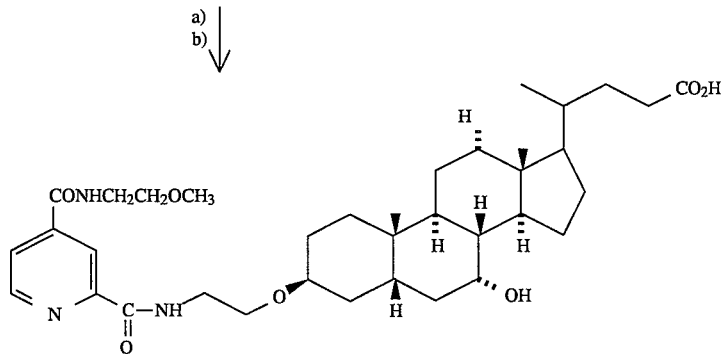

a) 1.04 g (2.23 mmol) of Example 21 in 5 ml of methylene chloride/1 ml of triethylamine were added dropwise at 0° C.

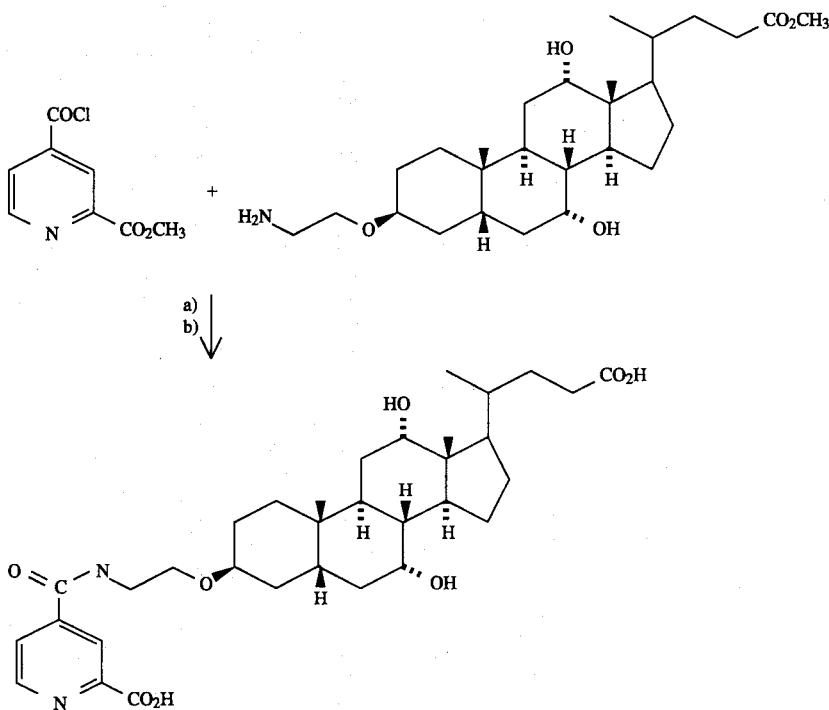

"Example 124" was obtained analogously to Example 123.

$C_{33}H_{48}N_2O_8$ (600 ); MS (FAB, 3-NBA/LiCl): 607 $(M+Li^+)$, 613 $(M+2Li—H)^+$, 619 $(M+3Li—2H)^+$.

Procedure for preparation of the lactone components for Example 71 according to DE 3,819,999:

Synthesis of 4(R)-hydroxy-6(S)-[(2,4-diisopropyl-6-p-fluorophenyl)-phenoxymethyl] tetrahydro-2H-pyran-2-one Step 1

2,4-Diisopropylphenol

The mixture obtained from 145 g (0.65 mol) of 3,5-diisopropyl- 2-hydroxybenzoic acid (XI), 540 ml (588 g, 4.55 mol) of quinoline and 7.5 g (0.024 mol) of copper chromite ($2CuO.Cr_2O_3$) is stirred at 190° C. (225° C. external temperature) for 2 hours. It is cooled to about 10° C., acidified to pH 1 to 2 using about 1 of semiconcentrated hydrochloric acid with further cooling and extracted using toluene, and the extract is washed with 2N hydrochloric acid, then with water and then with $NaHCO_3$ solution. It is dried, filtered, concentrated and distilled in a high vacuum. 105 g of the title compound XIII are obtained as a pale yellow oil, b.p. 81° to 84° C./0.2 torr.

$^1$H-NMR ($CDCl_3$): δ1.20 (6H, d); 1.25 (6H, d); 3.00 (2H, 2×hept.); 4.10 (1H, s, br); 6.50–7.00 (3H, m).

Step 2

2,4-Diisopropyl-6-bromophenol 1 g of iron powder and then, dropwise, 101 g (32.2 ml, 0.63 mol) of bromine are added in the course of 90 minutes to a solution of 102.3 g (0.57 mol) of 2,4-diisopropylphenol in 900 ml of glacial acetic acid at 95° C. The mixture is stirred for a further hour at 100° C. and cooled, the reaction mixture is partitioned between toluene and water and the toluene phase is washed with $NaHCO_3$ solution. It is dried, filtered and concentrated, and the residue is distilled in a high vacuum. 125 g of the title compound is obtained as a pale yellow oil, b.p. 85° C./0.15 torr.

$^1$H-NMR ($CDCl_3$): δ1.20 (6H, d); 1.25 (6H, d); 2.80 (1H, hept.); 3.25 (1H, hept. ); 5.33 (1H, s); 6.87–7.20 (2H, m)

MS (70 eV): m/e=256/258 $(M^+)$, 241/243 $(M^+—CH_3)$.

Step 3

1-Benzyloxy-2,4-diisopropyl-6-bromobenzene

The suspension obtained from 166.5 g (1.2 mol) of potassium carbonate in 124 g (0.48 mol) of the above bromophenol, 91.52 g (0.72 mol) of benzyl chloride and 2 1 of 2-butanone is heated to reflux for 24 hours.

The mixture is cooled and the inorganic solid is filtered off with suction, the filtrate is concentrated in vacuo and the residue is partitioned between toluene and water. The toluene phase is washed with saturated sodium chloride solution, dried, filtered and concentrated. The residue is chromatographed through silica gel using cyclohexane/toluene 9:1. 155 g of the title compound are obtained as a colorless oil.

Small amounts of benzyl chloride are removed in a high vacuum. Purification can also be achieved by distillation (b.p. 150° C./0.15 torr).

$^1$H-NMR ($CDCl_3$): δ1.18 (6H, d); 1.22 (6H, d); 2.80 (1H, hept.); 3.32 (1H, hept.); 4.90 (2H, s); 6.93–7.60 (7H, m)

MS (70 eV): m/e=346/348 $(M^+)$, 267, 254/256, 91.

Step 4

1-Benzyloxy-2,4-diisopropyl-6-p-fluorophenylbenzene

The Grignard compound is prepared from 48.62 g (0.14 mol) of the bromide from step 3 and 3.53 g (0.147 mol) of Mg turnings in 120 ml of absolute THF (~60° C., 1 hour). This Grignard solution is rapidly added to a solution of 31.08 g (0.14 mol) of 4-fluoroiodobenzene and 3.23 g (2.8 mmol) of tetrakis(triphenylphosphine)palladium(0) in 140 ml of absolute THF. The internal temperature rises to 55° to 60° C. in the course of 15 minutes. After 7 minutes, a precipitate forms. The mixture is stirred at 50° to 58° C. for 1 hour, allowed to stand at room temperature overnight and partitioned between ether and 1N hydrochloric acid, and the ether phase is washed with 1N hydrochloric acid, then with water and then with saturated $NaHCO_3$ solution. It is dried, filtered and concentrated. If necessary, the product is purified by chromatography on silica gel using cyclohexane/ toluene 4:1 or by distillation (b.p. 180° C./0.3 torr). 49.3 g of the title compound are obtained as a colorless solid, m.p. 65° to 67° C.

$^1$H-NMR (CDCl$_3$): δ1.30 (12H, d); 2.95 (1H, hept.); 3.45 (1H, hept.); 4.40 (2H, s); 6.90–7.80 (11H, m)

MS (CI): m/e=363 (M+H$^+$), 362 (M$^+$), 285, 263.

Step 5

2,4-Diisopropyl-6-p-fluorophenylphenol 4 g of 10% Pd on carbon are added to a solution of 49.3 g (0.136 mol) of the benzyl ether from step 4 in 1 l of ethyl acetate and 100 ml of glacial acetic acid and the mixture is shaken in a hydrogen atmosphere (vigorous absorption of H$_2$) for 20 minutes. The catalyst is filtered off, the filtrate is concentrated, the residue is taken up several times in toluene and the solution is in each case concentrated in vacuo. 34.4 g of the title compound are obtained as a colorless oil, b.p. 115° C./0.1 torr.

$^1$H-NMR (CDCl$_3$, 270 MHz): δ1.25 (6H, d); 1.29 (6H, d); 2.87 (1H, hept.); 3.31 (1H, hept.); 4.95 (1H, s, br); 6.88 (1H, d); 7.08 (1H, d); 7.18 (2H, m); 7.45 (2H, m).

MS (70 eV): m/e=272 (M$^+$), 257 (M$^+$—CH$_3$).

Step 6

6(S)-{(2,4-Diisopropyl-6-p-fluorophenyl)-phenoxymethyl}-3,4,5,6-tetrahydro-2(R,S)-methoxy-4(R)-(t-butyldiphenylsilyloxy)-2H-pyran 27.2 g (0.1 mol) of the phenol from step 5 are added to a suspension of 27.6 g (0.2 mol) of potassium carbonate and a spatula tipful of hydroquinone in 250 ml of abs. DMSO. The mixture is stirred at room temperature for 1 hour and the solution obtained from 56 g (0.11 mol) of 6(S)-iodomethyl-3,4,5,6-tetrahydro-2(R,S)-methoxy-4(R)-(t-butyldiphenylsilyloxy)- 2H-pyran (for preparation see EP-A 0,216,127, R$_7$=t-butyldiphenylsilyl) in 250 ml of abs. DMSO is then added. The mixture is stirred at an internal temperature of 50°–55° C. for 4 hours. TLC (silica gel, 1st development using cyclohexane/ethyl acetate 9:1, 2nd development using cyclohexane/ethyl acetate 15:1) shows complete conversion of the iodide (R$_f$ 0.5), some residual starting phenol (R$_f$ 0.7) and principally product of the formula V (R$_f$ 0.6 ). The reaction mixture is allowed to cool and is partitioned between ether and semisaturated sodium chloride solution. The aqueous phase is extracted again using ether. The combined organic phases are washed with sodium chloride solution, dried over MgSO$_4$, filtered and concentrated. The crude product is chromatographed on silica gel using toluene/cyclohexane 2:1, then 100% toluene, then toluene/ethyl acetate 30:1. 51 g of the title compound are obtained as a colorless resin.

$^1$H-NMR (CDCl$_3$): δ1.10 (9H, s); 1.28 (12H, d); 1.4–2.2 (4H, m); 2.93 (2H, 2×hept.); 3.40 (2H, m); 3.52 (3H, s); 3.97–4.40 (2H, qui+m); 4.87 (1H, dd); 6.87–7.90 (16H, m).

MS (CI): m/e=654 (M$^+$), 597 (M$^+$-tert.-Bu), 539, 519, 323, 283, 135, 127.

Step 7

6(S)-{(2,4-Diisopropyl-6-p-fluorophenyl)-phenoxymethyl}-3,4,5,6-tetrahydro-2(R,S)-hydroxy-4(R)-(t-butyldiphenylsilyloxy)-2H-pyran The solution obtained from 40.2 g (61.4 mmol) of the lactol ether from step 6 in 3 l of THF, 3 l of water and 4.2 l of glacial acetic acid is stirred at 80°–85° C. (external temperature) for 24 hours. The solvents are removed in vacuo and the residue is evaporated in vacuo 3 times using toluene. Chromatography through 2 l of silica gel using cyclohexane/ethyl acetate 12:1 gives 33.4 g (yield 85%) of the title compound as a colorless amorphous powder.

MS (FAB): m/e=640 (M$^+$), 519, 367, 323, 283, 271, 257

Step 8

6(S)-{(2,4-Diisopropyl-6-p-fluorophenyl)-phenoxymethyl}-3,4,5,6-tetrahydro-4(R)-(t-butyldiphenylsilyloxy)-2H-pyran-2-one 46.9 g (208.4 mmol) of N-iodosuccinimide are added with stirring and cooling to a solution of 33.4 g (52.1 mmol) of the lactol from step 7 and 19.25 g (52.1 mmol) of tetrabutylammonium iodide in 2.5 l of absolute methylene chloride. The mixture is stirred under nitrogen at 10° C. for 1 hour and at room temperature for 20 hours with the exclusion of light. The reaction solution is washed with water, then twice with NaHSO$_3$ solution, then with saturated NaCl solution, dried, filtered and concentrated. The residue is dissolved in a little methylene chloride and is filtered through silica gel using cyclohexane/ethyl acetate 92:8. 32.1 g of the title compound are obtained as a colorless resin.

$^1$H-NMR (CDCl$_3$, 270 MHz): δ1.06 (9H, s); 1.23 (6H, d); 1.26 (6H, d); 1.59 (2H, m); 2.41 (1H, dd); 2.59 (1H, dm); 2.90 (1H, hept.); 3.36 (1H, hept.); 3.48 (2H, AB of ABX); 4.29 (1H, qui); 4.80 (1H, m); 6.96 (1H, d); 7.03 (2H, m); 7.10 (1H, d); 7.36–7.52 (8H, m); 7.58–7.73 (4H, m).

MS (70 eV, 70° C.): m/e=638 (M$^+$), 581 (M$^+$-tert-Bu), 539, (581-propene), 283, 199.

Step 9

4(R) Hydroxy-6(S)-[(2,4-diisopropyl-6-p-fluorophenyl)-phenoxymethyl]-tetrahydro-2H-pyran-2-one 11.65 g (194 mmol) of glacial acetic acid, followed by 45.92 g (145.5 mmol) of tetrabutylammonium fluoride trihydrate are added to a solution of 31.0 g (48.5 mmol) of the silyl compound from step 8 in 1.5 l of tetrahydrofuran (filtered through basic Al$_2$O$_3$). The mixture is stirred at room temperature for 20 hours. The solvents are removed in vacuo and the residue is immediately partitioned between ether and water. The aqueous phase is extracted twice more using ether. The combined organic phases are washed with saturated sodium chloride solution, dried over MgSO$_4$, filtered and concentrated. The residue is taken up in toluene and concentrated in vacuo. The crude product is chromatographed through 2 kg of silica gel using cyclohexane/ethyl acetate 1:1. 15.7 g (yield 81%) of the title compound are obtained as a colorless solid, m.p. 145°–147° C.

$^1$H-NMR (CDCl$_3$, 270 MHz): δ1.25 and 1.27 (12H, 2×d); 1.67 (1H, s, br.); 1.76 (1H, dtd); 1.87 (1H, ddd); 2.58 (1H, ddd); 2.69 (1H, dd); 2.91 (1H, hept.); 3.39 (1H, hept.) 3.54 (2H, AB of ABX); 4.38 (1H, qui); 4.68 (1H, m); 6.97 (1H, d); 7.10 (3H, d+m); 7.51 (2H, m).

MS (FAB): m/e=400 (M$^+$), 257.

Procedure for the preparation of the lactone components for Example 73 according to DE 3,929,913

Step 1

2-Bromo-6-isopropylphenol 198.1 ml (3.85 mol) of bromine were added dropwise at −5° to 0° C. to a solution of 470 g of sodium hydroxide in 2 l of water. The mixture was stirred at this temperature for a further 10 min, The resulting sodium hypobromite solution was added dropwise at −5° to 0° C. to a solution of 464 g of a 40% strength aqueous dimethylamine solution (4.11 mol) in 50 ml of water. The mixture was stirred for a further 30 min, then the organic phase was separated off and the aqueous phase was extracted twice using 750 ml portions of methylene chloride, The combined organic phases were briefly dried over magnesium sulfate and filtered, The filtrate was added dropwise at −10° C. to a solution of 500 g (3.67 mol) of ortho-isopropylphenol in 900 ml of methylene chloride. After addition of about ⅔ of the filtrate, a solid formed and the reaction mixture became viscous and difficult to stir. 500 ml of methylene chloride were added at −10°

C. and the mixture was stirred for a further hour. The solid was filtered off with suction, washed with a little cold methylene chloride, suspended in 1.5 1 of 2N sulfuric acid and stirred at room temperature until all the solid had changed to an oil. The organic phase was separated off and the aqueous phase was extracted with methylene chloride. The combined organic phases were washed with sodium chloride solution and dried, and the solvent was removed in vacuo. The residue was distilled through a 30 cm Vigreux column in a water Jet vacuum.

391.7 g (1.82 mol) of colorless oil, b.p. 122°–124° C./ 21 torr; yield 49.6%.

NMR (60 MHz): δ=1.20 (d, 6H, CH$_3$), 3.23 (sept., 1H, CH), 5.42 (s, 1H, OH), 6.4–7.2 (m, 3H, atom. H).

Step 2
2-(p-Fluorophenyl)-6-isopropylphenol a) Three iodine crystals were added to 18.7 g (0.77 mol) of magnesium turnings and the site of addition was heated using a hot air apparatus (®Fön) until iodine vapor was visible in the flask. The mixture was cooled to room temperature and 20 ml of absolute THF were added. 131.3 g (0.75 mol) of p-bromofluorobenzene were poured into a 500 ml dropping funnel and about 2 ml of this were added to the reaction flask. The brown color of the reaction mixture rapidly disappeared and rapid evolution of heat took place to reflux. A further 50 ml of absolute THF were immediately added to the reaction mixture and the p-bromofluorobenzene in the dropping funnel was diluted with 200 ml of THF. This solution was then added dropwise in such a way that a gentle reflux was maintained. The reaction mixture was subsequently heated under reflux for a further hour and then cooled to 50° C.

b) In a second flask, the dissolved oxygen was driven out of the solution obtained from 52.0 g (0.24 mol) of 2-bromo-6-isopropylphenol in 150 ml of absolute THF by means of passage of nitrogen for 20 minutes. 1.7 g (1.5 mmol) of tetrakis(triphenylphosphine)palladium(0) were added with minimization of oxygen contact.

The Grignard solution from step a) was then transferred to this solution under nitrogen pressure by means of a double needle ("®Flex-needle", Aldrich), evolution of heat occurring. The rate of the transfer was selected in such a way that a gentle reflux was maintained. The mixture was then heated to reflux for a further 6 hours. The reaction mixture was cooled and poured onto 500 g of ice/100 ml of conc. hydrochloric acid. The organic phase was separated off and the aqueous phase was extracted using 3×100 ml of ether. The combined organic phases were washed with 100 ml of saturated sodium chloride solution and dried, and the solvents were removed. The residue was distilled through a 30 cm Vigreux column in a pump vacuum. After a forerun (30°–65° C./0.2 torr, the pure product (b.p. 107°–109° C./0.5 torr) distilled as a colorless oil which crystallized in the receiver and also even partly in the distillation bridge (m.p. 44°–46° C,). In order to avoid blockage of the bridge, this was temperature-controlled at about 50° C. Yield 37.8 g of title compound (164 mmol); 68.4% of theory. GC analysis (30 m fused silica column DB-5 "polydiphenyldimethylsiloxane", layer thickness 0.25 µm, internal diameter 0.32 mm, 180° C., injector 240° C., 1 bar of H$_2$): t$_{rot}$: 4.46 min; purity >99.9%.

NMR (270 MHz): δ=1.28 (d, 6H, CH$_3$), 3.32 (sept., 1H, CH), 5.08 (s, 1H, OH), 6.9–7.5 (m, 7H, arom. —M).

MS (DCI, isobutane): m/e=231 (M+H$^+$), 230 (M$^+$), 215 (M$^+$—CH$_3$)

Step 3
2-(p-Fluorophenyl)-4-thiocyanato-6-isopropylphenol

The suspension obtained from 70.9 g (838 mmol, 5.0 equivalents) of sodium thiocyanate in 200 ml of methanol was stirred at room temperature for 20 min. 40.0 g (173.8 mmol, 1.0 equiv.) of 2-(p-fluorophenyl)-6-isopropylphenol were added and the mixture was stirred for 20 minutes. 14.32 ml (277.8 mmol, 1.6 equiv.) of bromine were dissolved in 50 ml of methanol (exothermic) and this solution was added dropwise at 15°–20° C. to the above reaction solution during the course of 20 minutes. The reaction mixture turned yellow and the phenol dissolved completely. The reaction mixture was stirred for 30 min. TLC (toluene/cyclohexane 1:1) showed complete conversion of the starting material (R$_f$=0.54). In addition to the title compound (R$_f$=0.32), only a small amount of the corresponding para-bromo compound, which cochromatographs with the starting material (R$_f$=0.54) but can be differentiated owing to its different coloration, resulted as an impurity. The reaction mixture was poured onto 400 g of ice/400 ml of 2N hydrochloric acid and extracted using 4×200 ml of toluene. The extracts were washed with aqueous sodium sulfite solution, filtered, washed with saturated sodium chloride solution, dried and concentrated in vacuo.

The yellow solid which remained was dissolved in 500 ml of hot cyclohexane and 5 g of active carbon were added. The mixture was then heated under reflux for 5 minutes and the hot suspension was filtered in vacuo. The active carbon which was filtered off was subsequently washed with 20 ml of hot cyclohexane. The nearly colorless filtrate cooled slowly and was then cooled to 10° C. for a further 12 hours.

The colorless crystals (title compound) were filtered off with suction and dried in vacuo. 47.6 g (165.7 mmol) yield corresponds to 95.3%; m.p.: 94.5°–96° C.

NMR (60 MHz ): δ=1.26 (d, 6H, CH$_3$), 3.32 (sept., 1H, CH), 5.46 (s, 1H, OH), 7.0–7.6 (m, 6H, arom. —H).

MS (DCI, isobutane): m/e=288 (M+H$^+$), 272 (M$^+$—CH$_2$), 261.

Step 4
2-(p-Fluorophenyl)-4-(p-fluorophenylthio)-6-isopropylphenol

A THF solution (100 ml) of p-fluorophenylmagnesium bromide [from 3.11 g (128 mmol) of magnesium and 22.0 g (13.8 ml, 126 mmol) of p-bromofluorobenzene] was prepared as in step 2. The solution obtained from 6.04 g (21 mmol) of 2-(p-fluorophenyl)-4-thiocyanato-6-isopropylphenol (from step 3) in 50 ml of THF was added dropwise at 50° C. and the mixture was stirred at 40°–50° C. for a further 2 hours. The mixture was cooled and poured into 500 ml of ice-cold 2N hydrochloric acid. It was extracted three times using 200 ml of ether. The combined extracts were washed with sodium chloride solution and dried, and the solvent was removed in vacuo.

The oil which remained (title compound) (7.5 g, 21 mmol, yield~100%) was pure according to TLC (cyclohexane/ethyl acetate 9:1) and $^1$H-NMR.

NMR (60 MHz): δ=1.25 (d, 6H, CH$_3$), 3.31 (sept., 1H, CH), 5.22 (s, 1H, OH), 6.8–7.8 (m, 10H, arom. —H).

MS (DCI, isobutane): m/e=357 (M+H$^+$), 356 (M$^+$).

Step 5
Tert-butyl (3R,5S)-6-methylsulfonyloxy-3,5-O-isopropylidene- 3,5-dihydroxyhexanoate 116.2 g (1.01 mol, 1.5 equiv.) of methanesulfonyl chloride were added dropwise at 0°–5° C. to a solution of 175.7 g (676 mmol) of tert.-butyl (3R,5S)-6-hydroxy-3,5,0-isopropylidene- 3,5-dihydroxyhexanoate (see EPA 0.319,847) in 1.7 1 of absolute methylene chloride and 1.7 1 of absolute pyridine. The reaction mixture was stirred with ice-cooling for 90 min, then it was concentrated at 30° C. in vacuo and the majority of the residual pyridine was removed after taking up in toluene by stripping off in vacuo. The residue was taken up in toluene and washed twice with water, once with saturated sodium hydrogen carbonate solution, once with saturated sodium chloride solution, then dried, filtered and concentrated in vacuo. The oil which remained crystallized virtually completely at room temperature within a few minutes. The crystals were filtered off with suction, crushed on the suction filter, washed with cold petroleum ether and dried in vacuo.

192.0 g (568 mmol) of colorless solid, m.p. 75°–76° C. were obtained. Concentration of the filtrate, filtering off the crystals with suction and washing with a little cold petroleum ether yielded a further 34.8 g (103 mmol) of slightly impure product, m.p. 69°–73° C. Total yield of title compound: 226.8 g (671 mmol, 99.3%).

NMR (270 MHz, $CD_2Cl_2$): δ=1.18–1.33 (m, 1H, $CH_2$, axial), 1.36 (s, 3H, $CH_3$), 1.42 (s, 9H, tert.-Bu), 1.46 (s, 3H, $CH_3$), 1.56 (dt, 1H, $CH_2$, equat.), 2.36 (AB part of ABX system, 2H, $CH_2$), 3.03 (s, 3H, $CH_3$—$SO_2$), 4.09–4.23 (m, 3H, $OCH_2$ and O—CH), 4.24–4.37 (m, 1H, OCH).

MS (DCI, isobutane): m/e=283 ($M+H^+$—>=).

Step 6
{2,2-Dimethyl-4(S)-[(2-p-fluorophenyl-4-p-fluorophenylthio- 6-isopropyl)-phenoxymethyl]-6(R)-tert-butoxycarbonylmethyl}-1,3-dioxolane 2.02 g (14.6 mmol, 1.3 equiv.) of powdered potassium carbonate and about 10 mg or-;crown ether 18-crown-6 (Aldrich) were added to a solution of 4.0 g (11.2 mmol) of 2-(p-fluorophenyl)-4-p-(fluorophenylthio)-6-isopropylphenol (step 4) in 25 ml of dry hexamethylphosphoramide (HMPT). The suspension was stirred at room temperature for 20 min, then 4.55 g (13.5 mmol, 1.2 equiv.) of tert.butyl (3R,SS-6-methylsulfonyloxy-3,5-O-isopropylidene-3,5-dihydroxyhexanoate (step 5) were added and the mixture was stirred at 75°–80° C. for 2 days. The reaction mixture turned dark and became more viscous. It was poured into 200 ml of aqueous sodium dihydrogenphosphate solution and extracted several times using ether. The combined extracts were washed with saturated sodium chloride solution, dried and concentrated in vacuo and gave 8.64 g of a brownish oil.

Column chromatography (cyclohexane/ethyl acetate 10:1 plus 1 part per thousand of triethylamine) gave 4.96 g (8.28 mmol, 74.0% yield) of a pale yellow, viscous oil (title compound).

NMR (270 MHz, $C_6D_6$): δ=0.98–1.07 (m, 2H, $CH_2$), 1.19+1.20 (2×d, 6H, $CH(CH_3)_2$), 1.38 (s, 9H, tert.-Bu), 1.39+1.41 (2×s, 6H, $OC(CH_3)_2$), 2.12 (dd, 1H, $CH_2CO_2$), 2.42 (dd, 1H, $CH_2CO_2$), 3.27 (dd, 1H, O—$CH_2$), 3.37 (dd, 1H, O—$CH_2$), 3.65 (sept., 1H, C$\underline{H}$($CH_3$)$_2$), 3.65–3.76 (m, 1H, O—CH), 4.10–4.21 (m, 1H, O—CH), 6.60+6.82 (AA'BB' system, 4H, arom. H), 7.12–7.18 (m, 2H, arom. H), 7.22–7.29 (m, 3H, arom. H ), 7.45 (d, 1H, arom. H).

MS (DCI, isobutane): m/e=598 ($M^+$), 543 ($M+H^+$—>=), 485.

Step 7
Tert-butyl 3(R),5(S)-dihydroxy-6-[(2-p-fluorophenyl-4-p-fluorophenylthio- 6-isopropyl)phenoxy]hexanoate The solution obtained from 4.47 g (7.47 mmol) of the acetonide from step 6 was stirred at room temperature for 16 hours in 50 ml of tetrahydrofuran, 50 ml of ethanol and 5 ml of 2N hydrochloric acid. TLC (cyclohexane/ethyl acetate 1:1) showed nearly quantitative conversion of the starting material ($R_f$=0.78) to the product ($R_f$=0.59). The reaction mixture was poured into aqueous sodium hydrogen carbonate solution and extracted several times using ether. The extracts were washed with saturated sodium chloride solution, dried and concentrated in vacuo. The residue (4.46 g of brownish oil) was purified by column chromatography (cyclohexane/ethyl acetate 2:1) and gave 3.37 g (6.03 mmol) of title compound as a colorless oil (yield 80.8%).

NMR (270 MHz, $C_6D_6$): δ=1.1–approx. 1.4 (m, partially covered by strong singlets, 2H, $CH_2$), 1.18 (d, 6H, CH($CH_3$)$_2$), 1.31 (s, 9H, tert-Bu), 2.00 (dd, 1H, $CH_2$—$CO_2$), 2.13 (dd, 1H, $CH_2$—$CO_2$), 3.15 (s, broad, 1H, OH), 3.36 (AB part of ABX systems, 2H, $OCH_2$), 3.52 (s, broad, 1H, OH), 3.56 (sept., 1H, C$\underline{H}$($CH_3$)$_2$), 3.76–3.96 (m, 2H, 2×C$\underline{H}$OH), 6.61+6.79 (AA'B$\overline{\text{B}}$' system, 4H, atom. H), 7.14–7.27 (m, 5H, atom. H), 7.45 (d, 1H, arom. H).

MS (FAB, 3-NBA): m/e=558 ($M^+$), 519, 503 ($M^+$—>=+ $H^+$), 356 ($M^+$ of the phenol building block).

Step 8
4(R)-Hydroxy-6(S)-[(2-p-fluorophenyl-4-p-fluorophenylthio- 6-isopropyl)phenoxymethyl]-3,4,5,6-tetrahydro-2H-pyran-2-one 5 ml of trifluoroacetic acid were added dropwise to a solution of 5.59 g (10.0 mmol) of the tert.-butyl ester (step 7) in 20 ml of methylene chloride. The reaction mixture was stirred at room temperature for 2 hours. TLC (cyclohexane/ethyl acetate 1:1) showed quantitative conversion of the tert.-butyl ester ($R_f$=0.37) to the lactone ($R_f$=0.12) and insignificant non-polar impurities. The reaction mixture was partially neutralized using sodium hydrogen carbonate powder, then rendered neutral with sodium carbonate powder, then poured into water and extracted several times using ether. The combined organic phases were washed with sodium hydrogen carbonate solution, then with sodium chloride solution, dried, filtered and concentrated. The residue was chromatographed through a silica gel column using cyclohexane/ethyl acetate 1:1 and gave 3.88 g (8.0 mmol, yield 80%) of a colorless solid (title compound), m.p. 170°–172° C.

NMR (270 MHz): δ=1.30+1.32 (2×d, 6H, CH($\underline{CH_3}$)$_2$), 1.72–1.94 (m, 3H, $CH_2$ and OH), 2.67 (AB part of ABX system, 2H, $CH_2CO_2$), 3.47 (sept., 1H, C$\underline{H}$($CH_3$)$_2$), 3.59 (AB part of ABX system, 2H, $OCH_2$), 4.40 (m, 1H, C$\underline{H}$—OH), 4.72 (m, 1H, CH—OCO), 6.80–7.55 (m, 10H, arom. H).

MS (DCI, isobutane): m/e=484 ($M^+$), 467 ($M^+$—OH).

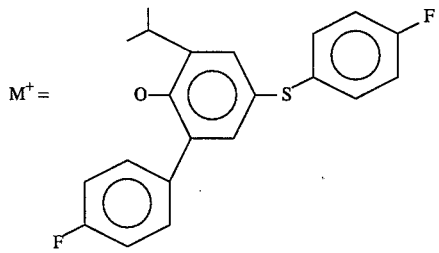

$M^+$ =

Pharmacological data
Organ-selective action of pharmacon-bile acid conjugates

Chlorambucil, [4-(bis-N-(2'-chloroethyl)-aminophenyl)]-butyric acid, is a cytostatic for the treatment of malignant tumors. Chlorambucil is mainly excreted via the kidneys. By means of covalent coupling of chlorambucil to bile acids, a liver-specific action of chlorambucil is achieved, as is illustrated by the following experiments.

1. Interaction of chlorambucil-bile acid conjugates with binding proteins for bile acids in the liver cells Bile acids are absorbed from the portal vein blood by the liver parenchyma cells and excreted again in the bile. The transport of the bile acids through membranes to the blood and bile side of the liver cell, the transport of bile acids in the various cell organelles such as mitochondria, endoplasmic reticulum etc. and the transport in the cytoplasm of the liver cell takes place by means of various specific binding proteins for bile acids. Bile acids also bind to regulatory proteins and the enzymes of bile acid metabolism.

The molecules of these physiologically relevant binding proteins for bile acids were identified and characterized by the method of photoaffinity labeling. The principle of this method consists in binding a photoreactive radioactively labeled bile acid derivative to the physiological binding protein analogously to the natural bile acids. By irradiation with UV light, highly reactive chemical intermediates such as carbenes, nitrenes or radicals are generated in this derivative which, owing to their high reactivity, immediately react with the binding proteins by addition to double bonds or insertion in single bonds and bind covalently to these. By means of this covalent linkage of the radioactive bile acid derivative with the binding protein, the binding proteins are then also radioactively labeled and can be identified by a separation of the various proteins of a liver cell, for example by electrophoresis, and their molecular weight determined.

If such a photoaffinity labeling is carried out in the presence of a substance X' which also binds to the bile acid-binding proteins, then X' will compete with the radioactive bile acid derivative for binding to the bile acid-binding proteins; the radioactive labeling of the corresponding binding proteins will thus be lower in the presence of X'. If, on the other hand, X' is a substance which does not bind to the bile acid-binding proteins, then the labeling of the bile acid-binding proteins will not be lowered by the presence of X'.

$3.6 \times 10^6$ freshly isolated hepatocytes from rat liver (about 3 mg of protein) in 1.5 ml of buffer I (118 mM NaCl, 4.74 mM KCl, 0.59 mM $KH_2PO_4$, 0.59 mM $Na_2HPO_4 \times 2\ H_2O$, 1.185 mM $MgCl_2 \times 6\ H_2O$, 24.87 mM $NaHCO_3$, 1.25 mM $CaCl_2$, 5.5 mM D-glucose, pH 7.35, buffer aerated with carbogen (95% $O_2$/5% $CO_2$) for 1 h) were incubated at 37° C. min in the dark with 1.25 µM (25 µCi) of (7,7-azo-3α-12α -dihydroxy-5β[3-$^3$H]cholan-24-oyl)-2-aminoethanesulfonic acid in the absence or in the presence of 250 µM "Example 3" and then irradiated at 350 mm with 16 RPR 3500 Å-lamps for 5 min in a Rayonet RPR-100 photoreactor. The cell suspension was then diluted with 10 ml of ice-cold buffer I and the cells sedimented by centrifuging at 1000×g for 3 minutes. The cells were resuspended again in 10 ml of buffer I and again sedimented by centrifugation. The precipitate was taken up in 600 µl of tris/HCl buffer (pH 6.8)/2% sodium dodecylsulfate (SDS)/5% 2-mercaptoethanol/10% glycerol/0.001% Bromophenol blue, heated to 90° C. for 5 min and centrifuged at 40,000×g for 20 min. The clear supernatant containing the solubilized proteins was used subsequently. In each case 100 µl (500 µg of protein) were applied to discontinuous SDS slab gels (200×170×2.7 mm, total acrylamide concentration 12%) and the proteins were separated by electrophoresis at a voltage of 50 V. After the electrophoresis, the gels were fixed in 12.5% strength trichloroacetic acid solution and stained using 0.08% Serva blue R 250 solution in 25% ethanol/8% acetic acid/67% water. After destaining, the gels were equilibrated in 1M sodium salicylate solution in 70% methanol for 20 min and then dried. The distribution of the radioactively labeled proteins was determined by the fluorographic method by placing the dried gels on Kodak-X-Omat AR X-ray films and exposing at −80° C. for 14 d. The blackened films were measured by densitometry. The decrease in the labeling of the various bile acid-binding proteins owing to the presence of "Example 3" during the photoaffinity labeling is given in % relative to the control.

| Molecular weight of the bile acid-binding liver cell proteins | | % Inhibition of bile acid-binding proteins by 250 µM "Example 3" |
|---|---|---|
| 67,000 | (albumin) | 90.5 |
| 54,000 | (membrane transport protein) | 89.6 |
| 48,000 | (membrane transport protein) | 88.8 |
| 43,000 | (cytoskeletal protein) | 88.1 |
| 36,000 | (transport protein in the cytoplasm) | 98.1 |
| 33,000 | (binding protein in mitochondria) | 93.2 |

2. Alkylation of liver cell proteins by "Example 5"

Freshly isolated hepatocytes ($2 \times 10^6$) in 2 ml of buffer I were incubated at 37° C. with 30 µCi of "Example 5". After 10, 30, 40 and 60 min, in each case 500 µl of cell suspension (500 µg of protein) were removed and diluted with 10 ml of ice-cold buffer I. After centrifuging at 1000×g for 3 minutes, the precipitate was resuspended in 10 ml of buffer I and the suspension was centrifuged again. The cell precipitates were each dissolved in 100 µl of 62.5 mM tris/HCl buffer (pH 6.8)/2% SDS/5% 2-mercaptoethanol/10% glycerol/0.001% Bromophenol blue, centrifuged at 48,000×g for 30 min and the clear supernatants were applied to discontinuous SDS slab gels (200×170×2.7 mm). After the electrophoretic separation, the gels were fixed and stained. To determine the distribution of the radioactivity, the individual gel tracks were divided into 2 mm sections, the proteins were digested with Biolute S by incubation with 0.5 ml, and after addition of 5 ml of Quickszint 501 scintillator, the samples were measured in a liquid scintillation counter.

| Incubation time (min) | Molecular wts. of labeled liver proteins (in kDa) | Radioactivity in labeled liver proteins (in cpm) |
|---|---|---|
| 0 | / | <30 |
| 10 | 48, 67 | 48: 408; 67: 102 |
| 30 | 122, 54, 48, 42, 33, 28 | 122: 1064; 54: 1811 48: 1375; 42: 1711 33: 1116; 28: 2190 |
| 40 | 122, 60, 54, 48, 42, 33, 28 | 122: 1549; 54: 2385 48: 2420; 42: 2650 33: 1474; 28: 2682 |
| 60 | 122, 54, 48, 42 35, 33, 28 | 122: 997; 54: 1949 48: 2074; 42: 1725 28: 2163 |

"Example 5" leads to a radioactive labeling of liver cell proteins, both in membranes and in the cytoplasm and in cell organelles. Besides the known physiologically relevant bile acid-binding proteins (54, 48, 33 kDa), other liver cell proteins (for example 122, 35, 28 kDa) are also labeled.

These experiments show that the alkylating property of chlorambucil relevant to the pharmacological action is also obtained after coupling of the active compound to bile acids. The radioactive labeling found originates from a labeling of proteins by the intact chlorambucilbile acid conjugate, as the radioactive labeling is localized in the bile acid moiety.

Compounds W—X—G according to the invention are thus absorbed by the liver cells and can alkylate proteins. The properties of both the chlorambucil molecule (alkylating action) and the bile acid (utilization of specific transport pathways for bile acid) are combined in W—X—G.

3. Metabolism of "Example 5" by freshly isolated hepatocytes

Freshly isolated hepatocytes ($1.8 \times 10^6$) in 750 µl of buffer I were incubated at 37° C. with 5.5 µCi of "Example 5". After 10, 20, 30, 40 and 60 min, 100 µl of the cell suspension were removed in each case, diluted with 10 ml of ice-cold buffer I and centrifuged at 1000×g for 5 min. The cell precipitate was treated twice with 100 µl of chloroform/methanol solution (1/1, v/v) each time to extract the bile acid. The organic extracts were evaporated in a stream of $N_2$, and the residues were each taken up in 20 µl of dioxane and applied to HPTLC thin layer plates. After developing the chromatogram using n-butanol/acetic acid/water (9:1:2, v/v/v) as the eluent, the plate was dried, sprayed with 1M sodium salicylate solution in methanol and, after drying, placed on a Kodak-X-Omat AR X-ray film. After exposure at −80° C. for 1 week, the film was developed and the distribution of the radioactivity was determined by densitometry. The distribution of the radioactivity in the individual metabolites is given in %.

| Incubation time (min) | "Example 5" $R_f = 0.49$ | Metabolite 1 $R_f = 0.32$ | Metabolite 2 $R_f = 0.36$ | Metabolite 3 $R_f = 0.21$ |
|---|---|---|---|---|
| 10 | 31.34 | 33.79 | 38.03 | 5.62 |
| 20 | 26.51 | 29.49 | 32.25 | 11.74 |
| 30 | 23.76 | 29.88 | 34.18 | 12.16 |
| 40 | 13.78 | 33.52 | 40.93 | 11.75 |
| 60 | 11.00 | 33.7 | 45.7 | 10.3 |

Metabolite 1: (3α,12β-dihydroxy-5β[12α-$^3$H]cholan-24-oyl)-2-aminoethanesulfonic acid
Metabolite 2: (3α,12α-dihydroxy-5β[12α-$^3$H]cholan-24-oyl)-2-aminoethanesulfonic acid
Metabolite 3: not identified "Example 5" is absorbed into the cell interior by the liver cells and reaches the intracellular locations of the metabolism. The chlorambucil-bile acid conjugate is rapidly cleaved hydrolytically into the active compound free chlorambucil and bile acid. Chlorambucil is thus brought into the form of bile acid conjugates in cells containing bile acid transport systems in order to be able to act pharmacologically therein.

Cytostatics coupled to bile acids are thus particularly suitable for the treatment of malignant tumors and metastases thereof of those cells which have the capability to absorb bile acids.

4. Interaction of bile acid derivatives with the intestinal bile acid transport system in the terminal small intestine 4.1 Preparation of brush-border membrane vesicles from the ileum of rabbits The preparation of brush-border membrane vesicles from the intestinal cells of the small intestine was carried out using the so-called $Mg^{2+}$ precipitation method. Male New Zealand rabbits (2–2.5 kg body weight) were sacrificed by intravenous injection of 0.5 ml of T-61$^R$. The small intestine was removed and rinsed with ice-cold physiological saline solution. The terminal 3/10 of the small intestine (measured in the oral-rectal direction, i.e. the terminal ileum, which contains the active $Na^+$-dependent bile acid transport system) were used for preparation of the brush-border membrane vesicles. The intestines were frozen at −80° C. under nitrogen in plastic bags. The frozen intestines were thawed in a water bath at 30° C. in order to prepare the membrane vesicles. The mucosa was scraped off and suspended in 60 ml of ice-cold 12 mM trys/HCl buffer (pH 7.1)/300 mM mannitol, 5 mM EGTA/10 mg/l of phenylmethylsulfonyl fluoride/1 mg/l of soybean trypsin inhibitor (32 U/mg)/0.5 mg/l of bovine lung trypsin inhibitor (193 U/mg)/5 mg/l of bacitracin. After diluting to 300 ml with ice-cold distilled water, the suspension was homogenized with ice-cooling for 3 minutes at 75% of maximum power using an Ultraturrax (18 rod, IKA Werk Staufen, Federal Republic of Germany). After addition of 3 ml of 1M $MgCl_2$ solution (final concentration 10 mM), the homogenate was allowed to stand at 0° C. for exactly 1 minute. As a result of addition of $Mg^{2+}$, the cell membranes aggregate and precipitate with the exception of the brush-border membranes. After centrifugation at 3,000×g (5,000 rpm, SS-34 rotor) for 15 minutes, the precipitate is discarded and the supernatant which contains the brush-border membranes is centrifuged at 26,700×g (15,000 rpm, SS-34 rotor) for 30 minutes. The supernatant was discarded, and the precipitate was rehomogenized in 60 ml of 12 mM tris/HCl buffer (pH 7.1)/60 mM mannitol, 5 mM EGTA using a Potter Elvejhem homogenizer (Braun Melsungen, 900 rpm, 10 strokes). After addition of 0.1 ml of 1M $MgCl_2$ solution and an incubation time of 15 minutes at 0° C., the mixture was again centrifuged at 3,000×g for 15 minutes. The supernatant was then again centrifuged at 46,000×g (15,000 rpm, SS-34 rotor) for 30 minutes. The precipitate was taken up in 30 ml of 10 mM tris/hepes buffer (pH 7.4)/300 mM mannitol and homogeneously resuspended by 20 strokes in a Potter Elvejhem homogenizer at 1,000 rpm. After centrifugation at 48,000×g (20,000 rpm, SS-34 rotor) for 30 minutes, the precipitate was taken up in 0.5 to 2 ml of tris/hepes buffer (pH 7.4)/280 mM mannitol (final concentration 20 mg/ml) and resuspended with the aid of a tuberculin syringe using a 27 gauge needle. The vesicles were either used immediately after preparation for transport investigations or stored at −196° C. in liquid nitrogen in 4 mg portions.

4.2 Inhibition of $Na^+$-dependent [$^3$H]taurocholate absorption into brush-border membrane vesicles of the ileum The absorption of substrates into brush-border membrane vesicles was determined by means of the so-called membrane filtration technique. 10 µl of the vesicle suspension (100 µg of protein) were pipetted on the wall of a polystyrene incubation tube (11×70 mm) as a drop which contained the incubation medium together with the corresponding ligands (90 µl). The incubation medium contained 0.75 µl=0.75 µCi [$^3$H(G)]-taurocholate (specific activity: 2.1 Ci/mmol), /0.5 µl 10 mM taurocholate/8.75 of sodium transport buffer (10 mM tris/hepes, (pH 7.4)/100 mM mannitol/100 mM NaCl) (Na—T—B) or 8.75 µl of potassium transport buffer (10 mM tris/hepes (pH 7.4)/ 100 mM mannitol/100 mM KCl) (K—T—B) and 80 µl of the relevant inhibitor solution, depending on the experiment, in Na—T buffer or K—T buffer. The incubation medium was filtered through a polyvinylidene fluoride membrane filter (SYHV LO 4NS, 0.45 µm, 4 mm φ, Millipore, Eschborn, Federal Republic of Germany). The transport measurement was begun by mixing the vesicles with the incubation medium. The concentration of taurocholate in the incubation batch was 50 µM. After the desired incubation time (customarily 1 min), the transport was stopped by addition of 1 ml of ice-cold stop solution (10 mM tris/hepes, (pH 7.4)/150 mM KCl). The resulting mixture was immediately filtered off with suction in a vacuum of 25 to 35 mbar through a membrane filter made of cellulose nitrate (ME 25, 0.45 µm, 25 mm diameter, Schleicher & Schuell, Dassell, Federal Republic of Germany). The filter was subsequently washed with 5 ml of ice-cold Stop solution.

In order to measure the absorption of the radioactively labeled taurocholate, the membrane filter was dissolved using 4 ml of the scintillator Quickszint 361 (Zinsser Analytik GmbH, Frankfurt, Federal Republic of Germany) and the radioactivity was measured by liquid scintillation counting in a TriCarb 2500 counter (Canberra Packard GmbH, Frankfurt, Federal Republic of Germany). The values measured were obtained as dpm (decompositions per minute) after calibration of the apparatus with the aid of standard samples and after correction for chemiluminescence.

The control values were in each case determined in Na—T—B and K—T—B. The difference between the absorption in Na—T—B and K—T—B gave the $Na^+$-dependent transport component. The $IC_{50}Na^+$ was designated as that concentration of inhibitor at which the $Na^+$-dependent transport component was inhibited by 50%, relative to the control; the same applies to the data for the $IC_{25}$ and $IC_{75}$ values.

was administered first, and the appropriate active compound was administered after a collection period of 2 hours. 120 min after administration of test substance, the bladder volume was measured and the urine was also collected. The bile and urine samples were stored on ice during the experiment and then deep-frozen.

5.2 Analysis of bile acid derivatives in the bile

Each 10 μl bile sample was applied to TLC plates (10×20 cm, silica gel 60 specific layer thickness 0.25 mm, No. 37581 Riedel de Haen, Seelze, Federal Republic of Germany) using Microcaps (Drummond, Broomall, USA) and the thin-layer plates were dried in the air for 20 min.

The plates were developed in the following mobile phases: Substance Mobile phase

TABLE 1

For results see Table 1
Influence of bile acid derivatives on $Na^+$-dependent taurocholate absorption

| Derivatives | Examples | $IC_{25}$ | $IC_{50}$ | $IC_{75}$ |
|---|---|---|---|---|
| natural bile acids | Taurocholate | | 48 μM | |
| | Taurochenodeoxycholate | | 23 μM | |
| | Taurolithocholate | | 12 μM | |
| | Taurolithocholate-3-sulfate | | 245 μM | |
| | Chlorambucil | no inhibition | | |
| Chlorambucil | Example 66 | 60 μM | 86.5 μM | 148 μM |
| | Example 68 | 60 μM | 89 μM | 250 μM |
| | Example 67 | 24 μM | 47.5 μM | 270 μM |
| Peptides | Example 119 | 48 μM | 134 μM | |
| | Example 120 | 38 μM | 87 μM | 178 μM |
| | Example 121 | 30 μM | 84 μM | 172 μM |
| | Example 122 | 19 μM | 107 μM | 237 μM |
| HMG-CoA reductase inhibitors | Example 125 | 12 μM | 46 μM | 104 μM |
| | Example 85 | 18 μM | 43 μM | 64 μM |
| | Example 105 | 11 μM | 22.5 μM | 45 μM |
| | Example 115 (Na salt) | 12 μM | 28 μM | 44 μM |
| | Example 87 | 16 μM | 56 μM | 70 μM |
| | Example 81 | 15 μM | 38 μM | 64 μM |
| | Example 82 (Na salt) | 17 μM | 48 μM | 80 μM |
| | Example 101 | 19 μM | 40 μM | 68 μM |
| | Example 86 | 14 μM | 62 μM | 87 μM |
| | Example 111 | 10 μM | 24 μM | 39 μM |
| | Example 94 | 4.5 μM | 13 μM | 24 μM |
| | Example 93 | 3.2 μM | 8 μM | 23 μM |
| | Example 90 | 3.8 μM | 12 μM | 27 μM |

5. Absorption of bile acid derivatives from the portal vein blood by the liver and excretion into the bile In order to investigate a selective absorption of bile acid derivatives into the liver and their hepatotropic action, the appropriate derivatives were injected as a bolus into a mesenteric vein of anesthetized rats and the excretion of these derivatives and the corresponding active compounds or active compound metabolites into the bile was analysed.

5.1 In vivo perfused liver

Male Sprague-Dawley rats (300–500 g bodyweight) had their food withdrawn and received water ad libitum. After tracheotomy, the abdomen was opened by median section under urethane anesthesia (5 mg/kg i.m. urethane 30%). The pylorus was ligated and the bile duct was cannulated by advancing a polyethylene tube (d=0.05 mm) up to the liver and the bile was drained. The volume of secretion was measured at 15 minute intervals. After a preliminary period of 60 minutes, the substances (0.5 ml of a 1 mM solution in 0.9% NaCl solution) were administered into a mesenteric vein in the course of 30 sec and the bile was collected at prestated time intervals (2, 4, 6, 8, 10, 15, 20, 30, 40, 50, 60, 70, 80, 90, 100, 110 and 120 min). The bile acid derivative

| | |
|---|---|
| Chlorambucil | Chloroform/methanol (10:1, v/v) |
| Example 67 | Butanol/glacial acetic acid/water (9:2:1, v/v) |
| Example 125 $K^+$ salt | Butanol/glacial acetic acid/water (9:2:1, v/v) |
| Example 85 | Butanol/glacial acetic acid/water (9:2:1, v/v) |
| Example 87 | Chloroform/methanol (3:1. v/v) |
| Example 86 | Chloroform/methanol (3:1. v/v) |

The constituents of the mobile phases were bought from the usual manufacturers in the highest possible purity grade. After developing and drying the plates, the distribution of the active compounds and the bile acid derivatives, or their metabolites, was determined by densitometry (CD 50 densitometer, DESAGA; Heidelberg). Detection was carried out in reflection mode with linear sampling at the wavelengths 252 nm (chlorambucil/chlorambucil conjugate) or 260 nm (remaining substances).

In order to evaluate the chromatograms, the relative intensity of the bile acid derivatives, the active compounds or the active compound metabolites on a chromatogram was given in surface area units.

TABLE 2A

W: Chlorambucil
W-X-G: Example 67
Concentration of W, W-X-G or W metabolites in surface area
units (linear mode of the densitometer)

| | W (Standard compound) | W-X-G (Bile acid-active compound derivative) | | |
|---|---|---|---|---|
| Time | Conc. of W or a metabolite of W in bile | (1) Conc. of W or a metabolite of W in bile | (2) Conc. W-X-G in bile | Total (1) + (2) |
| 2' | 1012 | 0 | 1207 | 1207 |
| 4' | 885 | 0 | 17803 | 17803 |
| 6' | 1044 | 0 | 21762 | 21762 |
| 8' | 1160 | 0 | 27280 | 27280 |
| 10' | 810 | 0 | 27346 | 27346 |
| 15' | 689 | 0 | 16673 | 16673 |
| 20' | 1481 | 0 | 10748 | 10748 |
| 30' | 704 | 0 | 5375 | 5375 |
| 40' | 511 | 0 | 1273 | 1273 |
| 50' | | 0 | 828 | 828 |
| 60' | 620 | 0 | 633 | 633 |
| 70' | 1769 | 0 | 826 | 826 |
| 80' | 501 | 0 | 635 | 635 |
| 90' | 813 | 0 | 638 | 638 |
| 100' | 523 | 0 | 559 | 559 |
| 110' | 604 | 0 | 408 | 408 |
| 120' | 531 | 0 | 383 | 383 |

TABLE 2B

| | W (Standard compound) Example 125 K$^+$ salt | | | W-X-G (Bile acid-active compound derivative) Example 85 | | |
|---|---|---|---|---|---|---|
| Time | Starting substance Example 125 | Polar metabolite | Total of standard compound + metabolite | Polar metabolite of Example 125 | W-X-G standard compound | Total of standard compound + metabolite |
| 2' | 960 | 760 | 1720 | 3240 | 2440 | 5680 |
| 4' | 1320 | 1200 | 2520 | 3440 | 3600 | 7120 |
| 6' | 1480 | 2400 | 3880 | 4160 | 4600 | 8760 |
| 8' | 1440 | 2200 | 3640 | 4920 | 4240 | 9160 |
| 10' | 3741 | 2658 | 6399 | 6000 | 3640 | 9640 |
| 15' | 5212 | 2277 | 7409 | 6040 | 2680 | 8720 |
| 20' | 8747 | 2782 | 11529 | 6200 | 2400 | 8600 |
| 30' | 10171 | 2757 | 12928 | 4160 | 1960 | 6120 |
| 40' | 5482 | 2007 | 8840 | 3560 | 1920 | 5480 |
| 50' | 4320 | 2302 | 6622 | 2920 | | |
| 60' | 3157 | 2891 | 6048 | 2520 | | |
| 70' | 2134 | 2059 | 4193 | 2440 | | |
| 80' | 1409 | 2233 | 3642 | | | |
| 90' | 1053 | 2042 | 3095 | | | |
| 100' | 1276 | 2005 | 3281 | | | |
| 110' | 1523 | 1935 | 3458 | | | |
| 120' | 1554 | 2441 | 3955 | | | |
| | Concentration in the linear mode of the densitometer | | | Concentration in the linear mode of the densitometer | | |

| | Example 86 | | | Example 87 | | |
|---|---|---|---|---|---|---|
| Time | Polar metabolite of Example 125 | W-X-G (standard compound) | Total (standard compound + metabolite) | Polar metabolite of Example 125 | W-X-G (standard compound) | Total (standard compound + metabolite) |
| 2' | 1040 | 120 | 1160 | 560 | 720 | 1280 |

-continued

| | Example 86 | | | Example 87 | | |
|---|---|---|---|---|---|---|
| Time | Polar metabolite of Example 125 | W-X-G (standard compound) | Total (standard compound + metabolite) | Polar metabolite of Example 125 | W-X-G (standard compound) | Total (standard compound + metabolite) |
| 4' | 1120 | 1440 | 2560 | 600 | 1000 | 1600 |
| 6' | 1720 | 3240 | 4960 | 640 | 1680 | 2320 |
| 8' | 2880 | 3680 | 6560 | 720 | 2280 | 3000 |
| 10' | 4080 | 3480 | 7560 | 1000 | 2440 | 3440 |
| 15' | 5160 | 1920 | 7080 | 1040 | 2240 | 3280 |
| 20' | 4880 | 720 | 5600 | 1640 | 2080 | 3720 |
| 30' | 4160 | 320 | 4480 | 1600 | 1480 | 3000 |
| 40' | 3080 | 50 | <3130 | 1520 | 920 | 2440 |
| 50' | 2960 | <50 | <3010 | 1840 | 520 | 2360 |
| 60' | 2560 | <50 | <2610 | 2000 | 400 | 2400 |
| 70' | 2120 | <50 | <2170 | 1520 | 360 | 1880 |
| 80' | 1920 | <50 | <1970 | 1680 | | |
| 90' | 1680 | <50 | <1730 | 1600 | | |
| 100' | 1440 | <50 | <1490 | 1440 | | |
| 110' | 1280 | <50 | <1330 | 1440 | | |
| 120' | 1040 | <50 | <1090 | | | |
| | Concentration data in the linear mode of the densitometer | | | Concentration data in the linear mode of the densitometer | | |

We claim:

1. A bile acid conjugate compound of the formula I

W—X—G   I consisting of a modified bile acid G—X—, wherein G is a bile acid radical in the form of the free acid, an ester or amide or a salt or a form derivatized on the alcohol groups, and X is a connecting member selected from the following groups

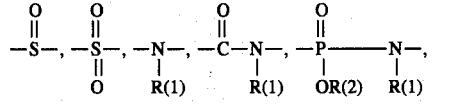

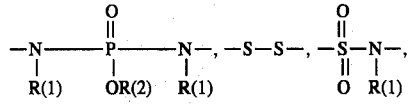

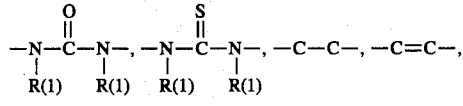

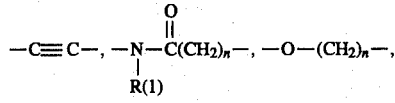

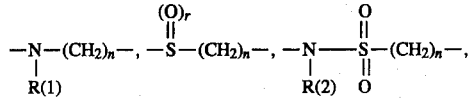

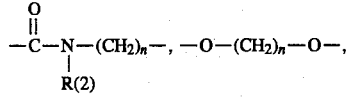

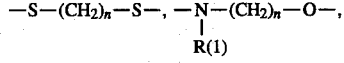

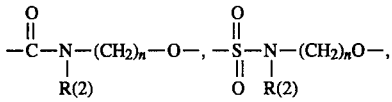

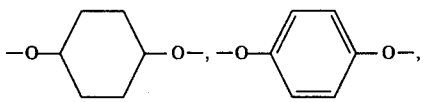

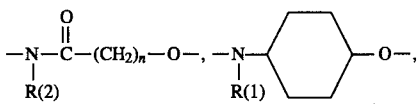

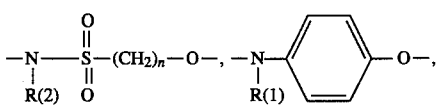

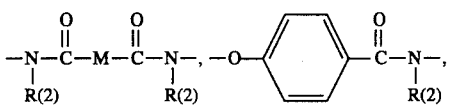

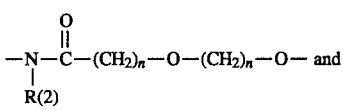

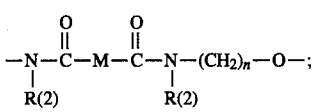

in which

R(1)=H, $(C_1-C_8)$-alkyl, the group

a phenyl radical which is unsubstituted or monosubstituted to trisubstituted by F, CL, Br, $(C_1-C_4)$-alkyl or $(C_1-C_4)$-alkoxy, or a benzyl radical which is unsubstituted or monosubstituted to trisubstituted by F, Cl, Br, $(C_1-C_4)$-alkyl or $(C_1-C_4)$-alkoxy, R(2)=H, $(C_1-C_8)$-alkyl, a phenyl radical which is unsubstituted or monosubstituted to trisubstituted by F, Cl, Br, $(C_1-C_4)$-alkyl or $(C_1-C_4)$-alkoxy, or a benzyl radical which is unsubstituted or monosubstituted to trisubstituted by F, Cl, Br, $(C_1-C_4)$-alkyl or $(C_1-C_4)$-alkoxy, m=0–6, n=1–16, p=1, 2 or 3, r=0–2 and $M = -(CH_2)_m-, -(HC=CH)_p-, -C\equiv C-,$

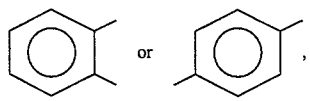

and an active compound moiety W which is

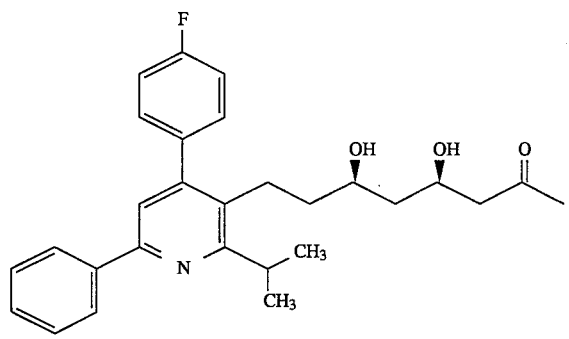

2. A compound of the formula I as claimed in claim 1, wherein the following radicals have the following meaning:

G is

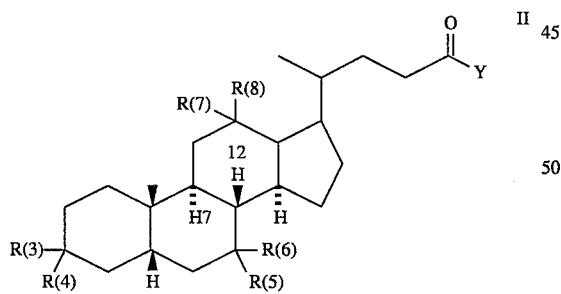

in which R(3)–R(8) are identical or different and have the following meaning:

a bond to W—X—, where altogether up to two W—X— units may be bonded,

R(3) and R(4), R(5) and R(6), R(7) and R(8) are in each case jointly the oxygen of a carbonyl group,

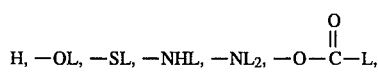

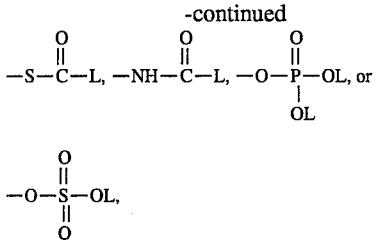

where L is H, a saturated or unsaturated alkyl radical having 1–10 carbon atoms, which is branched or unbranched, cycloalkyl having 3–8 carbon atoms, a phenyl radical which is unsubstituted or monosubstituted to trisubstituted by F, Cl, Br, $(C_1-C_4)$-alkyl or $(C_1-C_4)$-alkoxy, or a benzyl radical which is unsubstituted or monosubstituted to trisubstituted by F, Cl, Br, $(C_1-C_4)$-alkyl or $(C_1-C_4)$-alkoxy;

and in which Y has the following meaning: —OL or —NHL where L has the abovementioned meaning, an amino acid or aminosulfonic acid bonded via the amino group and its $(C_1-C_4)$-alkyl esters and alkali metal and alkaline earth metal salts, —OKa, where Ka is a cation such as an alkali metal or alkaline earth metal ion or, alternatively, a quaternary ammonium ion;

X is

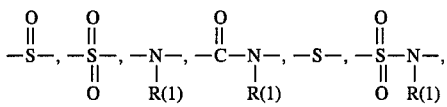

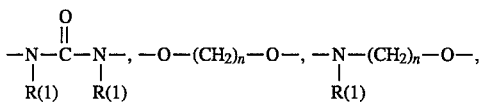

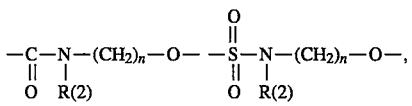

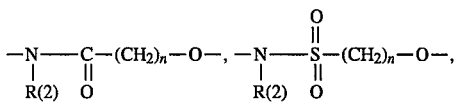

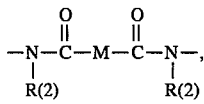

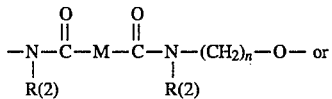

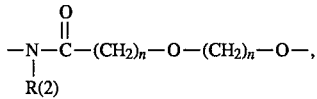

where

R(1)=H, $(C_1-C_8)$-alkyl, the group $$R(2)-\overset{\overset{O}{\|}}{C},$$

a phenyl radical which is unsubstituted or monosubstituted to trisubstituted by F, Cl, Br, $(C_1-C_4)$-alkyl or $(C_1-C_4)$-alkoxy, or a benzyl radical which is unsubstituted or monosubstituted to trisubstituted by F, Cl, Br, $(C_1-C_4)$-alkyl or $(C_1-C_4)$-alkoxy;

R(2)=H, $(C_1-C_4)$-alkyl, a phenyl radical which is unsubstituted or monosubstituted to trisubstituted by F, Cl, Br, $(C_1-C_4)$-alkyl or $(C_1-C_4)$-alkoxy, or a benzyl radical which is unsubstituted or monosubstituted to trisubstituted by F, Cl, Br, $(C_1-C_4)$-alkyl or $(C_1-C_4)$-alkoxy, n=1.16 and M=—$(CH_2)_m$— where m=2;

where G and W may be bonded to either end of X, and W is

[chemical structure: fluorophenyl-substituted pyridine with diol and ketone side chain]

3. A compound of the formula I as claimed in claim 1, wherein the following radicals have the following meaning:

G is

[steroid structure labeled II with R(3)–R(8) substituents and Y group]

where R(3)–R(8) are identical or different and have the following meaning: a bond to W—X—, where up to two W—X— units may be bonded, H, —OL, —NHL, $$-O-\overset{\overset{O}{\|}}{C}-L, \quad -NH-\overset{\overset{O}{\|}}{C}-L, \quad O-\overset{\overset{O}{\underset{\|}{\|}}}{S}-OL, \quad -O-\overset{\overset{O}{\|}}{\underset{OL}{P}}-OL,$$

or L where L is H, a saturated alkyl radical having 1–6 carbon atoms, which may be branched or unbranched, or a phenyl radical which is unsubstituted or monosubstituted to trisubstituted by F, Cl, Br, $(C_1-C_4)$-alkyl or $(C_1-C_4)$-alkoxy;

Y is: OL, —NHL —OKa, where Ka is an alkali metal or alkaline earth metal cation or an ammonium ion,

—NH—$CH_2$—$CO_2H$, —NH—$(CH_2)_2SO_3H$, $$-\underset{\underset{CH_3}{|}}{N}-CH_2CO_2H, \text{ or } -NH-\underset{\underset{R(9)}{|}}{CH}CO_2H,$$

where R(9) is methyl, isopropyl, isobutyl, 2-butyl, benzyl, 4-hydroxybenzyl, hydroxymethyl, 1-hydroxyethyl, $H_3CSCH_2CH_2$—, $HO_2CCH_2$—, or $HO_2CCH_2CH_2$—, the connecting member X, where G and W may be bonded to either end of X, is $$-\underset{\underset{R(1)}{|}}{N}-, \quad -\overset{\overset{O}{\|}}{C}-\underset{\underset{R(1)}{|}}{N}-, \quad -\overset{\overset{O}{\underset{\|}{\|}}}{\underset{\underset{O}{}}{S}}-\underset{\underset{R(1)}{|}}{N}-, \quad -O-(CH_2)_n-O-,$$

$$-\underset{\underset{R(1)}{|}}{N}-(CH_2)_n-O-, \quad -\underset{\underset{R(2)}{|}}{N}-\overset{\overset{O}{\|}}{C}-(CH_2)_n-O-,$$

$$-\overset{\overset{O}{\|}}{\underset{\underset{O}{}}{C}}-\underset{\underset{R(2)}{|}}{N}-(CH_2)_n-O-, \quad -\overset{\overset{O}{\underset{\|}{\|}}}{\underset{\underset{O}{}}{S}}-\underset{\underset{R(2)}{|}}{N}-(CH_2)_n-O-,$$

$$-\underset{\underset{R(2)}{|}}{N}-\overset{\overset{O}{\|}}{C}-M-\overset{\overset{O}{\|}}{C}-\underset{\underset{R(2)}{|}}{N}-(CH_2)_n-O-, \text{ or}$$

$$-\underset{\underset{R(2)}{|}}{N}-\overset{\overset{O}{\underset{\|}{\|}}}{\underset{\underset{O}{}}{S}}-(CH_2)_n-O-$$

where

R(1)=H, $(C_1-C_8)$-alkyl, $$R(2)-\overset{\overset{O}{\|}}{C},$$

phenyl, benzyl, a phenyl radical which is unsubstituted or monosubstituted to trisubstituted by F, Cl, Br, $(C_1-C_4)$-alkyl or $(C_1-C_4)$-alkoxy, or a benzyl radical which is unsubstituted or monosubstituted to trisubstituted by F, Cl, Br, $(C_1-C_4)$-alkyl or $(C_1-C_4)$-alkoxy;

R(2)=H, $(C_1-C_8)$-alkyl, a phenyl radical which is unsubstituted or monosubstituted to trisubstituted by F, Cl, Br, $(C_1-C_4)$-alkyl or $(C_1-C_4)$-alkoxy, or a benzyl radical which is unsubstituted or monosubstituted to trisubstituted by F, Cl, Br, $(C_1-C_4)$-alkyl or $(C_1-C_4)$-alkoxy, n=1–16 and M=—$CH_2$—$CH_2$— or —CH=CH—, and W is

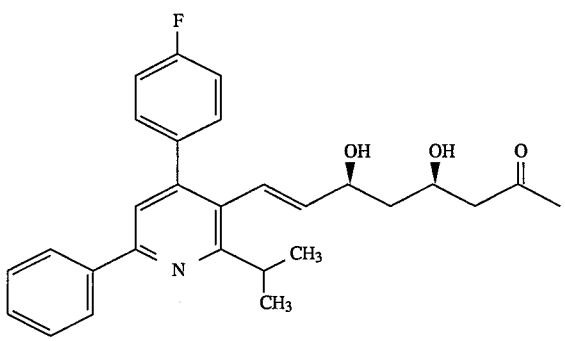

4. A pharmaceutical composition for the enhancement of absorption of a pharmaceutically active radical W, as defined in claim 1, in organs connected to the enterohepatic system comprising an effective amount for said enhancement of a compound I as claimed in claim 1 together with a pharmaceutically acceptable carrier.

5. A method for the enhancement of absorption of a pharmaceutically active radical W, as defined in claim 1, by organs connected to the enterohepatic system which comprises administering to a patient in need of such enhancement an effective amount of a compound I as claimed in claim 1.

* * * * *